US011013684B2

(12) United States Patent
Rees

(10) Patent No.: US 11,013,684 B2
(45) Date of Patent: May 25, 2021

(54) BODY FLUID EXPANDERS COMPRISING N-SUBSTITUTED AMINOSULFONIC ACID BUFFERS

(71) Applicant: AQIX, Ltd., London (GB)

(72) Inventor: Douglas Rees, London (GB)

(73) Assignee: AQIX, Ltd., London (GB)

( * ) Notice: Subject to any disclaimer, the term of this patent is extended or adjusted under 35 U.S.C. 154(b) by 381 days.

(21) Appl. No.: 14/540,597

(22) Filed: Nov. 13, 2014

(65) Prior Publication Data

US 2015/0139964 A1    May 21, 2015

Related U.S. Application Data

(62) Division of application No. 12/667,309, filed as application No. PCT/GB2008/002268 on Jul. 3, 2008, now abandoned.

(30) Foreign Application Priority Data

Jul. 3, 2007  (GB) ..................................... 0712833

(51) Int. Cl.
| | |
|---|---|
| *A61K 47/18* | (2017.01) |
| *A61K 31/7004* | (2006.01) |
| *A61K 31/047* | (2006.01) |
| *A61K 31/198* | (2006.01) |
| *A61K 33/14* | (2006.01) |
| *A61K 31/14* | (2006.01) |
| *A61K 31/51* | (2006.01) |
| *A61K 38/28* | (2006.01) |
| *A61K 31/165* | (2006.01) |
| *A61K 9/00* | (2006.01) |
| *A61K 47/02* | (2006.01) |
| *A61K 31/205* | (2006.01) |
| *A61K 47/20* | (2006.01) |

(52) U.S. Cl.
CPC .......... *A61K 9/0026* (2013.01); *A61K 31/047* (2013.01); *A61K 31/14* (2013.01); *A61K 31/165* (2013.01); *A61K 31/198* (2013.01); *A61K 31/205* (2013.01); *A61K 31/51* (2013.01); *A61K 31/7004* (2013.01); *A61K 33/14* (2013.01); *A61K 38/28* (2013.01); *A61K 47/02* (2013.01); *A61K 47/20* (2013.01)

(58) Field of Classification Search
None
See application file for complete search history.

(56) References Cited

U.S. PATENT DOCUMENTS

| | | | | |
|---|---|---|---|---|
| 3,920,814 | A | * | 11/1975 | Bocher ................... A61K 31/65 424/115 |
| 5,130,230 | A | * | 7/1992 | Segall ................... A61K 9/0026 128/897 |
| 5,571,801 | A | * | 11/1996 | Segall ................... A01N 1/0221 424/94.61 |
| 5,574,019 | A | | 11/1996 | Segall et al. |
| 5,716,847 | A | | 2/1998 | Simmons et al. |
| 6,946,241 | B2 | * | 9/2005 | Rees ..................... A01N 1/0226 435/1.1 |
| 2001/0010827 | A1 | | 8/2001 | Altura et al. |
| 2002/0068265 | A1 | | 6/2002 | Lopez et al. |
| 2003/0073227 | A1 | | 4/2003 | Hull et al. |
| 2003/0077655 | A1 | * | 4/2003 | Rees ........................ A01N 1/02 435/7.1 |

OTHER PUBLICATIONS

Li et al. (Hepatobiliary & Pancreatic Diseases International, vol. 2, No. 4, 549-552 (Nov. 2003); of record in IDS of Nov. 13, 2014).*
Li et al. (Hepatobiliary & Pancreatic International, vol. 2, No. 4, 549-552 (Nov. 2003); of record in IDS of Nov. 13, 2014.*
Fogh-Anderson et al., "Composition of Interstitial Fluid", Clinical Chemistry, vol. 41, No. 10, pp. 1522-1525 (1995).
Li et al., "Protective mechanism of L-arginine against liver ischemic-reperfusion injury in rats", Hepatobiliary & Pancreatic Diseases International, vol. 2, No. 4, pp. 549-552 (2003).
Maggs et al., "Interstitial fluid Concentrations of Glycerol, Glucose, and Amino Acids in Human Quadricep Muscle and Adipose Tissue", J. Clin. Invest., vol. 96, pp. 370-377 (1995).
http://online.haematologica.org/eha12/images/1002.jpg (accessed May 6, 2013).
Otrock et al., "Superior Efficacy of a Novel Plasma Subsitute, AQIXRS-I, Compared to Physiological Saline in a Rodent Model of Hemorrhage", Haematologica/The Hematology Journal, vol. 92(s1), pp. 371-372 (2007).
International Search Report for PCT/GB2008/002268 dated Nov. 24, 2008.
Maruyama, et al., "Myocardial protection: efficacy of a novel magnesium-based cardioplegia (RS-C) compared to St Thomas' Hospital cardioplegic solution." Interact Cardiovasc Thorac Surg 7, No. 5 (2008): 745-749.

(Continued)

*Primary Examiner* — Patricia Duffy
*Assistant Examiner* — Garen Gotfredson
(74) *Attorney, Agent, or Firm* — FisherBroyles, LLP; Victoria L. Boyd

(57) ABSTRACT

A buffered body fluid expander solution, in which the buffer is a physiologically acceptable buffer that is not an inorganic phosphate buffer, comprises calcium ions and magnesium ions at a concentration ratio of 5:1 to 1:1. The solutions are useful for the manufacture of medicaments and blood volume expanders, for treating hypovolemia or for treating the loss of extracellular and interstitial fluid in subjects suffering with burns, for treating respiratory and/or metabolic acidosis in a subject, for perfusion of the abdominal cavity during peritoneal dialysis of a subject with acute renal failure or an acute toxicity condition, for preventing and/or ameliorating reperfusion injury, and for delivering a therapeutic, test and/or synergistic agent to a subject, including a biological agent, such as at least one stem cell, peptide or genomic derived protein.

31 Claims, 38 Drawing Sheets

(56) References Cited

OTHER PUBLICATIONS

Ray et al., "Assessing the role of an oxygenated organ flush in DCD donors" Poster, British Transplantation Society Conference, Feb. 22-24, 2012 Glasgow, United Kingdom.

Ray et al., "The oxygenated flush—a simpler way to resuscitate DCD kidneys?" Poster, British Transplantation Society Conference, Feb. 22-24, 2012 Glasgow, United Kingdom.

* cited by examiner

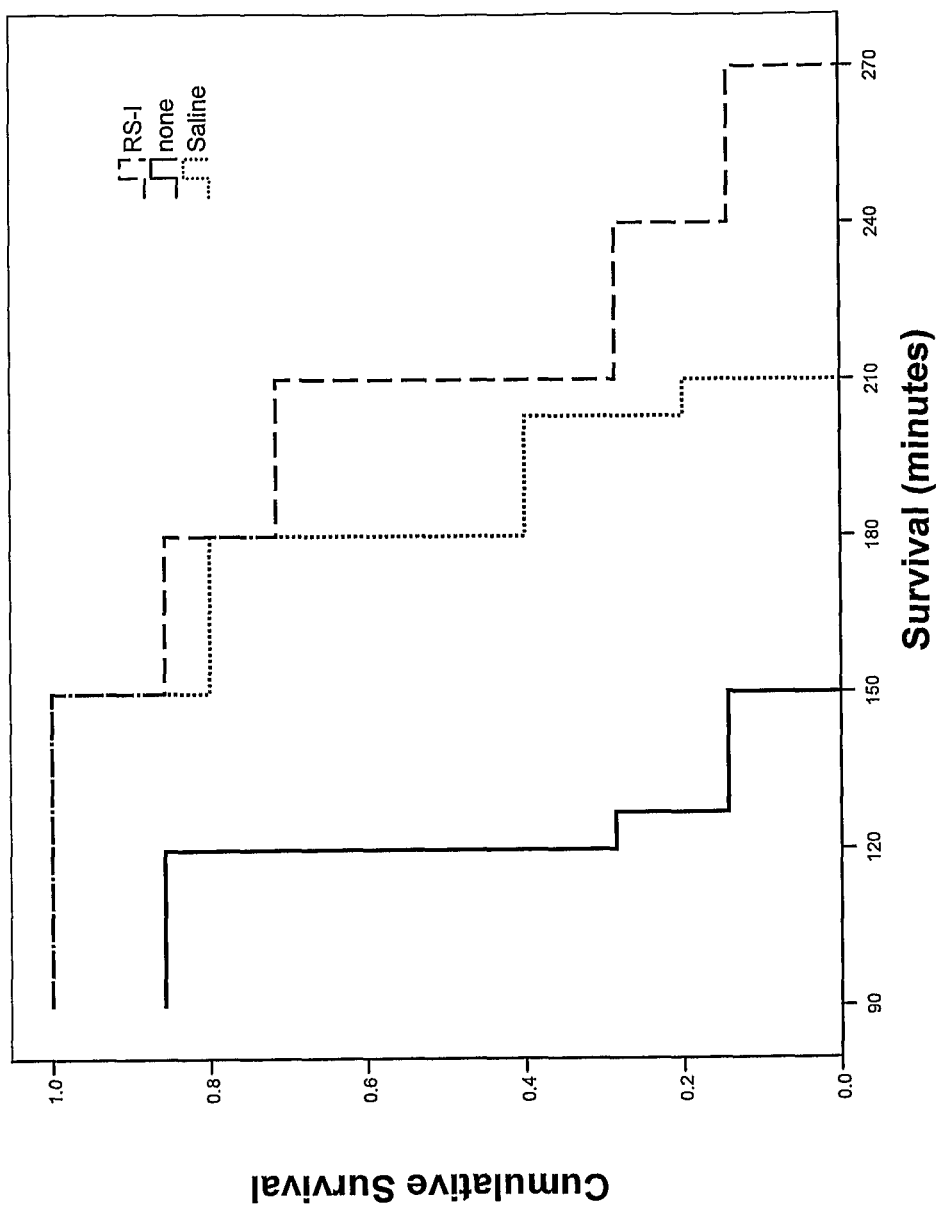
Figure 1 Cumulative Rat Survival Time in Minutes

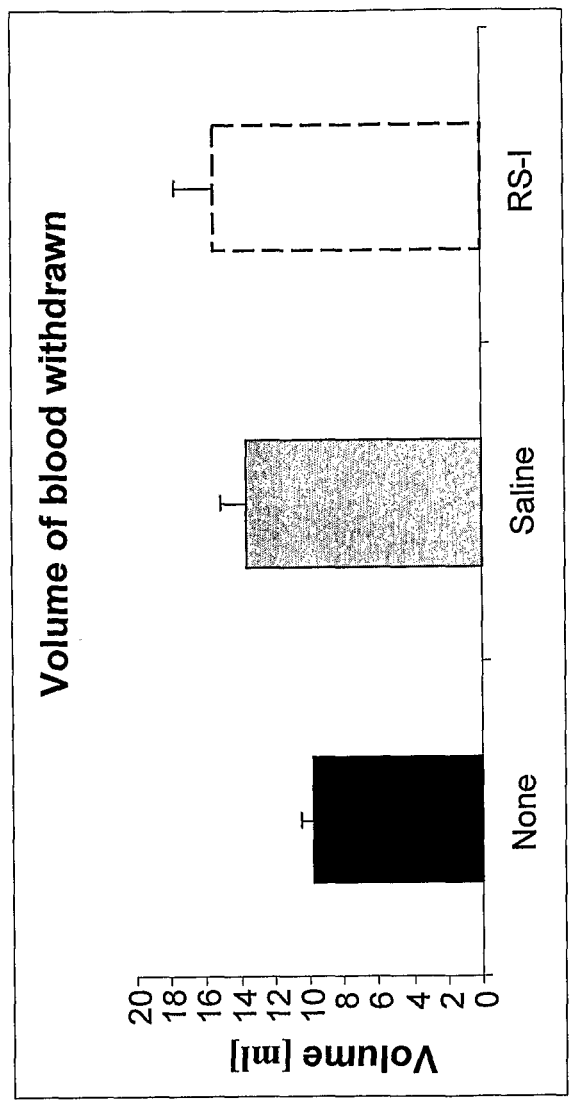
Figure 2  Total blood volume withdrawn in each of the study arms.

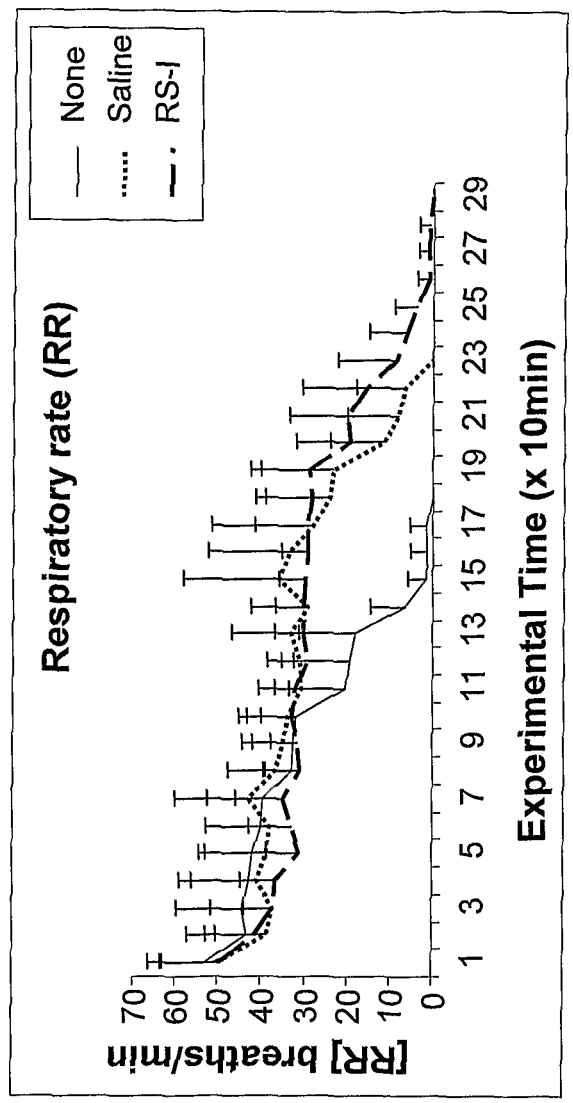
Figure 3 Respiratory rates of rats over experimental time in the various trial arms.

FIGURE 4A

| Laboratory Data Analyses | REFERENCE (units) | Values | PIG#1 (8/31/2006) DAY 1 | PIG #1 (9/1/2006) DAY 2 | PIG# 1 (9/2/2006) DAY 3 |
|---|---|---|---|---|---|
| CBC | | | | | |
| WBCs | mil/mm$^3$ | 7 to 20 | 20400 | 23900 | 18600 |
| RBCs | mil/mm$^3$ | 5 to 8 | 6.67 | 6.56 | 6.46 |
| Hg | g/dL | 6.9 to 12.7 | 12.1 | 12 | 12 |
| Hct | % | 15 – 37 | 36 | 35 | 35 |
| MCV | Fl | 50 – 68 | 54 | 54 | 54 |
| MCH | Pg | 17 – 23 | 18 | 18 | 19 |
| MCHC | g/dL | 30 – 36 | 34 | 34 | 35 |
| RDW | % | | 18 | 19 | 19 |
| WBC-diff | | | | | |
| Polymorphs | % | 28 – 50 | 47 | 61 | 59 |
| Lymphocytes | % | 40 – 60 | 51 | 33 | 38 |
| Monocytes | % | 2 to 10 | 1 | 6 | 3 |
| Eosinophils | % | 0 – 10 | 1 | 0 | 0 |
| Platelets | mm$^3$ | 120k - 720k | 526000 | 522000 | 458000 |
| Glucose | mg/dL | 65 – 150 | 77 | 59 | 97 |
| Lactic acid | mmole/L | 1.91 - 2.47 | 5.76 | 1.49 | 1.66 |
| BUN | mg/dL | 6 – 30 | 11 | 14 | 16 |
| Creatinine | mg/dL | 0.8 - 3.6 | 0.8 | 0.9 | 1 |
| Sodium | mmole/L | 135 – 150 | 139 | 139 | 142 |
| Potassium | mmole/L | 4.1 - 6.9 | 3.9 | 3.8 | 3.8 |
| Chloride | mmole/L | 94 – 113 | 101 | 103 | 102 |
| Hydrogen Carbonate | mmole/L | 22 – 46 | 22 | 26 | 30 |
| Calcium | mmole/L | 2.07 - 3.32 | 2.40 | 2.30 | 2.35 |
| Magnesium | mmole/L | 0.70 - 1.00 | 0.90 | 0.82 | 0.78 |
| Phosphate | mg/dL | 7.0 – 10.9 | 8.6 | 8.2 | 7.9 |
| Osmolality | mOsm/kg | 280 – 306 | 286 | 295 | 295 |
| SGOT (AST) | IU/L | 29 – 1140 | 73 | 64 | 60 |
| SGPT (ALT) | IU/L | 7 - 161 | 66 | 69 | 70 |
| LDH | IU/L | 286 -12,000 | 778 | 771 | 731 |
| CPK | IU/L | 311- 16,700 | N/A | 2760 | 1887 |
| Prothrombin | | | | | |
| Pt | Sec | | 10.6 | 10.8 | 10.7 |
| Control | Sec | | 12 | 12 | 13 |
| INR (ISI) | (ratio) | 0.8 - 1.2 | 0.9 | 0.9 | 0.9 |
| aPTT | Sec | 17.8 – 23.3 | 20 | 19 | 19.5 |
| Control | Sec | | 29.5 | 30 | 30.5 |
| aPTT (ratio) | | | 0.7 | 0.6 | 0.6 |
| Fibrinogen | g/L | 2.06 - 6.13 | 2.8 | 3.6 | 3.1 |

FIGURE 4B

| Laboratory Data Analyses | REFERENCE (units) Values | | PIG #2 (9/7/2006) DAY 1 | PIG #2 (9/8/2006) DAY 2 | PIG #2 (9/9/2006) DAY 3 | PIG #2 (13/09/06) DAY 7 |
|---|---|---|---|---|---|---|
| CBC | | | | | | |
| WBCs | mil/mm$^3$ | 7 to 20 | 24700 | 19200 | 20000 | 29400 |
| RBCs | mil/mm$^3$ | 5 to 8 | 6.46 | 6.39 | 6.29 | 6.26 |
| Hg | g/dL | 6.9 to 12.7 | 11.2 | 11.1 | 10.9 | 10.7 |
| Hct | % | 15 – 37 | 32 | 32 | 32 | 32 |
| MCV | Fl | 50 – 68 | 50 | 50 | 51 | 52 |
| MCH | Pg | 17 – 23 | 17 | 17 | 17 | 17 |
| MCHC | g/dL | 30 – 36 | 35 | 35 | 34 | 33 |
| RDW | % | | 20 | 21 | 22 | 28 |
| WBC-diff | | | | | | |
| Polymorphs | % | 28 – 50 | 32 | 19 | 36 | 50 |
| Lymphocytes | % | 40 – 60 | 67 | 77 | 58 | 43 |
| Monocytes | % | 2 to 10 | 0 | 4 | 5 | 6 |
| Eosinophils | % | 0 – 10 | 1 | 0 | 0 | 1 |
| Platelets | mm$^3$ | 120k – 720k | 121000 | 586000 | 575000 | 563000 |
| Glucose | mg/dL | 65 – 150 | 87 | 96 | 92 | 96 |
| Lactic acid | mmole/L | 1.91 - 2.47 | 0.61 | 0.83 | 1.63 | 5.13 |
| BUN | mg/dL | 6 – 30 | 14 | 14 | 18 | 16 |
| Creatinine | mg/dL | 0.8 – 3.6 | 0.6 | 0.7 | 0.8 | 0.7 |
| Sodium | mmole/L | 135 – 150 | 139 | 144 | 149 | 140 |
| Potassium | mmole/L | 4.1 – 6.9 | 4.1 | 4.3 | 4.3 | 4 |
| Chloride | mmole/L | 94 – 113 | 99 | 107 | 110 | 99 |
| Hydrogen Carbonate | mmole/L | 22 – 46 | 32 | 27 | 30 | 28 |
| Calcium | mmole/L | 2.07 - 3.32 | 2.47 | 2.52 | 2.62 | 2.62 |
| Magnesium | mmole/L | 0.70 - 1.00 | 0.90 | 1.03 | 0.99 | 0.90 |
| Phosphate | mg/dL | 7 – 10.9 | 9.4 | 8.7 | 8.4 | 8.8 |
| Osmolality | mOsm/kg | 280 - 306 | 287 | 300 | 312 | 291 |
| SGOT (AST) | IU/L | 29 - 1140 | 88 | 70 | 46 | 38 |
| SGPT (ALT) | IU/L | 7 - 161 | 40 | 59 | 54 | 66 |
| LDH | IU/L | 286 -12,000 | 767 | 795 | 748 | 623 |
| CPK | IU/L | 311- 16,700 | 5234 | 4595 | 3542 | 743 |
| Prothrombin | | | | | | |
| Pt | Sec | | 11.4 | 12.1 | 11.5 | 11.5 |
| Control | Sec | | 12 | 12 | 12 | 12 |
| Pt ratio | | | 1 | 1 | 1 | 1 |
| INR (ISI) | (ratio) | 0.8 – 1.2 | 1 | 1 | 1 | 1 |
| aPTT | Sec | 17.8 - 23.3 | 17 | 22.5 | 20 | 19.5 |
| Control | Sec | | 29.5 | 30 | 30 | 29 |
| aPTT (ratio) | | | 0.6 | 0.8 | 0.7 | 0.7 |
| Fibrinogen | g/L | 2.06 - 6.13 | 3.2 | 3.3 | 2.9 | 2.1 |

FIGURE 4C

| Laboratory Data Analyses | REFERENCE (units) Values | | PIG #3 (9/14/2006) DAY 1 | PIG #3 (9/15/2006) DAY 2 | PIG #3 (16/09/06) DAY 3 | PIG #3 (20/09/06) DAY 7 |
|---|---|---|---|---|---|---|
| CBC | | | | | | |
| WBCs | mil/mm$^3$ | 7 to 20 | 23100 | 11900 | 18200 | 26000 |
| RBCs | mil/mm$^3$ | 5 to 8 | 6.46 | 6.29 | 6.1 | 6.24 |
| Hg | g/Dl | 6.9 to 12.7 | 11.2 | 10.9 | 10.5 | 11.1 |
| Hct | % | 15 – 37 | 32 | 31 | 31 | 31 |
| MCV | Fl | 50 – 68 | 49 | 50 | 50 | 50 |
| MCH | Pg | 17 – 23 | 17 | 17 | 17 | 18 |
| MCHC | g/dL | 30 – 36 | 35 | 35 | 35 | 35 |
| RDW | % | | 34 | 32 | 34 | 22 |
| WBC-diff | | | | | | |
| Polymorphs | % | 28 – 50 | 54 | 28 | 29 | 59 |
| Lymphocytes | % | 40 – 60 | 45 | 66 | 67 | 28 |
| Monocytes | % | 2 to 10 | 1 | 1 | 4 | 13 |
| Eosinophils | % | 0 – 10 | 0 | 1 | 0 | 0 |
| Platelets | mm$^3$ | 120k - 720k | 455000 | 389000 | 390000 | 337000 |
| Glucose | mg/dL | 65 – 150 | 81 | 96 | 95 | 78 |
| Lactic acid | mmole/L | 1.91 - 2.47 | 0.68 | 0.46 | 1.14 | 0.31 |
| BUN | mg/dL | 6 – 30 | 11 | 13 | 11 | 10 |
| Creatinine | mg/dL | 0.8 – 3.6 | 0.8 | 0.9 | 0.9 | 0.7 |
| Sodium | mmole/L | 135 – 150 | 142 | 138 | 139 | 138 |
| Potassium | mmole/L | 4.1 – 6.9 | 4.1 | 4.1 | 4.5 | 4.5 |
| Chloride | mmole/L | 94 – 113 | 103 | 101 | 102 | 101 |
| Hydrogen Carbonate | mmole/L | 22 – 46 | 28 | 29 | 29 | 29 |
| Calcium | mmole/L | 2.07 - 3.32 | 2.42 | 2.42 | 2.42 | 2.40 |
| Magnesium | mmole/L | 1.7 - 2.44 | 0.82 | 0.74 | 0.86 | 0.86 |
| Phosphate | mg/dL | 7.0 - 10.9 | 7.7 | 7.7 | 8.1 | 7.8 |
| Osmolality | mOsm/kg | 280 - 306 | 290 | 290 | 295 | 289 |
| SGOT (AST) | IU/L | 29 - 1140 | 33 | 36 | 26 | 22 |
| SGPT (ALT) | IU/L | 7 - 161 | 26 | 32 | 35 | 65 |
| LDH | IU/L | 286 -12,000 | 551 | 605 | 561 | 576 |
| CPK | IU/L | 311- 16,700 | 1609 | 2494 | 1407 | 252 |
| Prothrombin | | | | | | |
| Pt | Sec | | 11.2 | 11.3 | 11.1 | 10.9 |
| Control | Sec | | 12 | 12 | 12 | 12 |
| INR (ISI) | (ratio) | | 0.9 | 0.9 | 0.9 | 0.9 |
| aPTT | Sec | 0.8 – 1.2 | 17 | 17 | 19.5 | 19 |
| Control | Sec | 17.8 - 23.3 | 29.5 | 29.5 | 30 | 30 |
| aPTT (ratio) | | | 0.6 | 0.6 | 0.7 | 0.6 |
| Fibrinogen | g/L | 2.06 - 6.13 | 3.2 | 3 | 2.4 | 2.5 |

FIGURE 4D

| Laboratory Data Analyses | REFERENCE (units) | Values | PIG #4 (20/09/06) DAY 1 | PIG #4 (21/09/06) DAY 2 | PIG #4 (22/09/06) DAY 3 | PIG #4 (26/09/06) DAY 7 |
|---|---|---|---|---|---|---|
| CBC | | | | | | |
| WBCs | mil/mm$^3$ | 7 to 20 | 26700 | 15800 | 21300 | 29700 |
| RBCs | mil/mm$^3$ | 5 to 8 | 6.11 | 5.67 | 6.28 | 4.89 |
| Hg | g/dL | 6.9 to 12.7 | 11.1 | 10.4 | 11.6 | 9.3 |
| Hct | % | 15 – 37 | 33 | 30 | 34 | 27 |
| MCV | Fl | 50 – 68 | 54 | 54 | 54 | 56 |
| MCH | Pg | 17 – 23 | 18 | 18 | 19 | 19 |
| MCHC | g/dL | 30 – 36 | 34 | 34 | 35 | 34 |
| RDW | % | | 20 | 20 | 20 | 25 |
| WBC-diff | | | | | | |
| Polymorphs | % | 28 – 50 | 69 | 60 | 48 | 67 |
| Lymphocytes | % | 40 – 60 | 25 | 32 | 46 | 24 |
| Monocytes | % | 2 to 10 | 6 | 7 | 2 | 9 |
| Eosinophils | % | 0 - 10 | 0 | 0 | 4 | 0 |
| Platelets | mm$^3$ | 120k – 720k | 645000 | 564000 | 586000 | 676000 |
| Glucose | mg/dL | 65 – 150 | 100 | 65 | 75 | 70 |
| Lactic acid | mmole/L | 1.91 - 2.47 | 3.14 | 1.13 | 0.95 | 1.58 |
| BUN | mg/dL | 6 – 30 | 26 | 10 | 10 | 15 |
| Creatinine | mg/dL | 0.8 - 3.6 | 1 | 0.8 | 0.8 | 0.6 |
| Sodium | mmole/L | 135 – 150 | 141 | 139 | 138 | 142 |
| Potassium | mmole/L | 4.1 - 6.9 | 4.3 | 4.1 | 4.9 | 4.5 |
| Chloride | mmole/L | 94 – 113 | 99 | 100 | 99 | 98 |
| Carbon Dioxide | mmole/L | 22 – 46 | 28 | 34 | 30 | 34 |
| Calcium | mmole/L | 2.07 - 3.32 | 2.25 | 2.27 | 2.42 | 2.59 |
| Magnesium | mmole/L | 0.7 – 1.00 | 0.95 | 0.82 | 0.86 | 0.90 |
| Phosphate | mg/dL | 7.0 - 10.9 | 8.6 | 6.4 | 7.5 | 9.3 |
| Osmolality | mOsm/kg | 280 – 306 | 295 | 284 | 287 | 292 |
| SGOT (AST) | IU/L | 29 – 1140 | 98 | 58 | 34 | 24 |
| SGPT (ALT) | IU/L | 7 - 161 | 53 | 55 | 56 | 54 |
| LDH | IU/L | 286 -12,000 | 1083 | 977 | 933 | 586 |
| CPK | IU/L | 311- 16,700 | 3687 | 2677 | 1346 | 326 |
| Prothrombin | | | | | | |
| Pt | Sec | | 9.9 | 10.9 | 10.7 | 10.5 |
| Control | Sec | | 12 | 12 | 12 | 12 |
| INR (ISI) | (ratio) | 0.8 - 1.2 | 0.8 | 0.9 | 0.9 | 0.9 |
| aPTT | Sec | 17.8 - 23.3 | 22.5 | 20.5 | 18.5 | 17 |
| Control | Sec | | 30.5 | 29 | 30 | 30 |
| aPTT (ratio) | | | 0.7 | 0.7 | 0.6 | 0.6 |
| Fibrinogen | g/L | 2.06 - 6.13 | 3 | 3.2 | 2.7 | 2.8 |

FIGURE 4E

| Laboratory Data Analyses | REFERENCE (units) | Values | PIG #5 (28/09/06) DAY 1 | PIG #5 (29/09/06) DAY 2 | PIG #5 (30/09/06) DAY 3 | PIG #5 (4/10/06) DAY 7 |
|---|---|---|---|---|---|---|
| CBC | | | | | | |
| WBCs | mil/mm$^3$ | 7 to 20 | 21700 | 19700 | 20300 | 22700 |
| RBCs | mil/mm$^3$ | 5 to 8 | 6.35 | 5.7 | 5.58 | 6.23 |
| Hg | g/dL | 6.9 to 12.7 | 11.1 | 9.9 | 9.8 | 11 |
| Hct | % | 15 – 37 | 33 | 29 | 29 | 33 |
| MCV | Fl | 50 – 68 | 51 | 51 | 51 | 52 |
| MCH | Pg | 17 – 23 | 18 | 17 | 18 | 18 |
| MCHC | g/dL | 30 – 36 | 34 | 35 | 34 | 34 |
| RDW | % | | 21 | 20 | 21 | 21 |
| WBC-diff | | | | | | |
| Polymorphs | % | 28 – 50 | 53 | 45 | 42 | 52 |
| Lymphocytes | % | 40 – 60 | 43 | 49 | 52 | 41 |
| Monocytes | % | 2 to 10 | 3 | 3 | 3 | 5 |
| Eosinophils | % | 0 - 10 | 1 | 1 | 2 | 1 |
| Platelets | mm$^3$ | 120k - 720k | 531000 | 456000 | 479000 | 513000 |
| Glucose | mg/dL | 65 – 150 | 171 | 97 | 84 | 79 |
| Lactic acid | mmole/L | 1.91 - 2.47 | 4.96 | 0.7 | 1.3 | 3.21 |
| BUN | mg/dL | 6 – 30 | 29 | 23 | 21 | 17 |
| Creatinine | mg/dL | 0.8 - 3.6 | 1 | 0.8 | 0.7 | 0.9 |
| Sodium | mmole/L | 135 - 150 | 142 | 144 | 150 | 142 |
| Potassium | mmole/L | 4.1 - 6.9 | 4.6 | 4.7 | 4.6 | 4.6 |
| Chloride | mmole/L | 94 – 113 | 99 | 104 | 107 | 98 |
| Carbon Dioxide | mmole/L | 22 – 46 | 35 | 30 | 31 | 35 |
| Calcium | mmole/L | 2.07 - 3.32 | 2.45 | 2.52 | 2.54 | 2.59 |
| Magnesium | mmole/L | 0.7 - 1.00 | 1.07 | 1.07 | 1.03 | 1.15 |
| Phosphate | mg/dL | 7 - 10.9 | 7.9 | 8.2 | 7.7 | 9.4 |
| Osmolality | mOsm/kg | 280 - 306 | 305 | 304 | 310 | 297 |
| SGOT (AST) | IU/L | 29 - 1140 | 45 | 34 | 38 | 23 |
| SGPT (ALT) | IU/L | 7 - 161 | 57 | 56 | 58 | 45 |
| LDH | IU/L | 286 -12,000 | 702 | 641 | 601 | 498 |
| CPK | IU/L | 311- 16,700 | 2719 | 1916 | 1606 | 505 |
| Prothrombin | | | | | | |
| Pt | Sec | | 11.2 | 10.9 | 11 | 11.4 |
| Control | Sec | | 12 | 12 | 12 | 12 |
| INR (ISI) | (ratio) | 0.8 - 1.2 | 0.9 | 0.9 | 0.9 | 1 |
| aPTT | Sec | 17.8 - 23.3 | 15.5 | 16.5 | 18 | 17.5 |
| Control | Sec | | 30.5 | 29.5 | 30 | 30.5 |
| aPTT (ratio) | | | 0.5 | 0.6 | 0.6 | 0.6 |
| Fibrinogen | g/L | 2.06 - 6.13 | 2.9 | 2.6 | 2.4 | 2.3 |

FIGURE 4F

| Laboratory Data Analyses | REFERENCE (units) | Values | PIG #6 (19/10/06) DAY 1 | PIG #6 (20/10/06) DAY 2 | PIG #6 (21/10/06) DAY 3 | PIG #6 (25/10/06) DAY 7 |
|---|---|---|---|---|---|---|
| CBC | | | | | | |
| WBCs | mil/mm$^3$ | 7 to 20 | 21400 | 21100 | 20800 | 17000 |
| RBCs | mil/mm$^3$ | 5 to 8 | 6.05 | 5.49 | 5.77 | 5.36 |
| Hg | g/dL | 6.9 to 12.7 | 11.7 | 10.6 | 11.1 | 10.2 |
| Hct | % | 15 – 37 | 34 | 31 | 32 | 30 |
| MCV | Fl | 50 – 68 | 57 | 57 | 56 | 56 |
| MCH | Pg | 17 – 23 | 19 | 19 | 19 | 19 |
| MCHC | g/dL | 30 – 36 | 34 | 34 | 35 | 34 |
| RDW | % | | 16 | 16 | 16 | 16 |
| WBC-diff | | | | | | |
| Polymorphs | % | 28 – 50 | 51 | 66 | 68 | 54 |
| Lymphocytes | % | 40 – 60 | 47 | 31 | 32 | 36 |
| Monocytes | % | 2 to 10 | 2 | 3 | 0 | 6 |
| Eosinophils | % | 0 - 10 | 0 | 0 | 0 | 1 |
| Platelets | Mm$^3$ | 120k - 720k | 601000 | 595000 | 616000 | 711000 |
| Glucose | mg/dL | 65 – 150 | 74 | 91 | 105 | 108 |
| Lactic acid | mmole/L | 1.91 - 2.47 | 1.06 | 0.89 | 1.17 | 1.3 |
| BUN | mg/dL | 6 – 30 | 10 | 14 | 9 | 16 |
| Creatinine | mg/dL | 0.8 - 3.6 | 0.7 | 0.7 | 0.8 | 0.5 |
| Sodium | mmole/L | 135 – 150 | 138 | 139 | 143 | 145 |
| Potassium | mmole/L | 4.1 - 6.9 | 3.8 | 4.4 | 4 | 4.5 |
| Chloride | mmole/L | 94 – 113 | 98 | 99 | 103 | 100 |
| Carbon Dioxide | mmole/L | 22 – 46 | 31 | 32 | 31 | 40 |
| Calcium | mmole/L | 2.07 - 3.32 | 2.40 | 2.40 | 2.37 | 2.89 |
| Magnesium | mmole/L | 0.7 - 1.00 | 0.90 | 0.86 | 0.70 | 0.90 |
| Phosphate | mg/dL | 7.0 - 10.9 | 8.4 | 7.3 | 7.4 | 8.8 |
| Osmolality | mOsm/kg | 280 – 306 | 300 | 301 | 296 | 309 |
| SGOT (AST) | IU/L | 29 – 1140 | 103 | 111 | 50 | 29 |
| SGPT (ALT) | IU/L | 7 - 161 | 43 | 54 | 56 | 49 |
| LDH | IU/L | 286 -12,000 | 867 | 939 | 738 | 618 |
| CPK | IU/L | 311- 16,700 | 11870 | 11528 | 4305 | 346 |
| Prothrombin | | | | | | |
| Pt | Sec | | 15.5 | 16.2 | 13 | 11.6 |
| Control | Sec | | 12 | 12 | 12 | 12 |
| INR (ISI) | (ratio) | 0.8 – 1.2 | 1.3 | 1.4 | 1.1 | 1 |
| aPTT | Sec | 17.8 - 23.3 | 21 | 23.5 | 23 | 23.5 |
| Control | Sec | | 30.5 | 29 | 29.5 | 29 |
| aPTT (ratio) | | | 0.7 | 0.8 | 0.8 | 0.8 |
| Fibrinogen | g/L | 2.06 - 6.13 | 3.2 | 2.7 | 2.2 | 1.6 |

FIGURE 4G

Summary Data Table - Reference and Average Values of Blood Data Analysis in a Normovolemic Pig Model

| Analysis | Reference Values | Average Values over Experimental Period | | | |
|---|---|---|---|---|---|
| | | Day 1 | Day 2 | Day 3 | Day 7 |
| *Blood & Cell Profile* | | | | | |
| RBC's | 5 – 8 mil/mm$^3$ | 6.286 | 5.908 | 6.004 | 5.796 |
| Hg | 6.9 - 12.7 g/Dl | 11.26 | 10.58 | 10.78 | 10.46 |
| Hct | 15 – 37 % | 32.8 | 30.6 | 31.6 | 30.6 |
| WBC's | 7 – 20 mil/mm$^3$ | 23000 | 17540 | 20120 | 24960 |
| Lymphocytes | 40 – 60 % | 45.4 | 51.0 | 51.0 | 34.4 |
| Platelets | 120,000 – 720,000 mm$^3$ | 470600 | 518000 | 529200 | 560000 |
| Pt [INR] | 0.8 - 1.2 | 0.98 | 1.02 | 0.96 | 0.96 |
| aPTT | 17.8 - 23.3 sec | 18.6 | 20.0 | 19.8 | 19.3 |
| Fibrinogen | 2.06 - 6.13 g/L | 3.10 | 2.96 | 2.52 | 2.26 |
| *Electrolytes* | | | | | |
| Sodium | 135 – 150 mmole/L | 140.4 | 140.8 | 143.8 | 141.4 |
| Potassium | 4.1 – 6.9 mmole/L | 4.18 | 4.32 | 4.46 | 4.42 |
| Calcium | 2.07 - 3.32 mmole/L | 2.40 | 2.43 | 2.48 | 2.62 |
| Magnesium | 0.70 - 1.00 mmole/L | 0.93 | 0.90 | 0.89 | 0.95 |
| Hydrogen Carbonate | 22 – 46 mmole/L | 30.8 | 30.4 | 30.2 | 33.2 |
| Osmolality | 280 - 306 mOsm/kg | 295.4 | 295.8 | 300.0 | 295.6 |
| *Metabolites* | | | | | |
| Glucose | 65 – 150 mg/Dl | 102.6 | 89 | 90.2 | 86.2 |
| Lactic acid | 1.91 - 2.47 mmole/L | 2.09 | 0.80 | 1.24 | 2.31 |
| BUN | 6 – 30 mg/dL | 18.0 | 14.8 | 13.8 | 14.8 |
| Creatinine | 0.8 – 3.6 mg/dL | 0.82 | 0.78 | 0.8 | 0.68 |
| *Enzymes* | | | | | |
| LDH | 286 -12,000 IU/L | 794 | 791.4 | 716.2 | 580.2 |
| SGOT (AST) | 29 – 1140 IU/L | 73.4 | 61.8 | 38.8 | 27.2 |
| SGPT (ALT) | 7 - 161 IU/L | 43.8 | 51.2 | 51.8 | 55.8 |
| CPK | 311- 16,700 IU/L | 5023.8 | 4642 | 2441.2 | 434.4 |

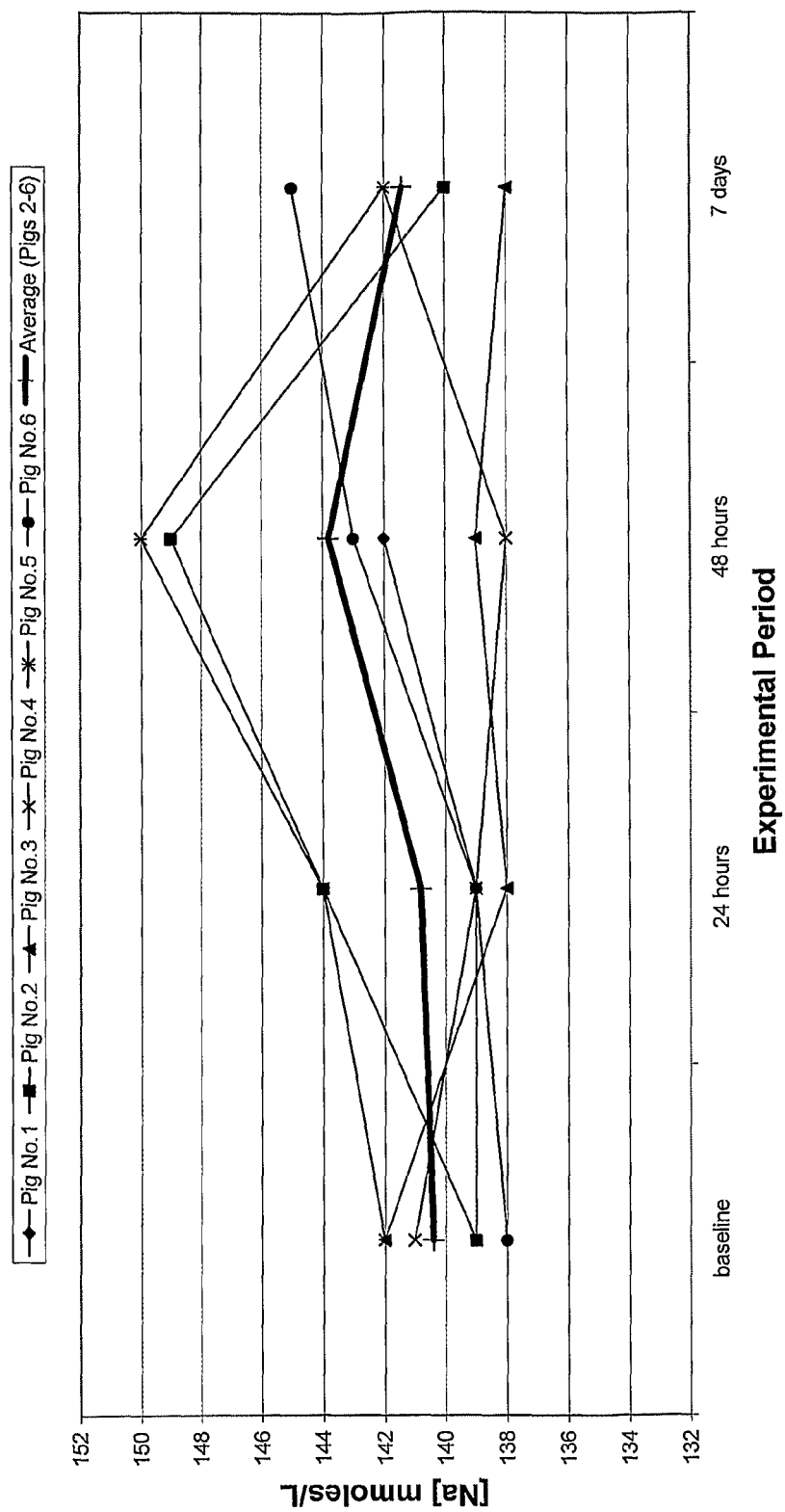

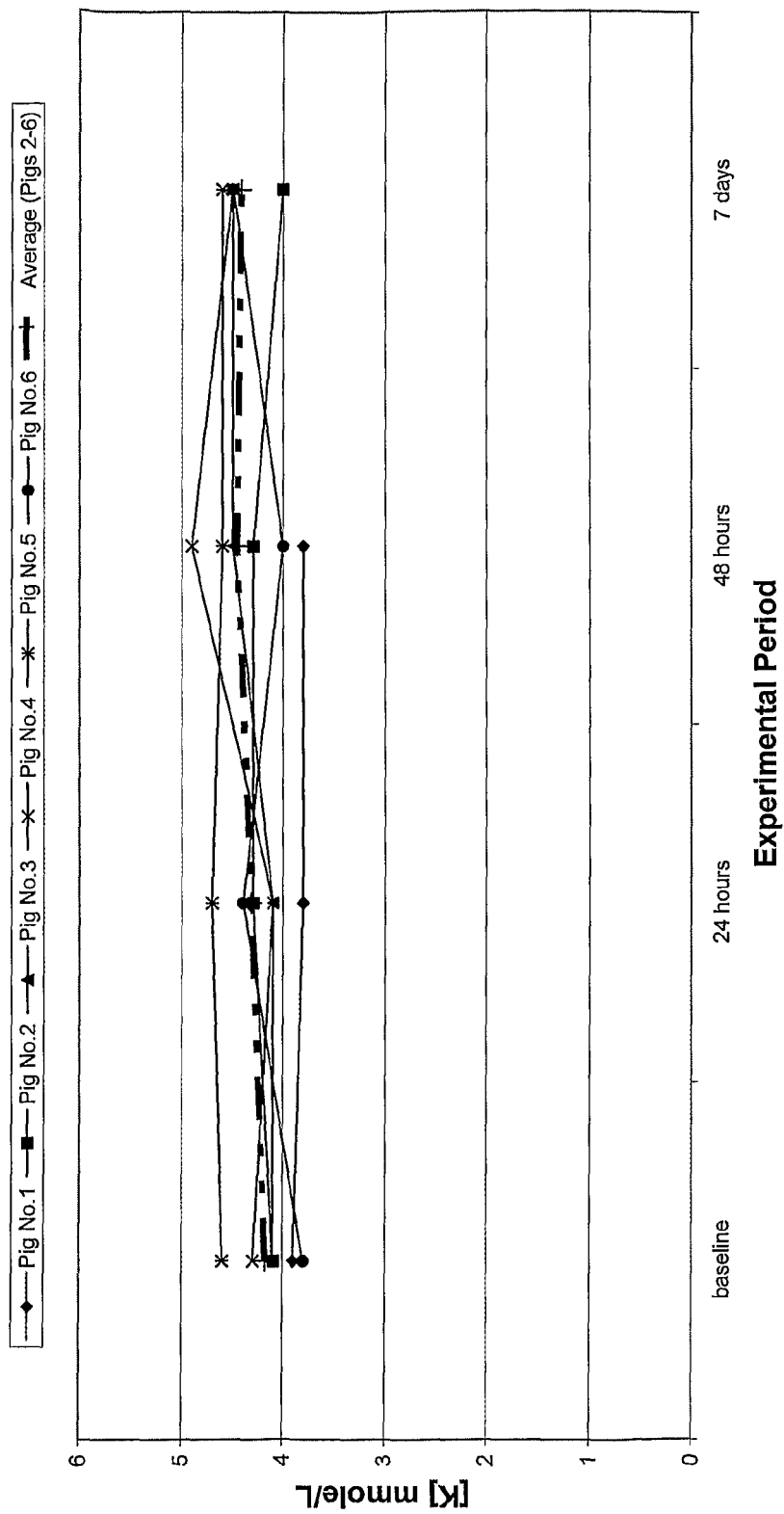
Fig. 5B  Analysis of Potassium Ion Levels
[Range value: 4.1 - 6.9 mmole/L]

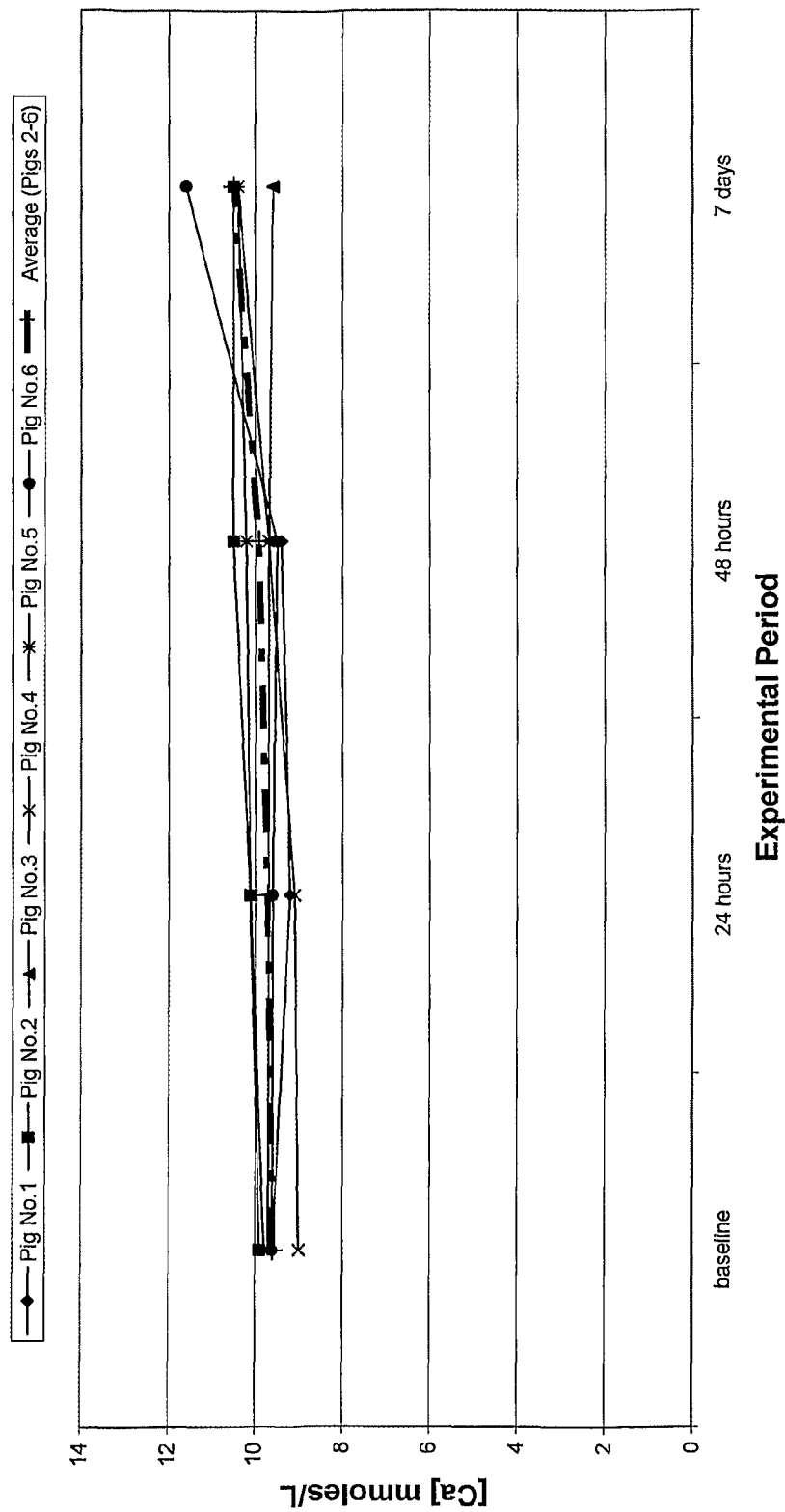
Fig. 5C Analysis of Calcium Ion Levels
[Range value: 8.3 - 13.3 mg/dL]

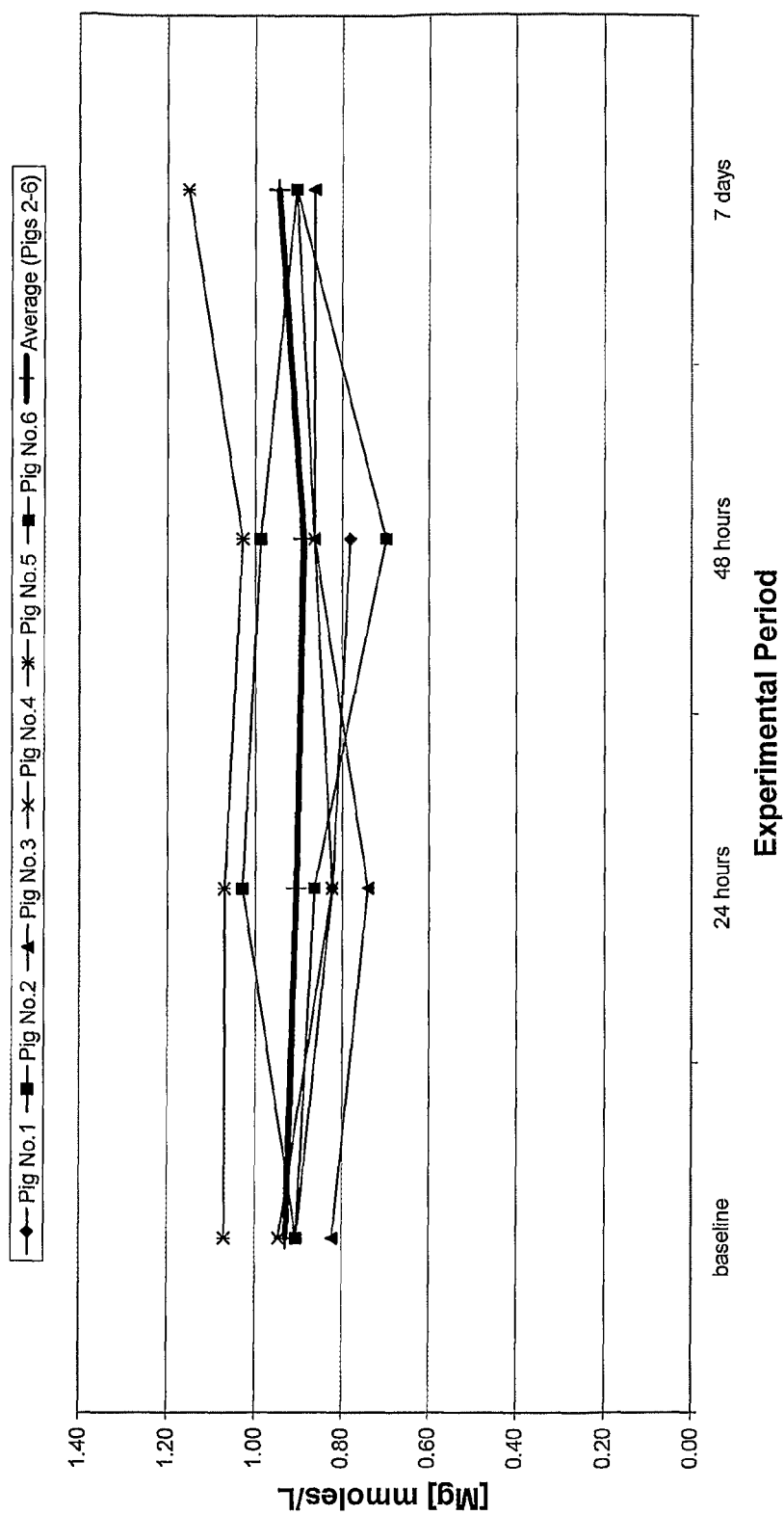
Fig. 5D Analysis of Magnesium Ion Levels
[Range value: 0.70 - 1.00 mmoles/L]

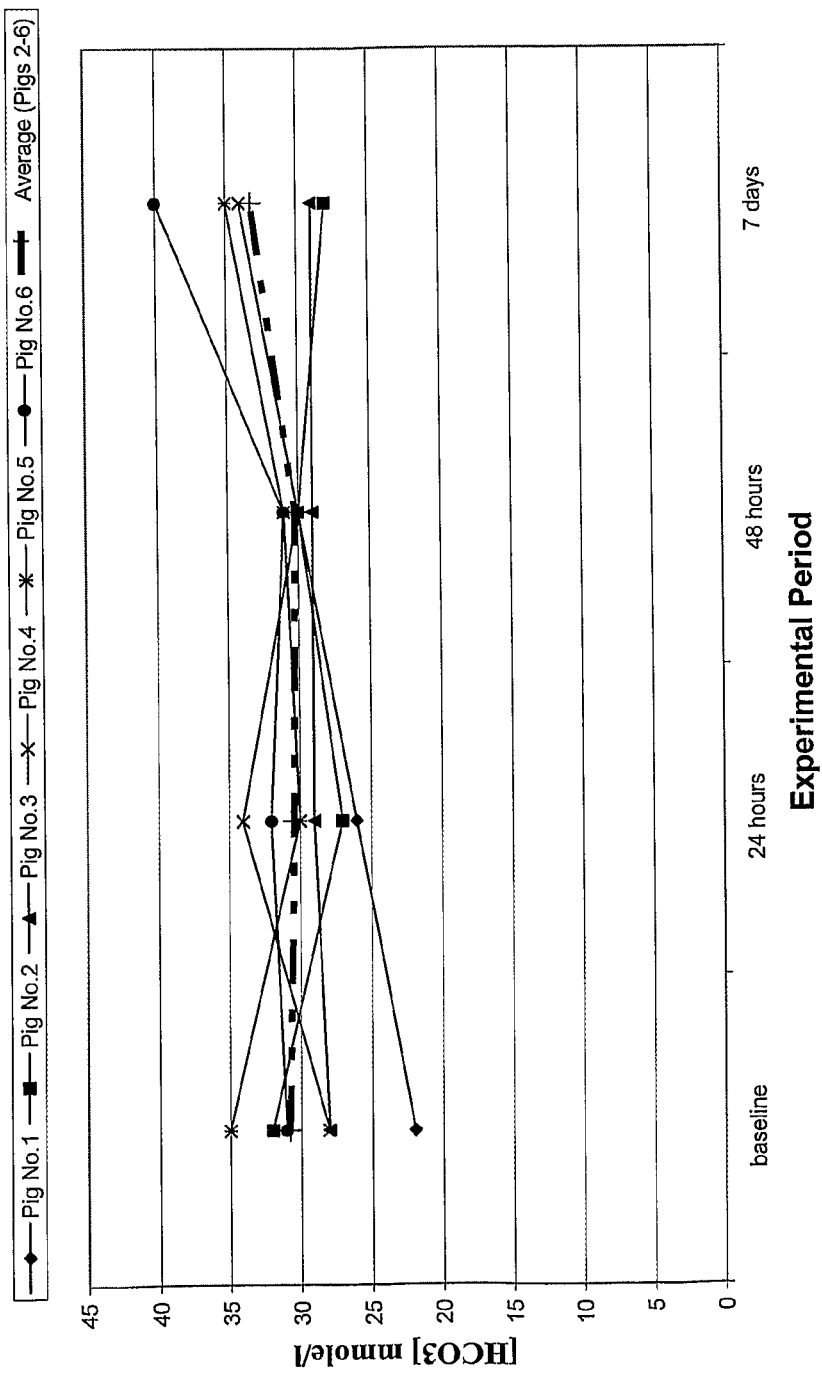

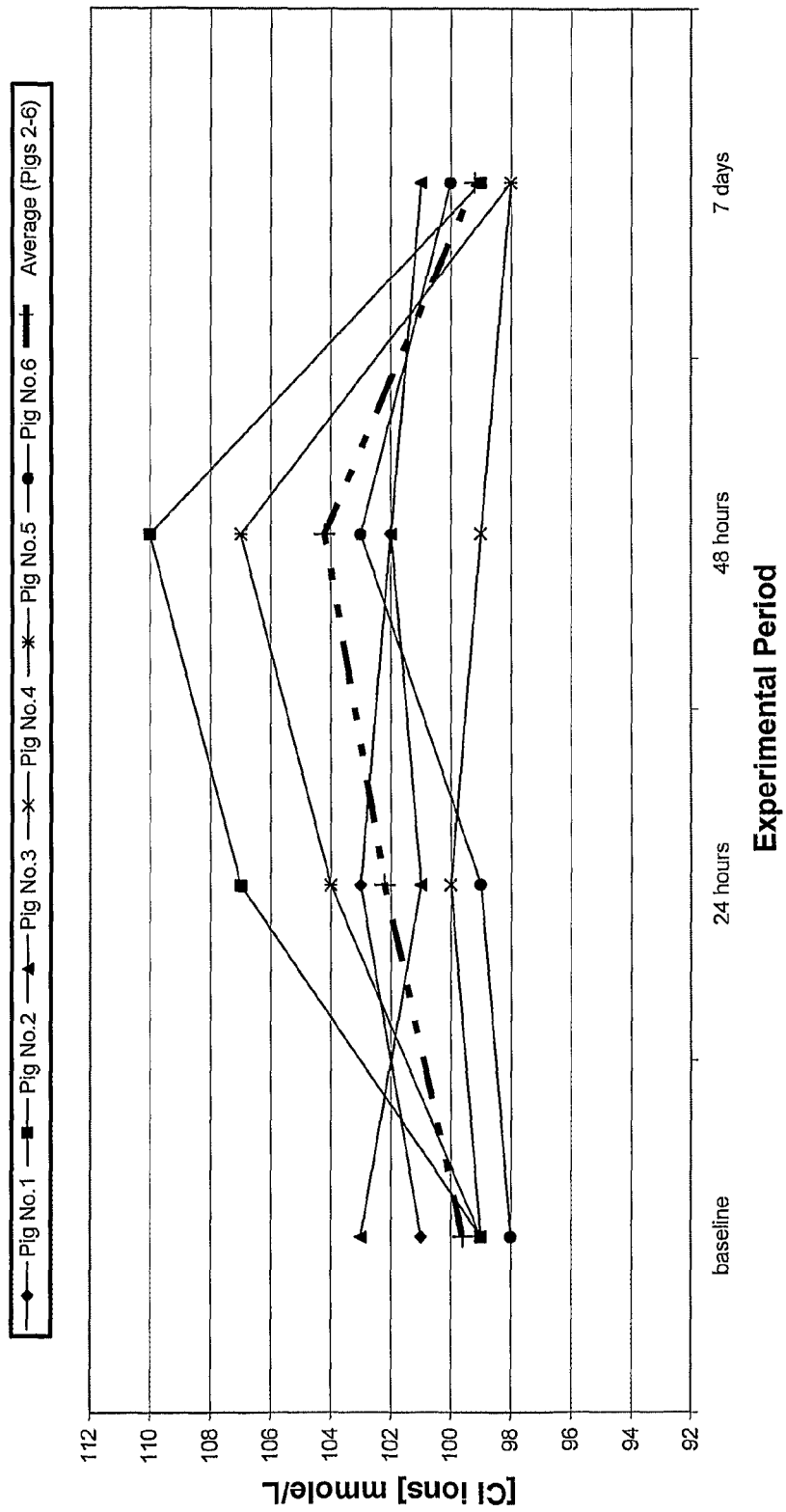
Fig. 5F Analysis of Chloride Ion Levels
[Range value: 94 - 113 mmole/L]

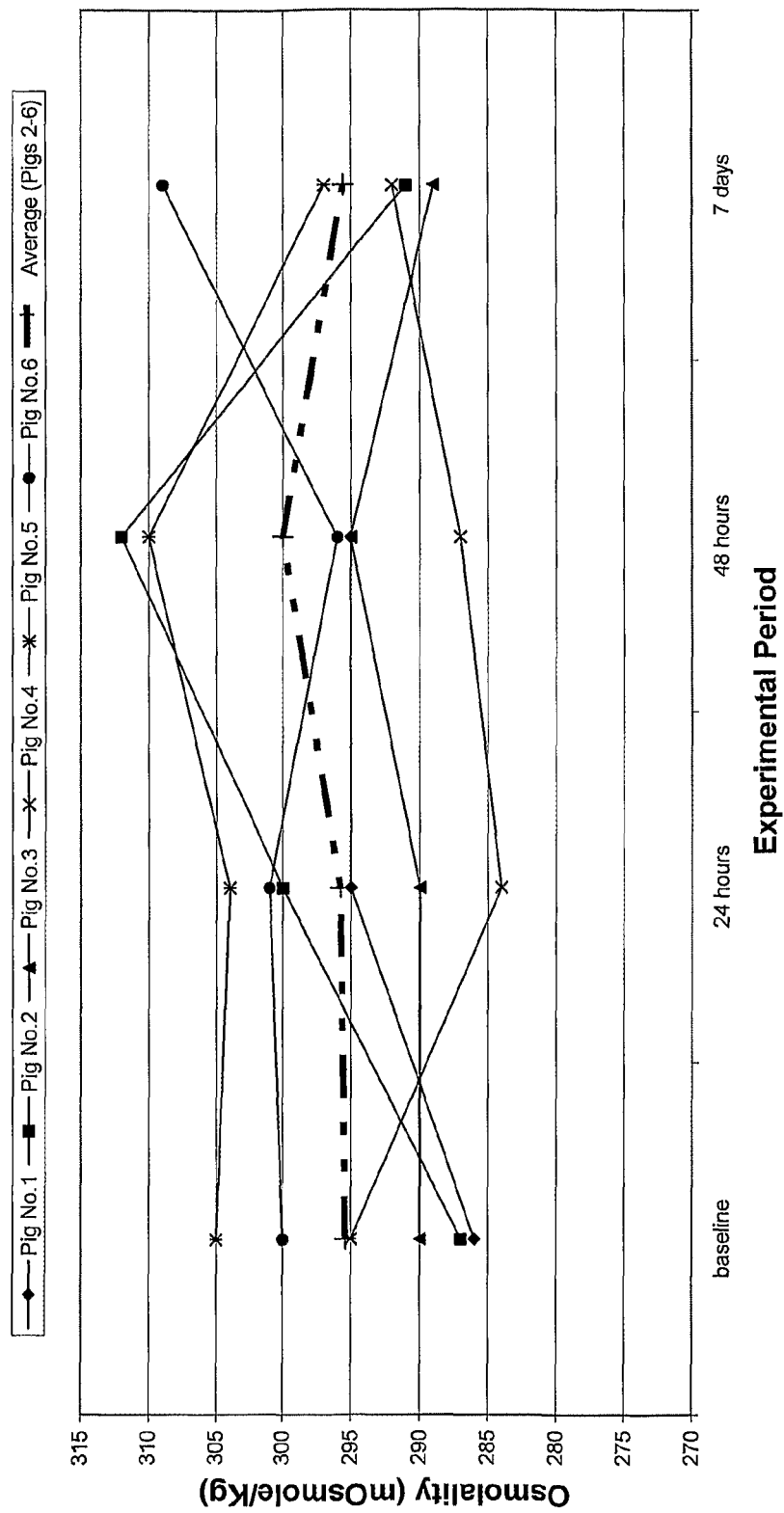

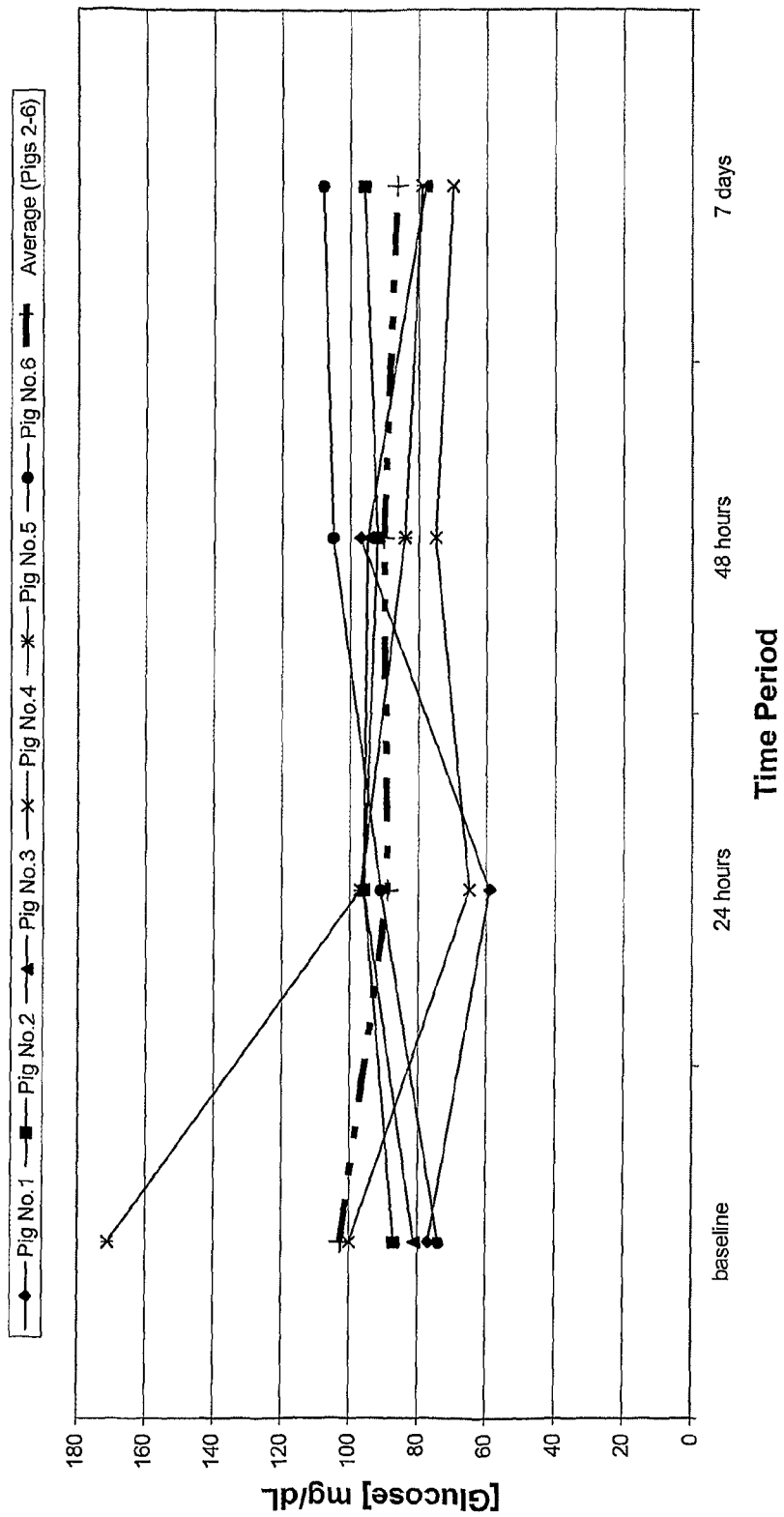

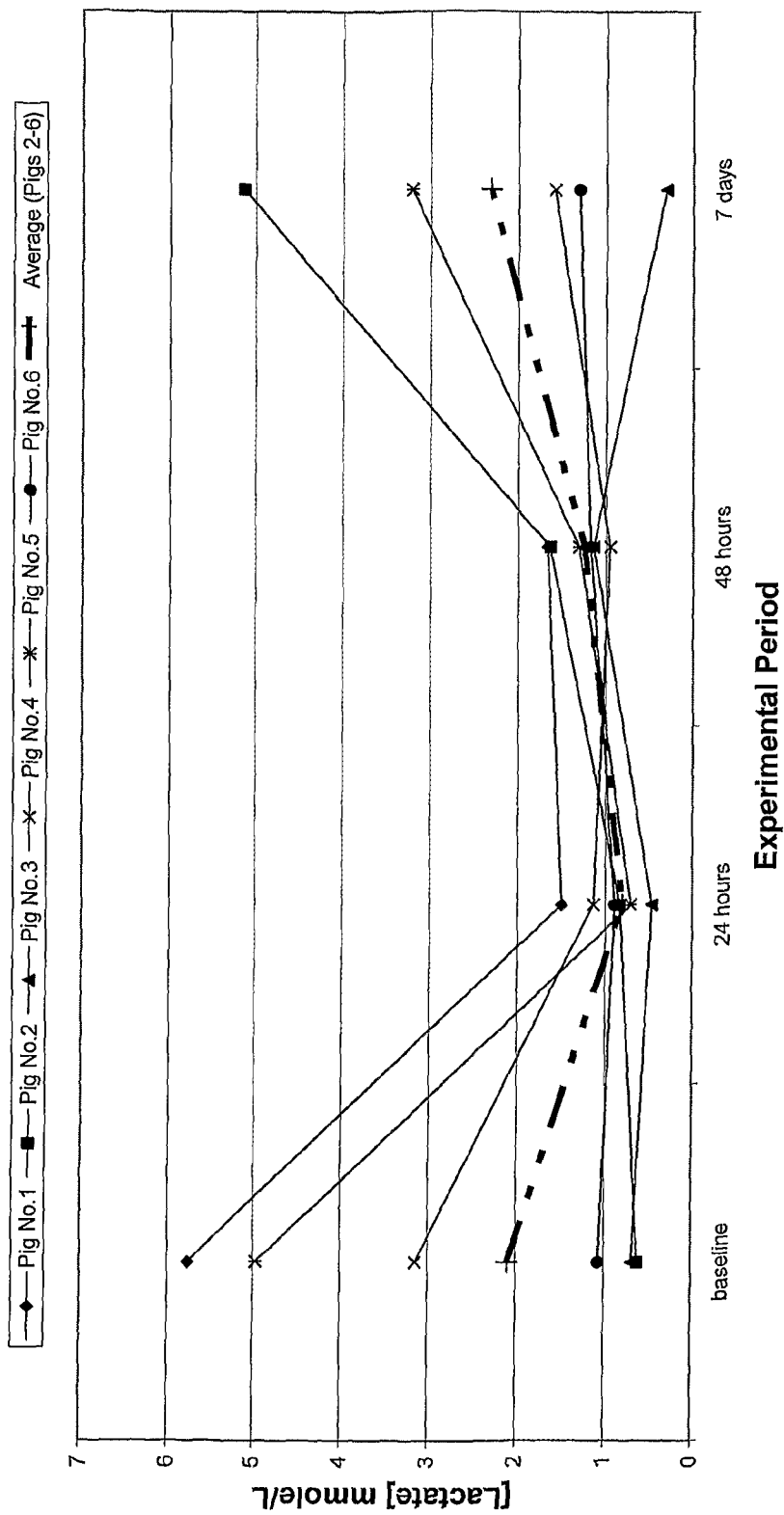

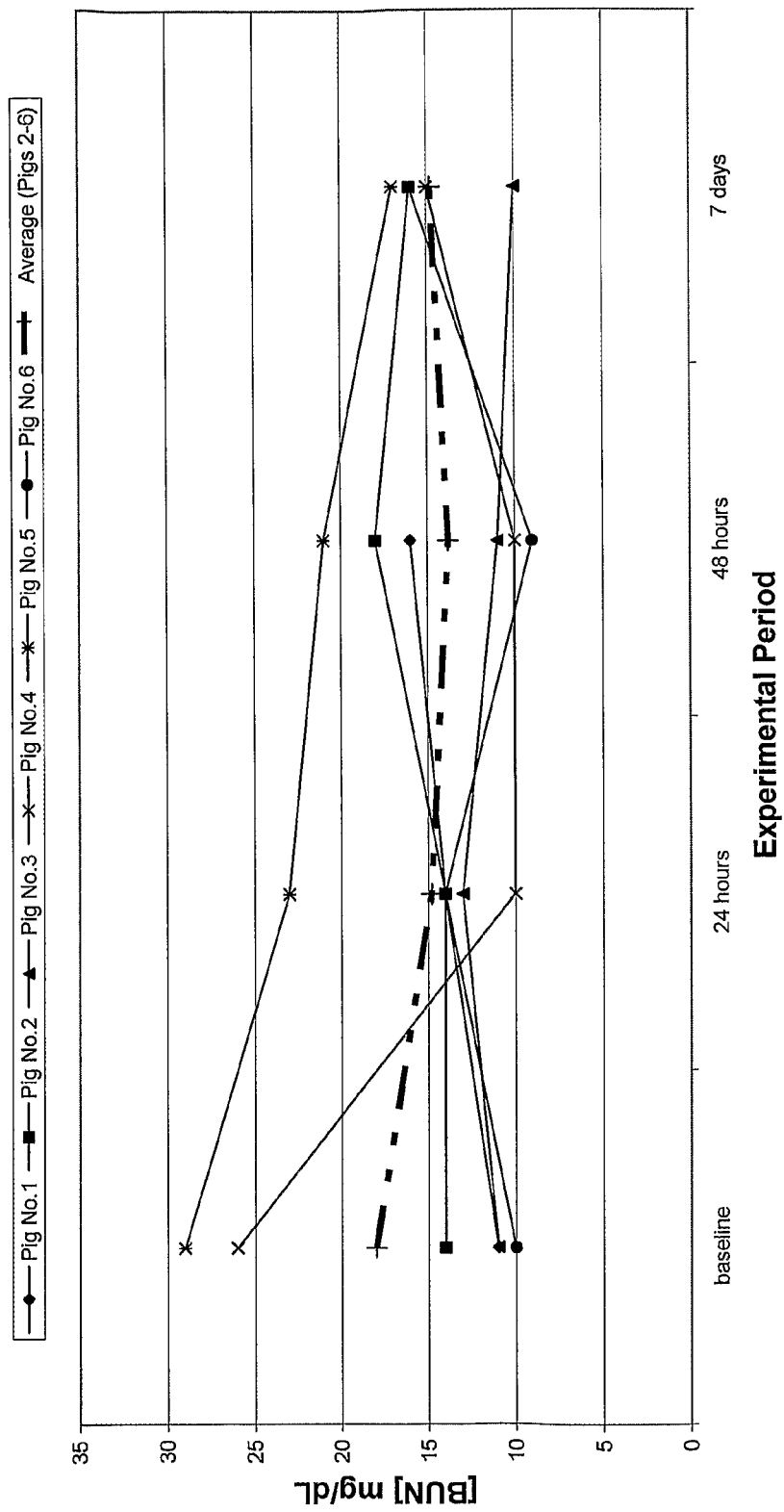
Fig. 6C  Analysis of Blood Urea Nitrogen (BUN) Levels
[Range value: 6 - 30 mg/dL]

Fig. 6D  Analysis of Creatinine Levels
[Range value: 0.8 - 3.6 IU/L]

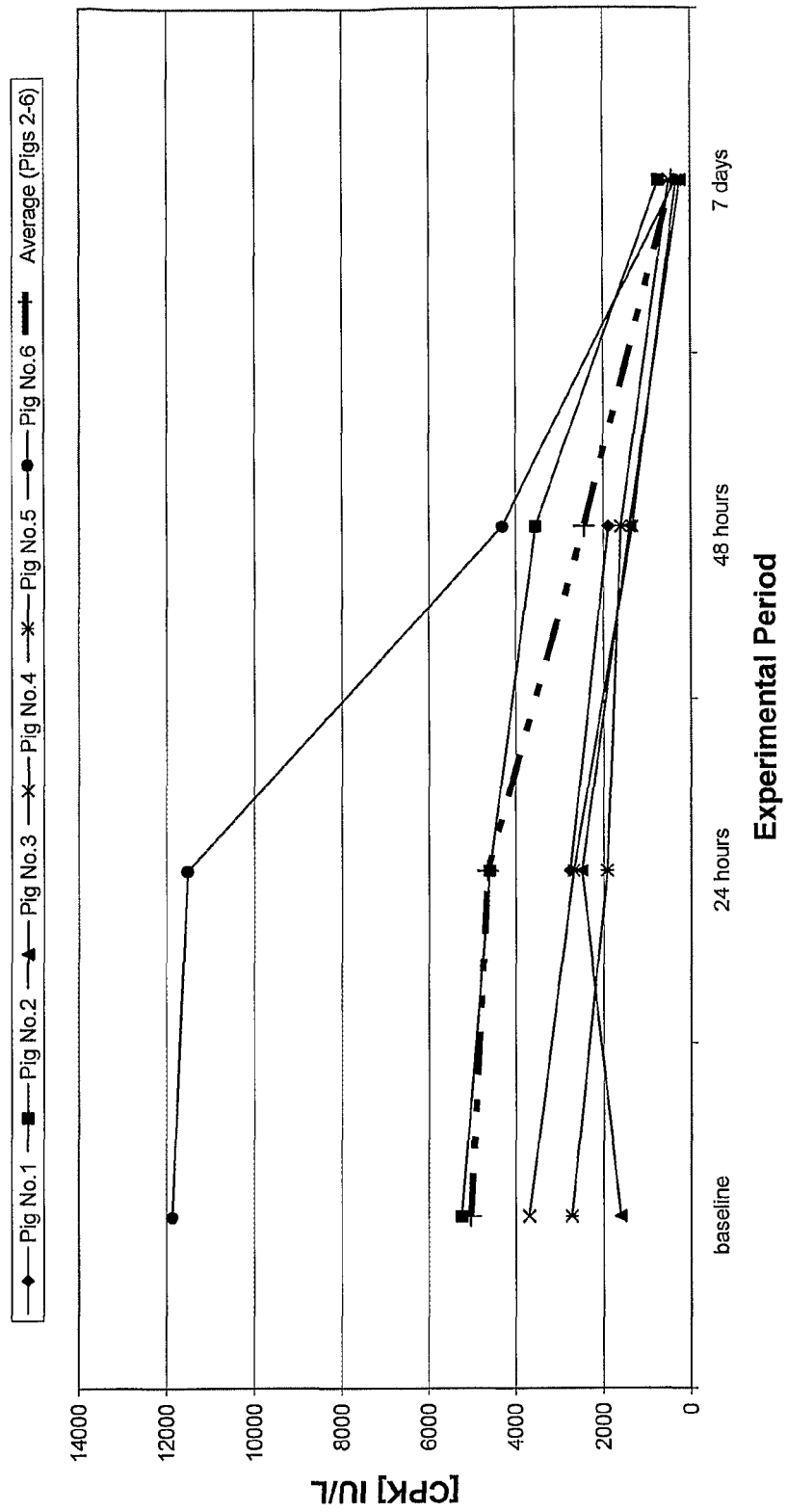
Fig. 7A  Analysis of Creatine Phosphokinase (CPK) Levels
[Range Value: 311- 16,700 IU/L]

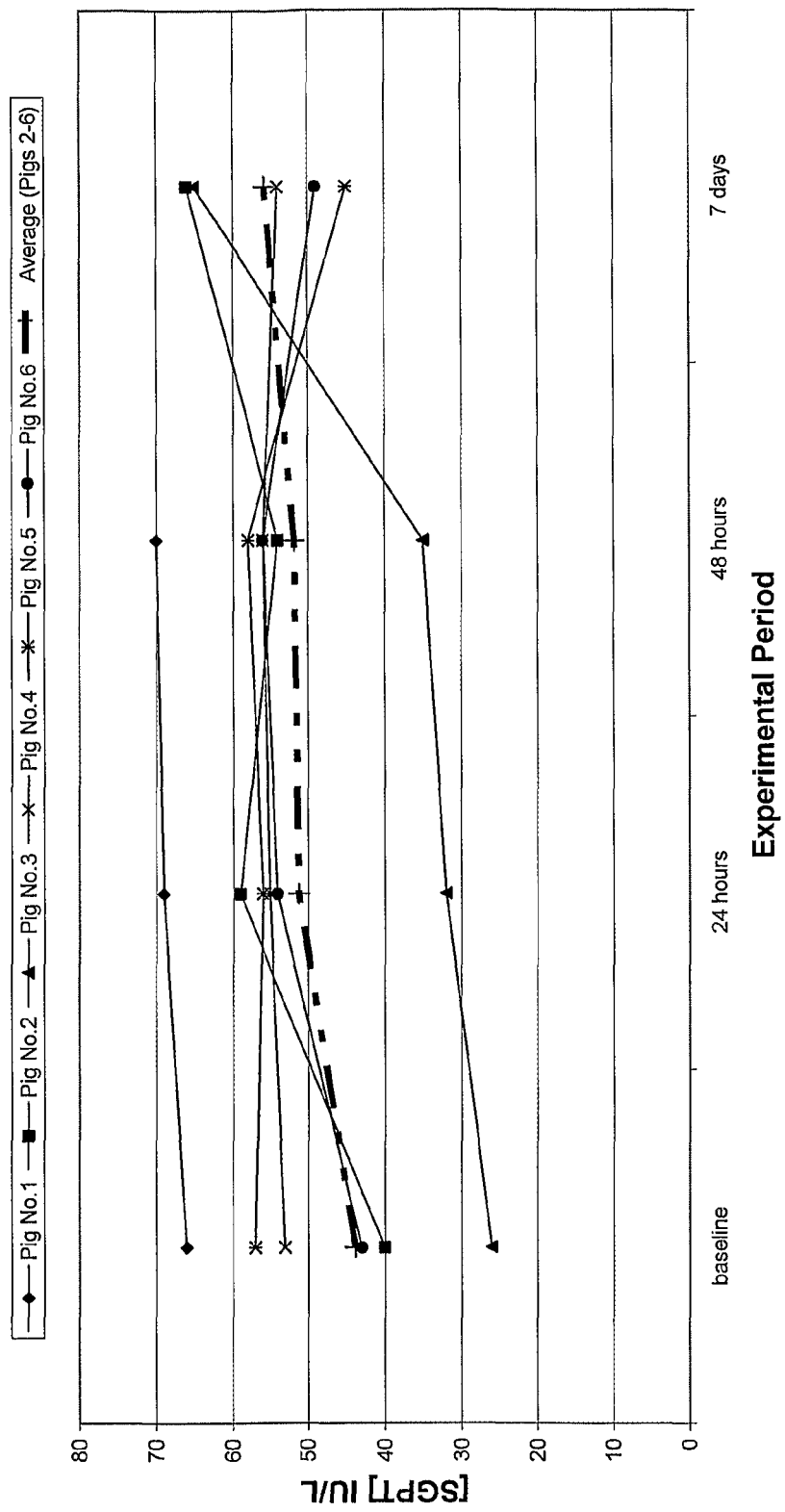
Fig. 7 B   Analysis of SGPT (ALT) Levels
[Range value: 7 - 161 IU/L]

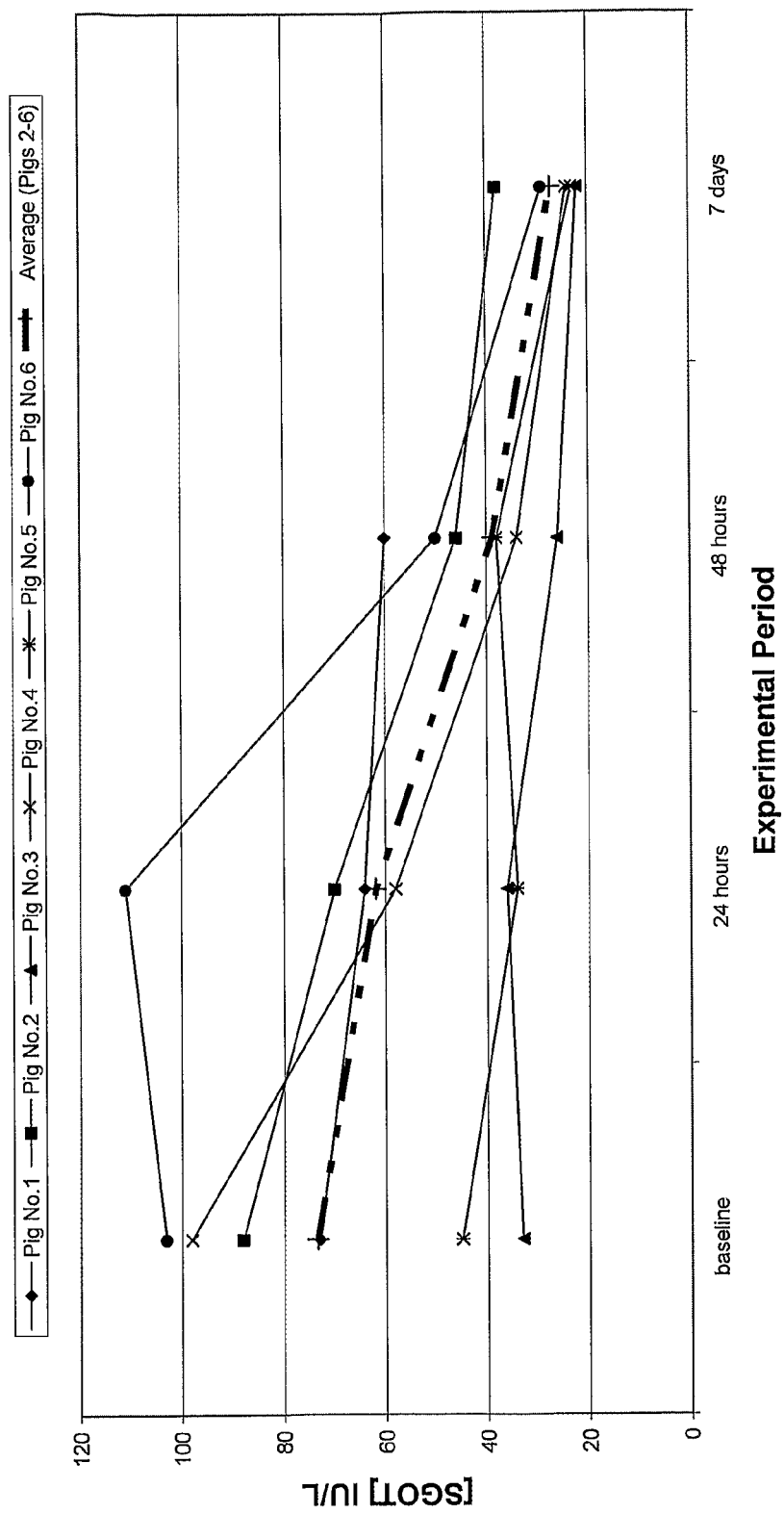

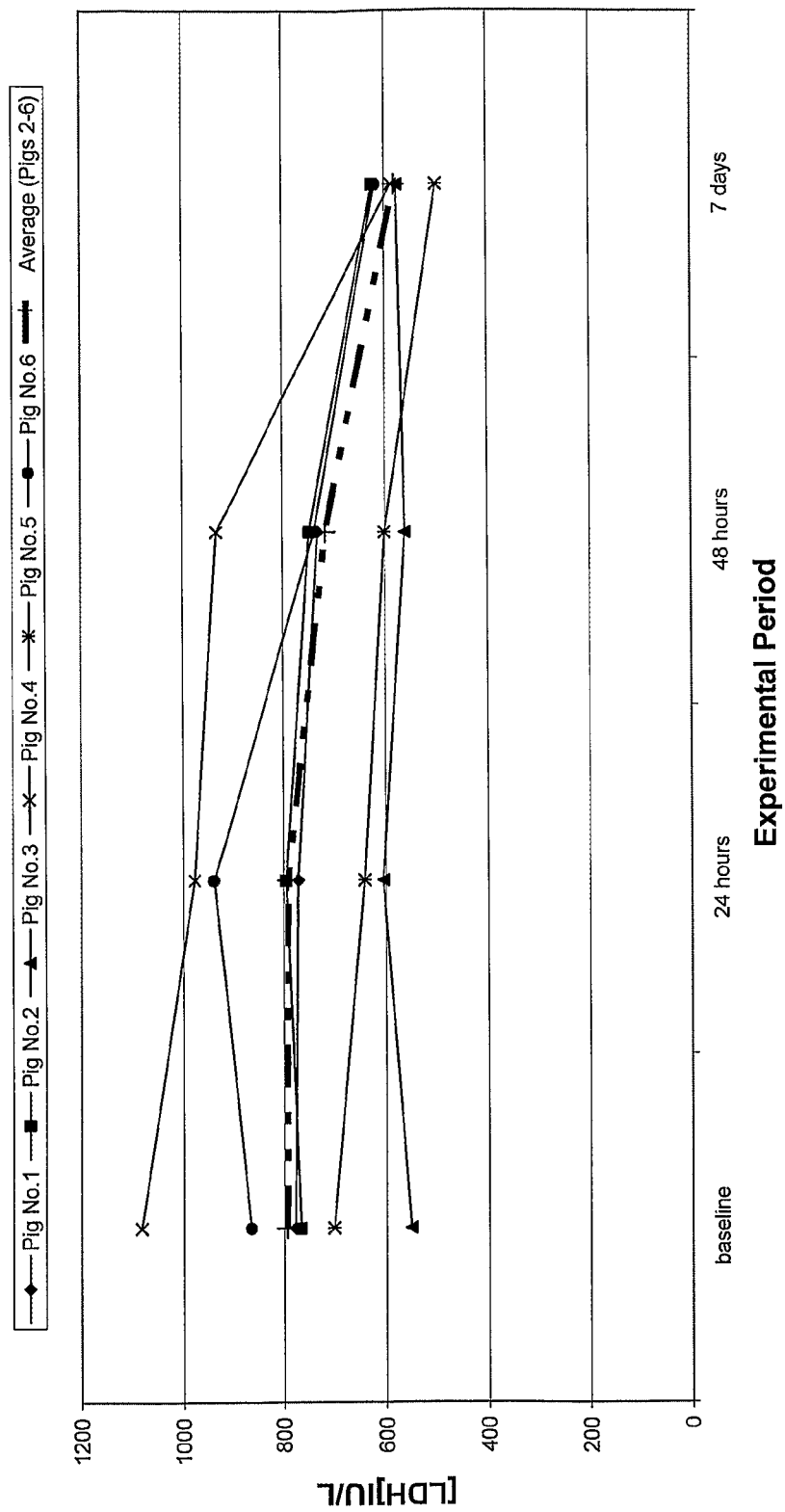

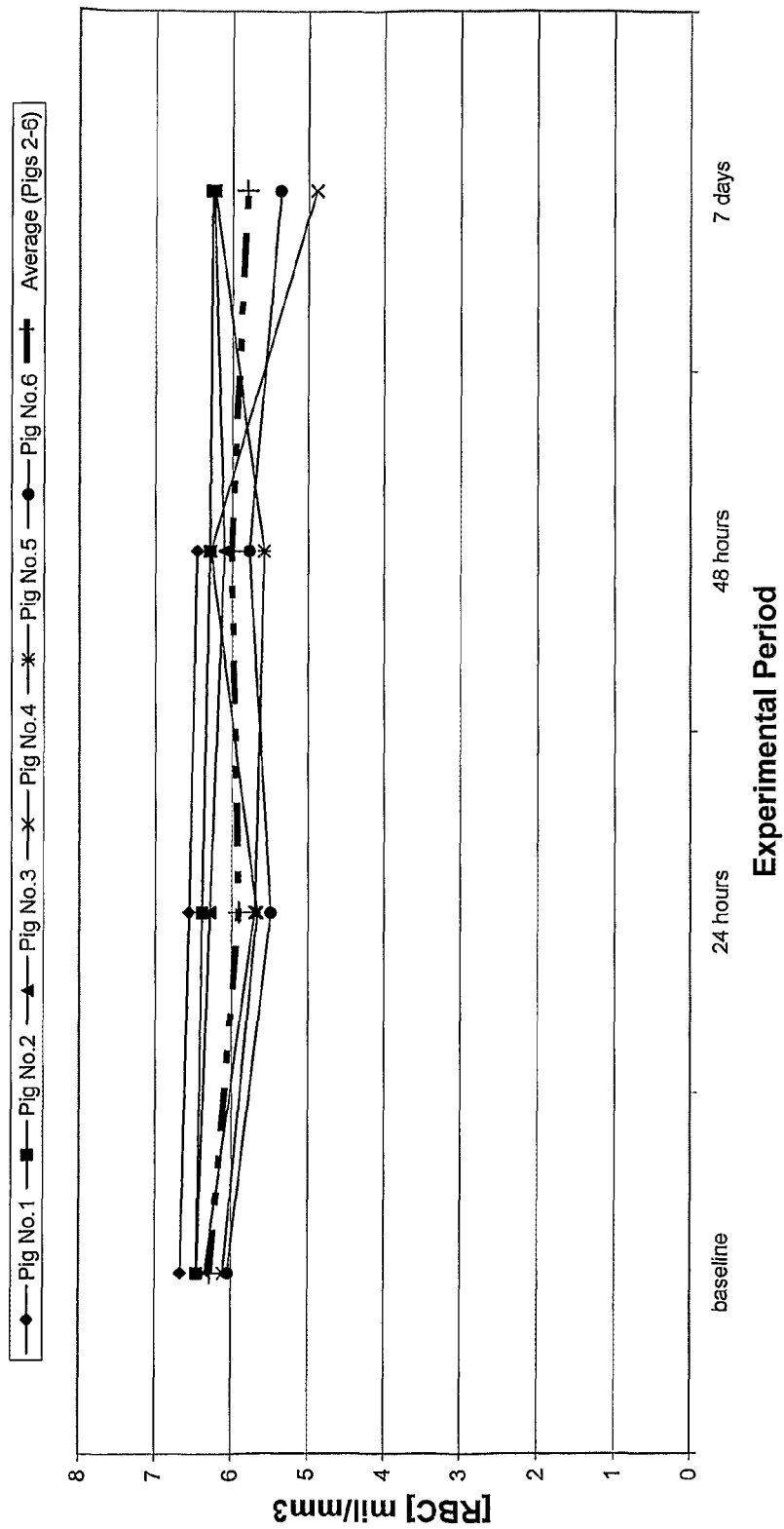
Fig. 8A Analysis of RBC Count
[Range value: 5 - 8 x 10⁶/mm³]

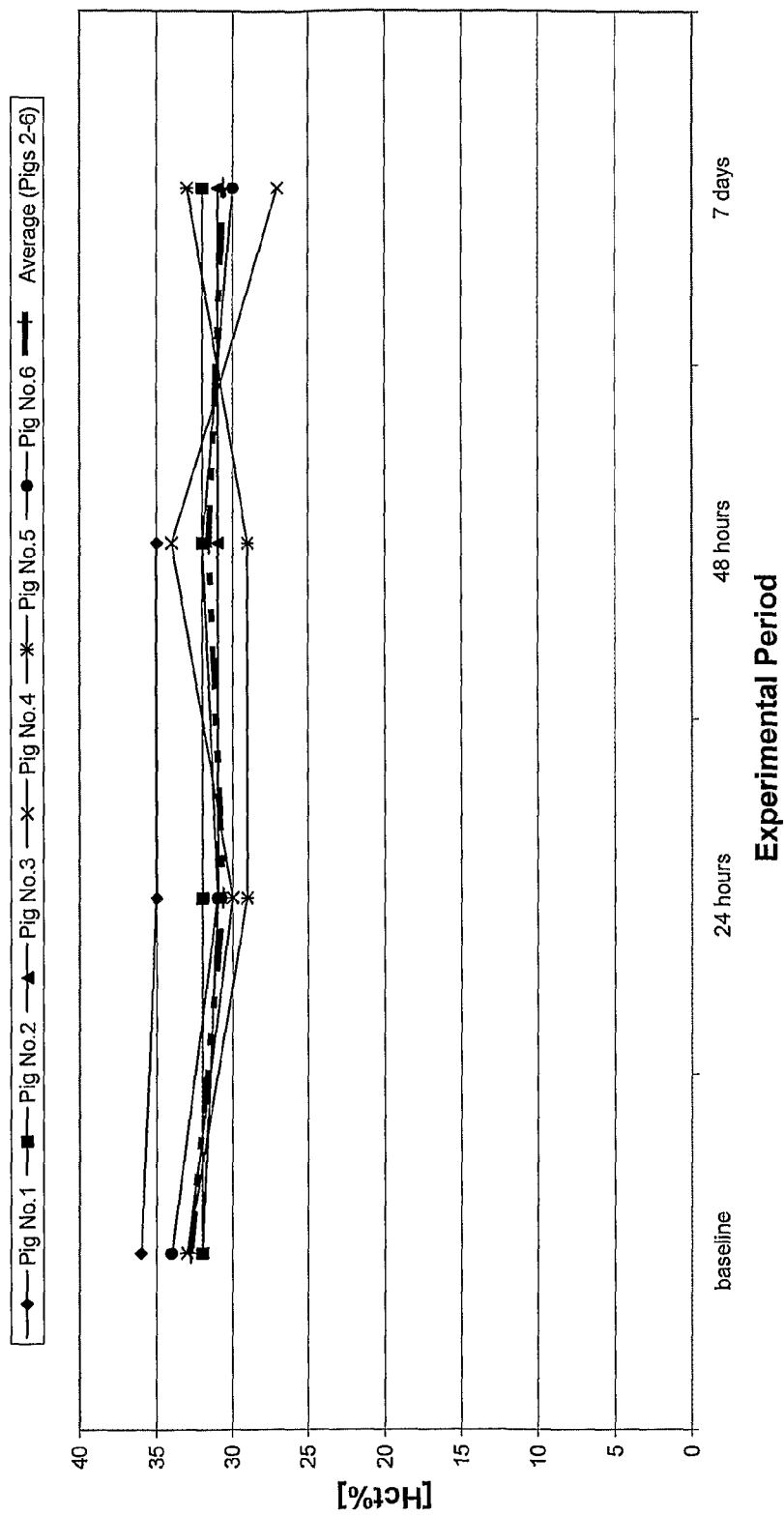

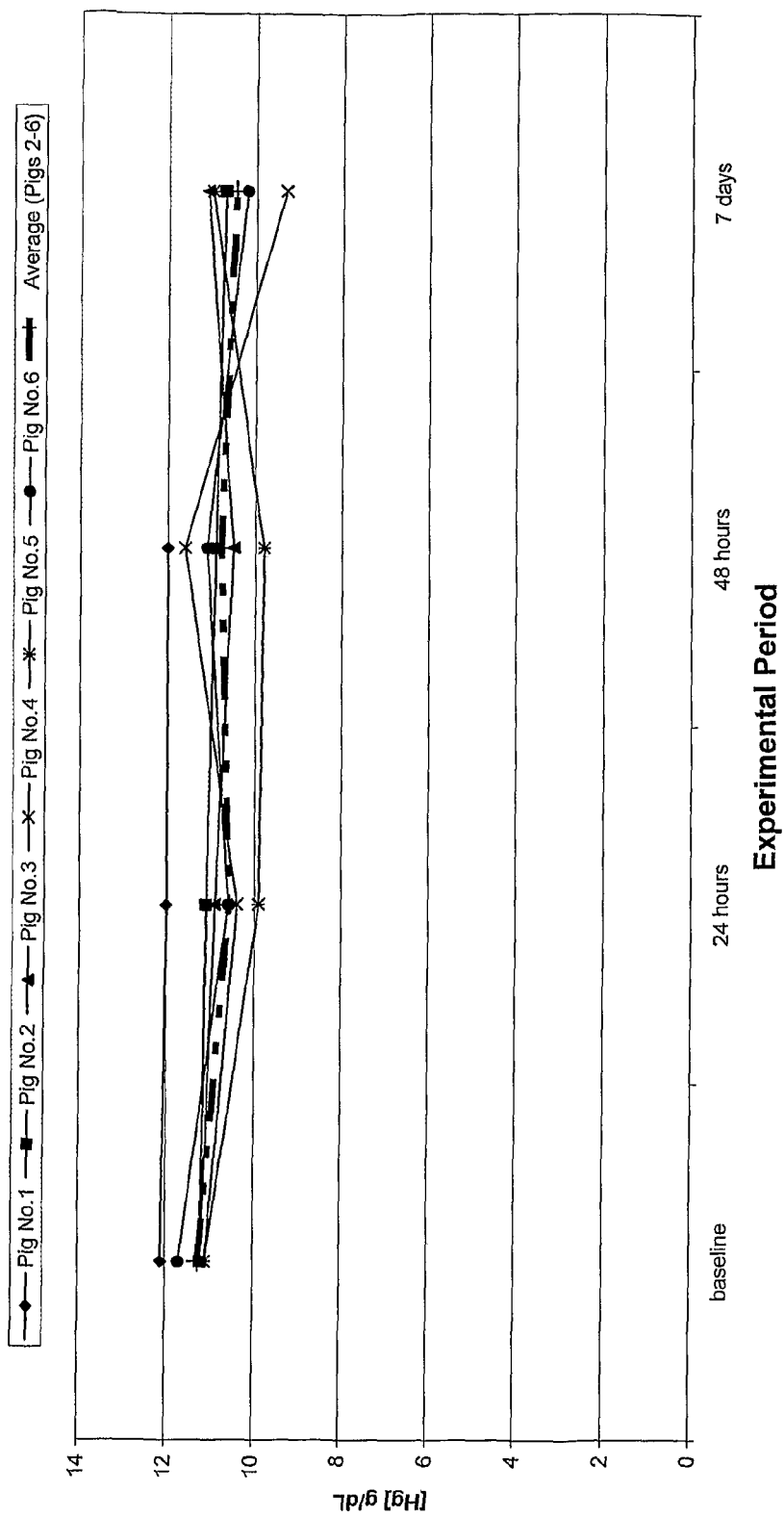

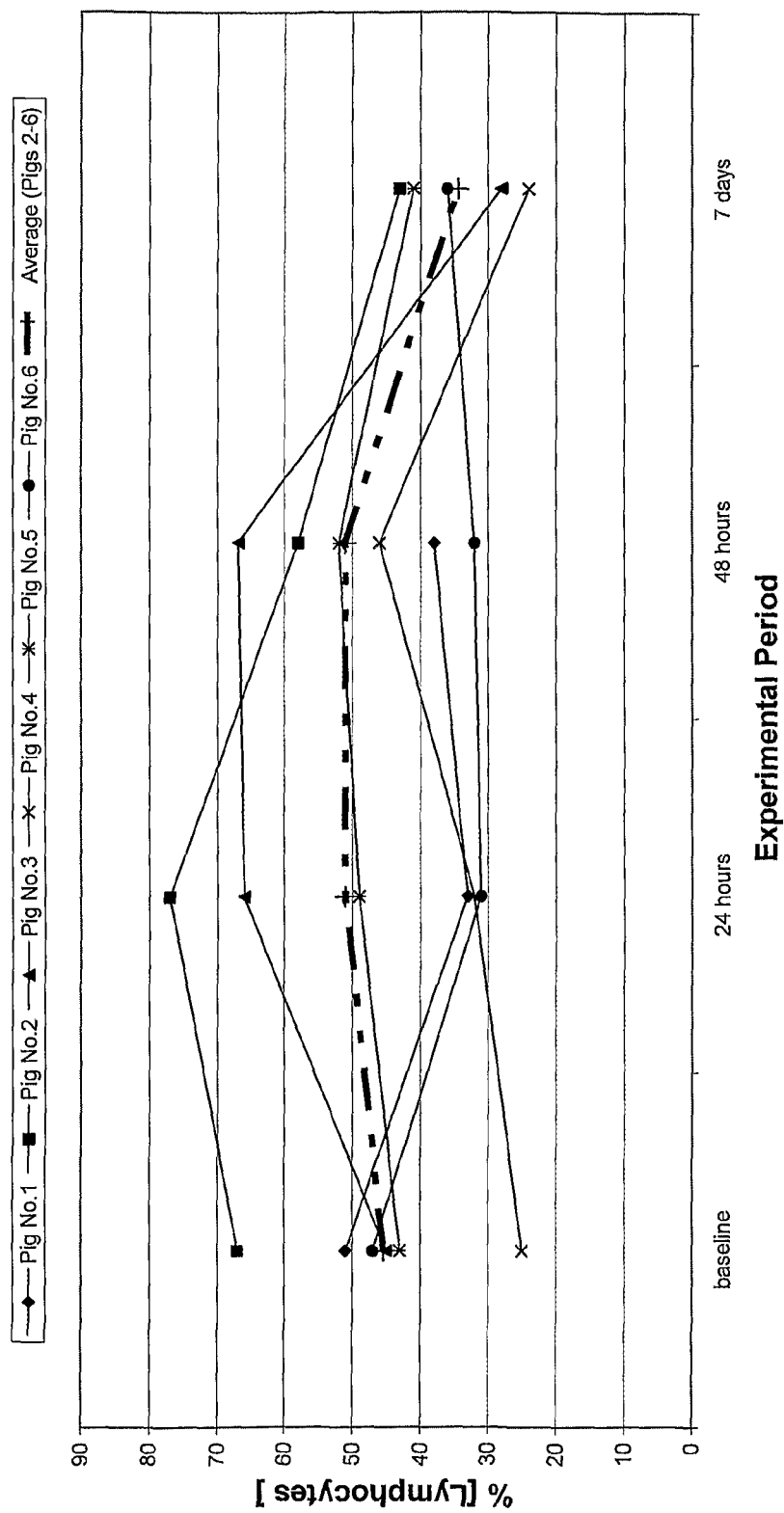

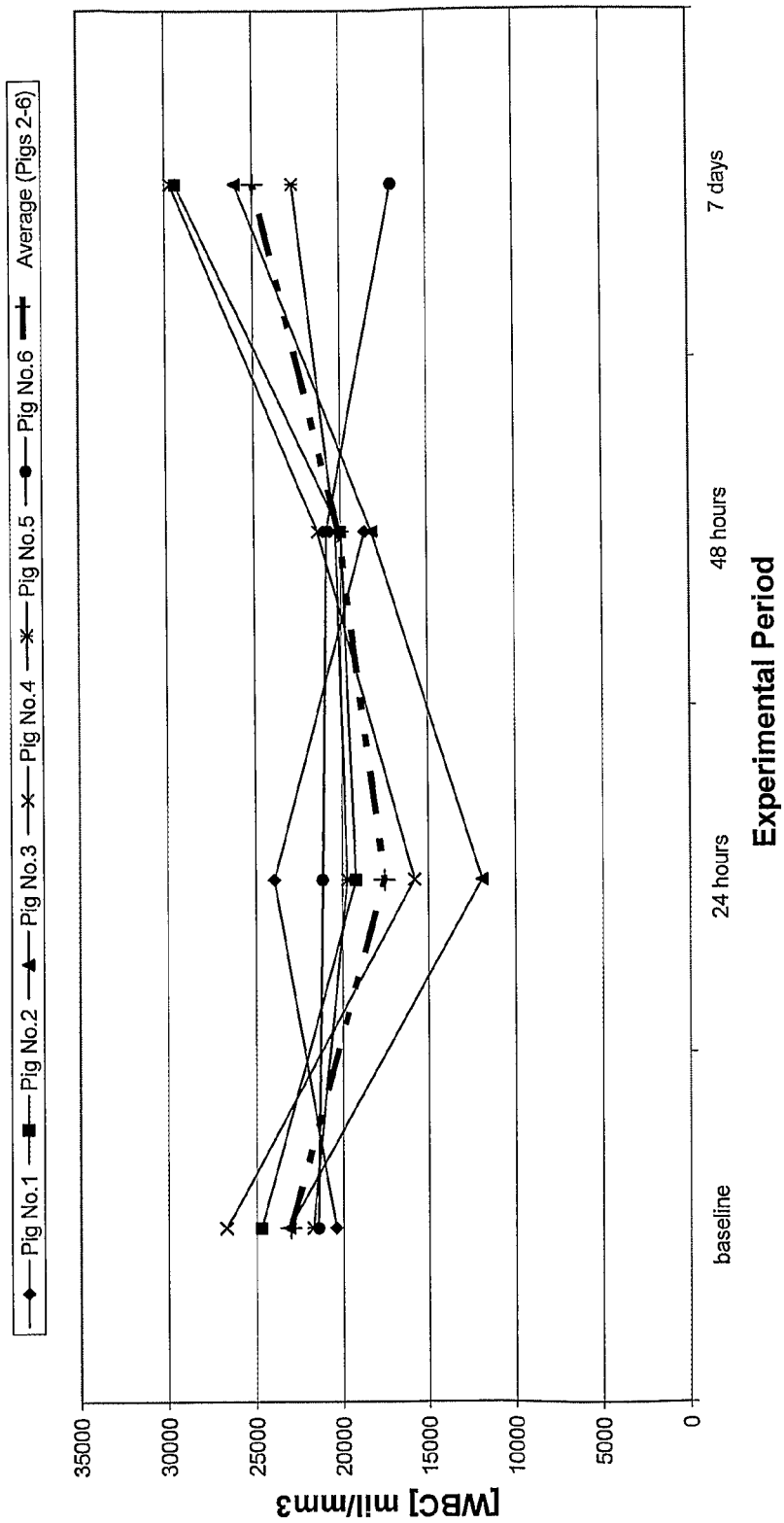
Fig. 8E Analysis of WBC Count
[Range value: 2 - 40 x $10^6$/mm$^3$]

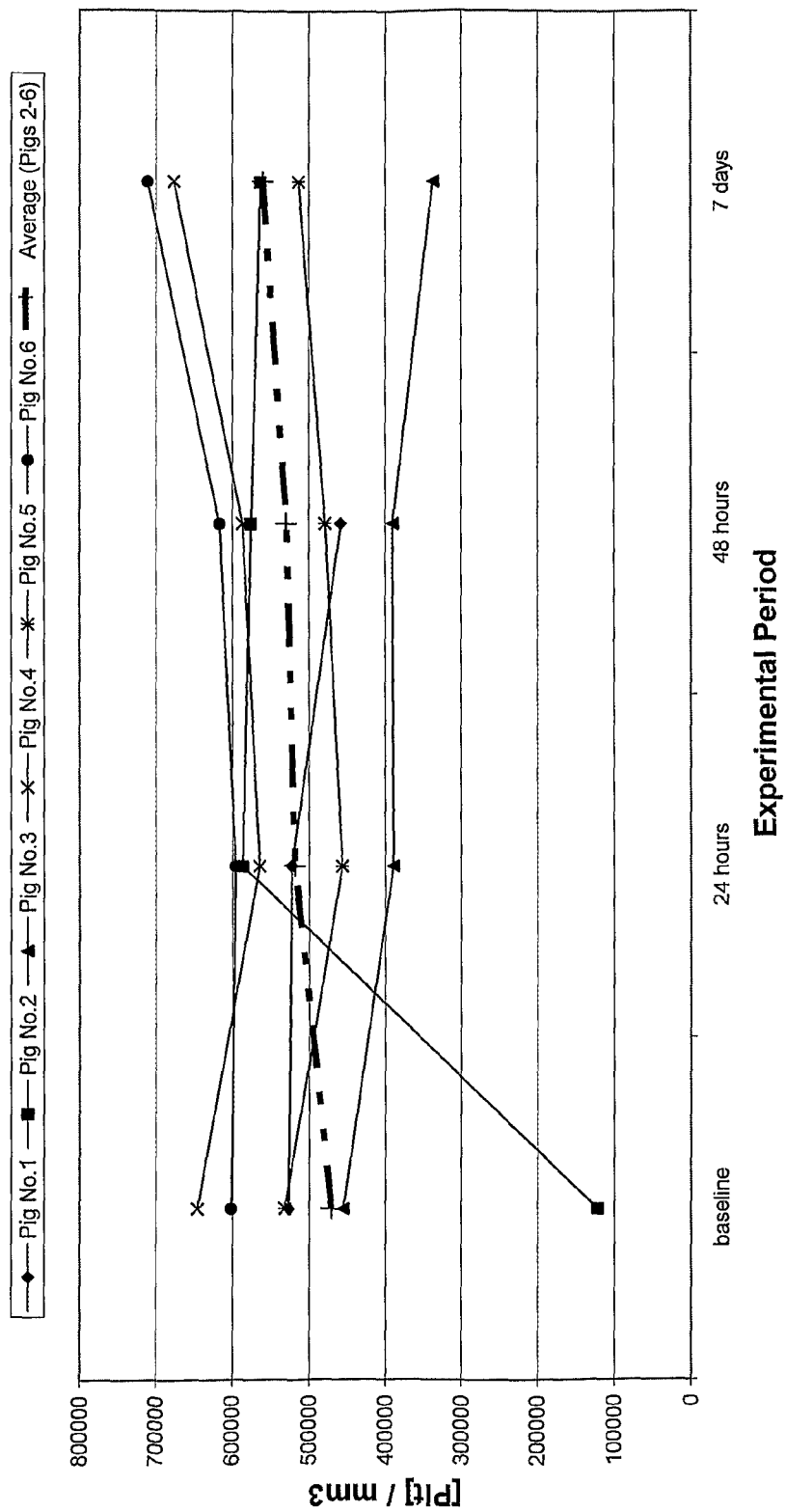
Fig. 9A  Analysis of Platelet Count
[Range value: 120,000 - 720,000/mm3]

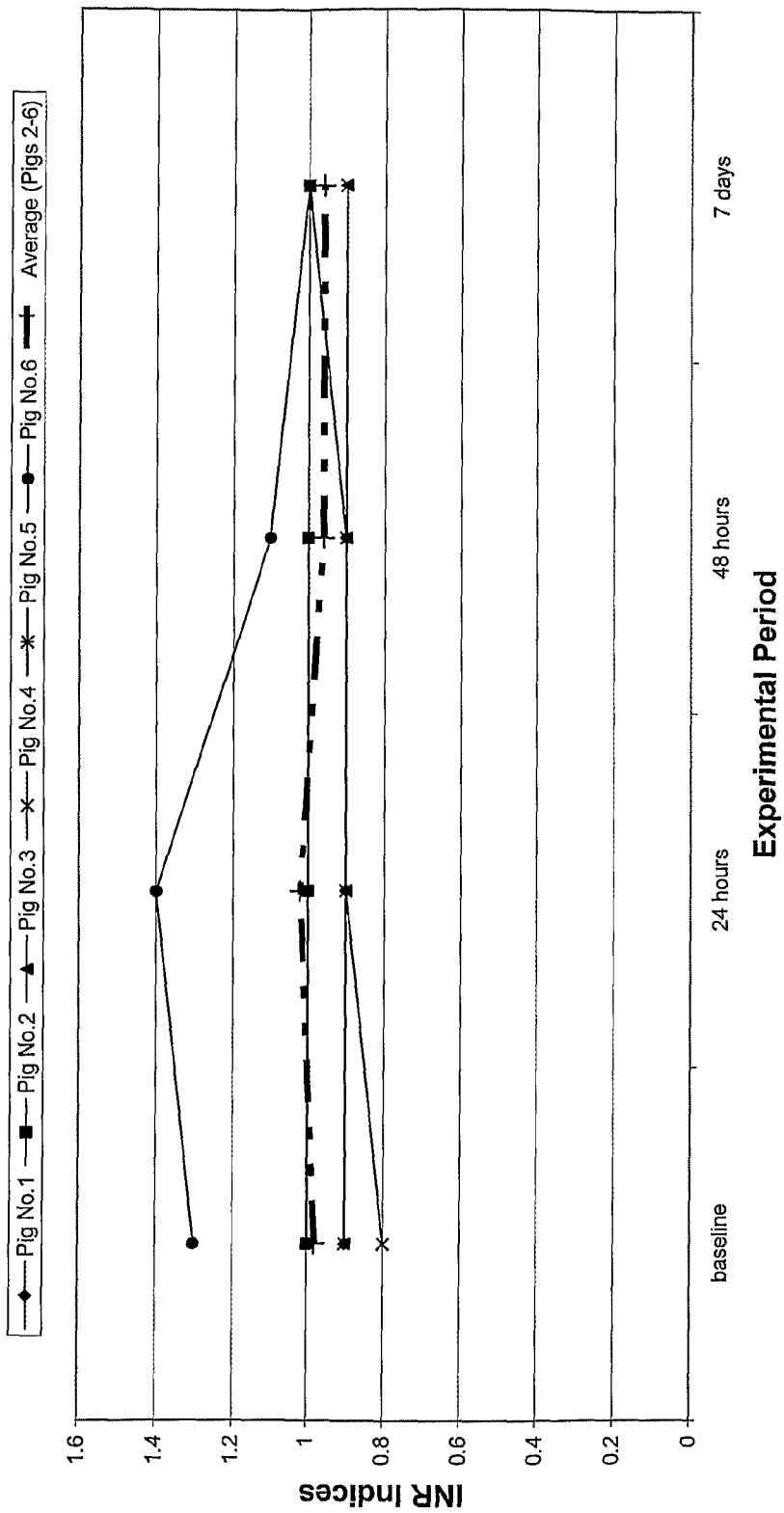

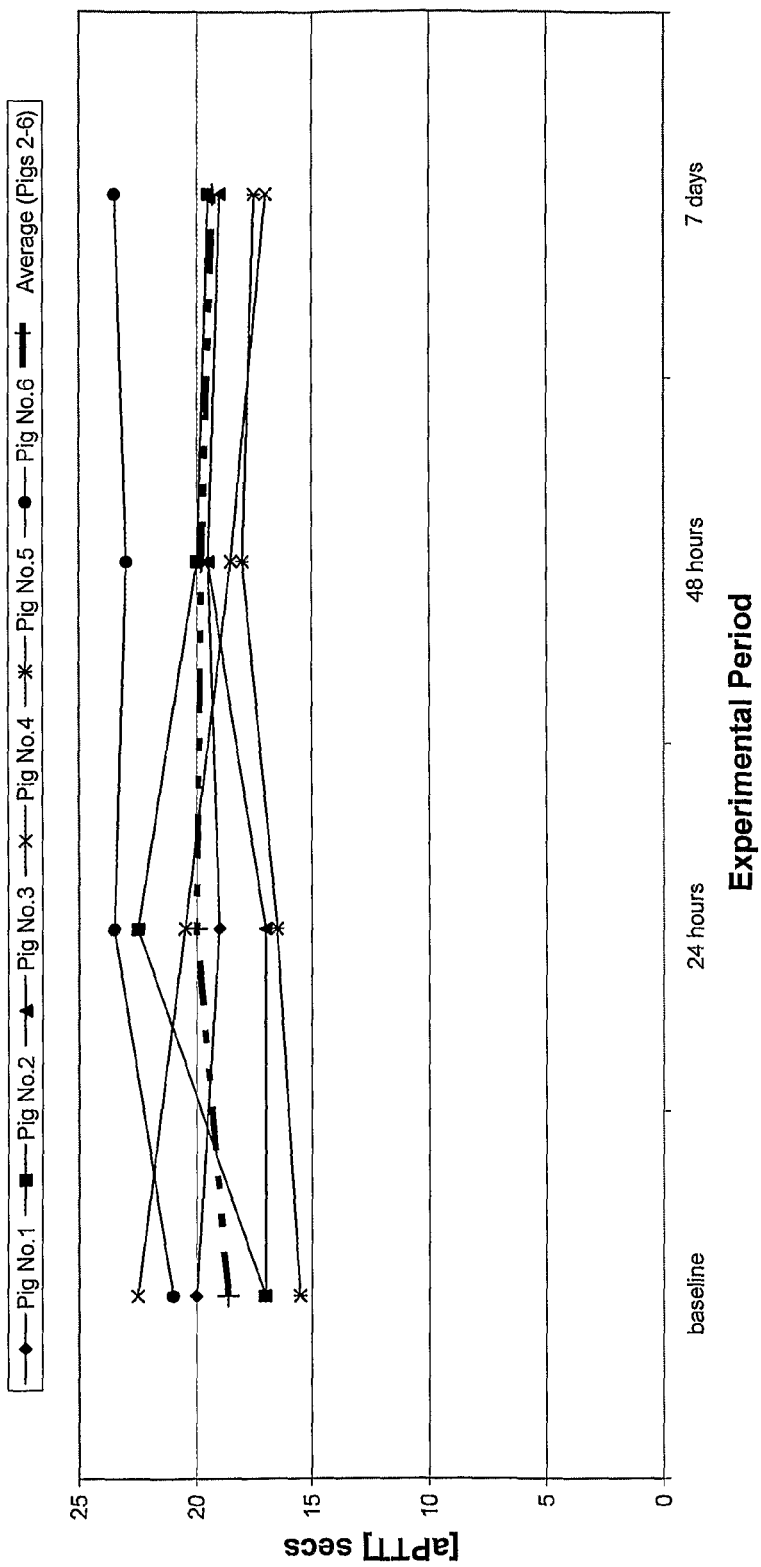

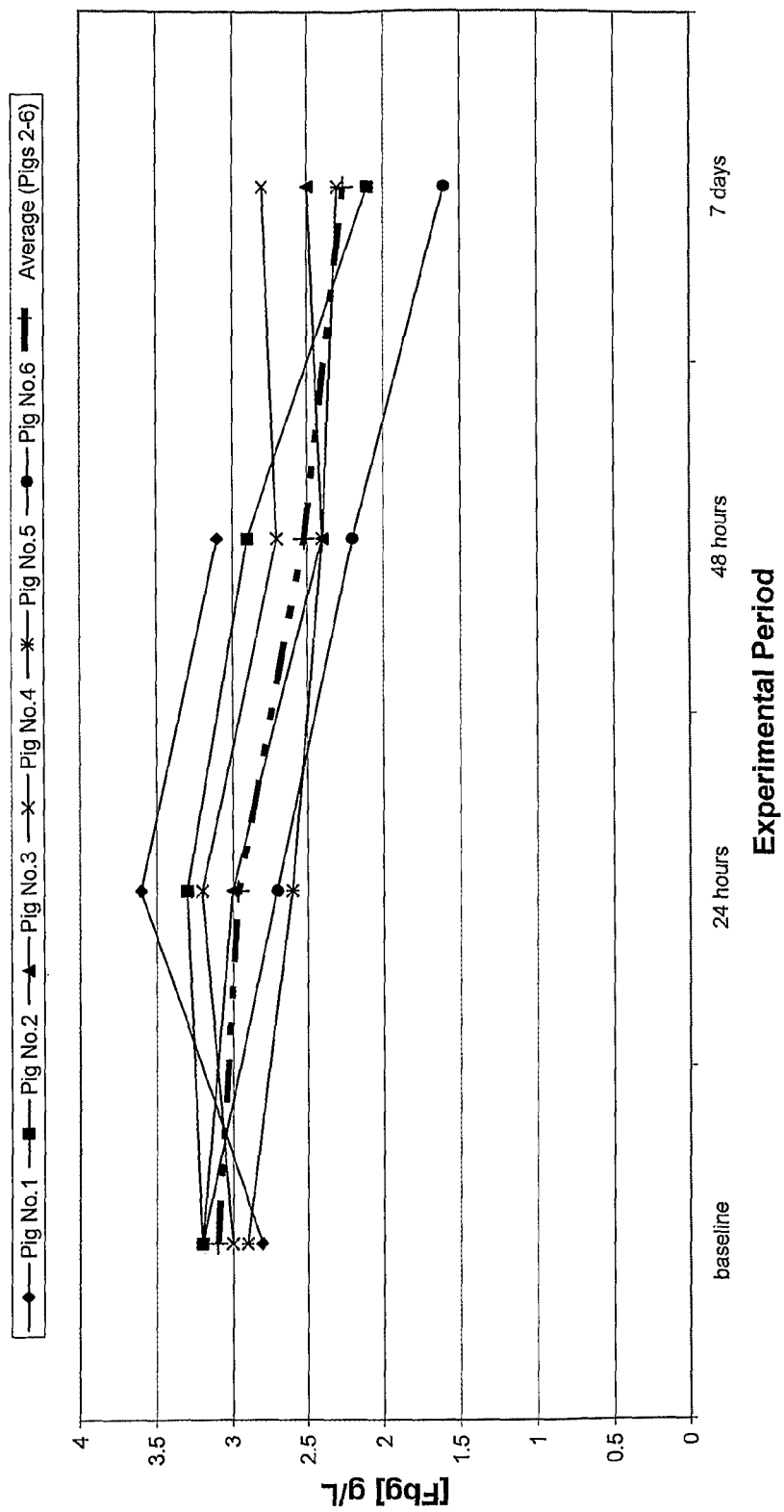

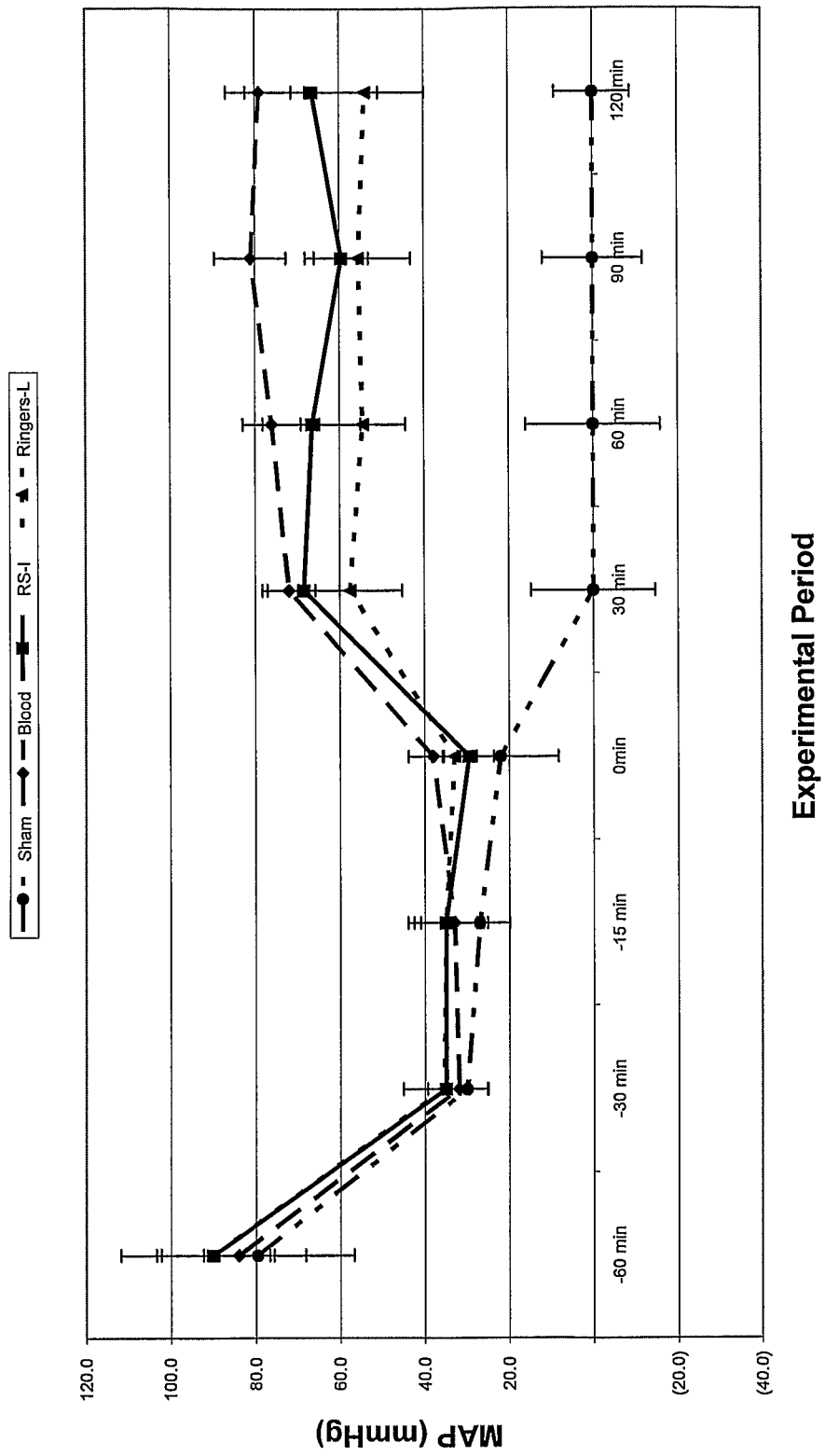
Fig. 11 Mean Arterial Pressure (MAP) during Experimental Period

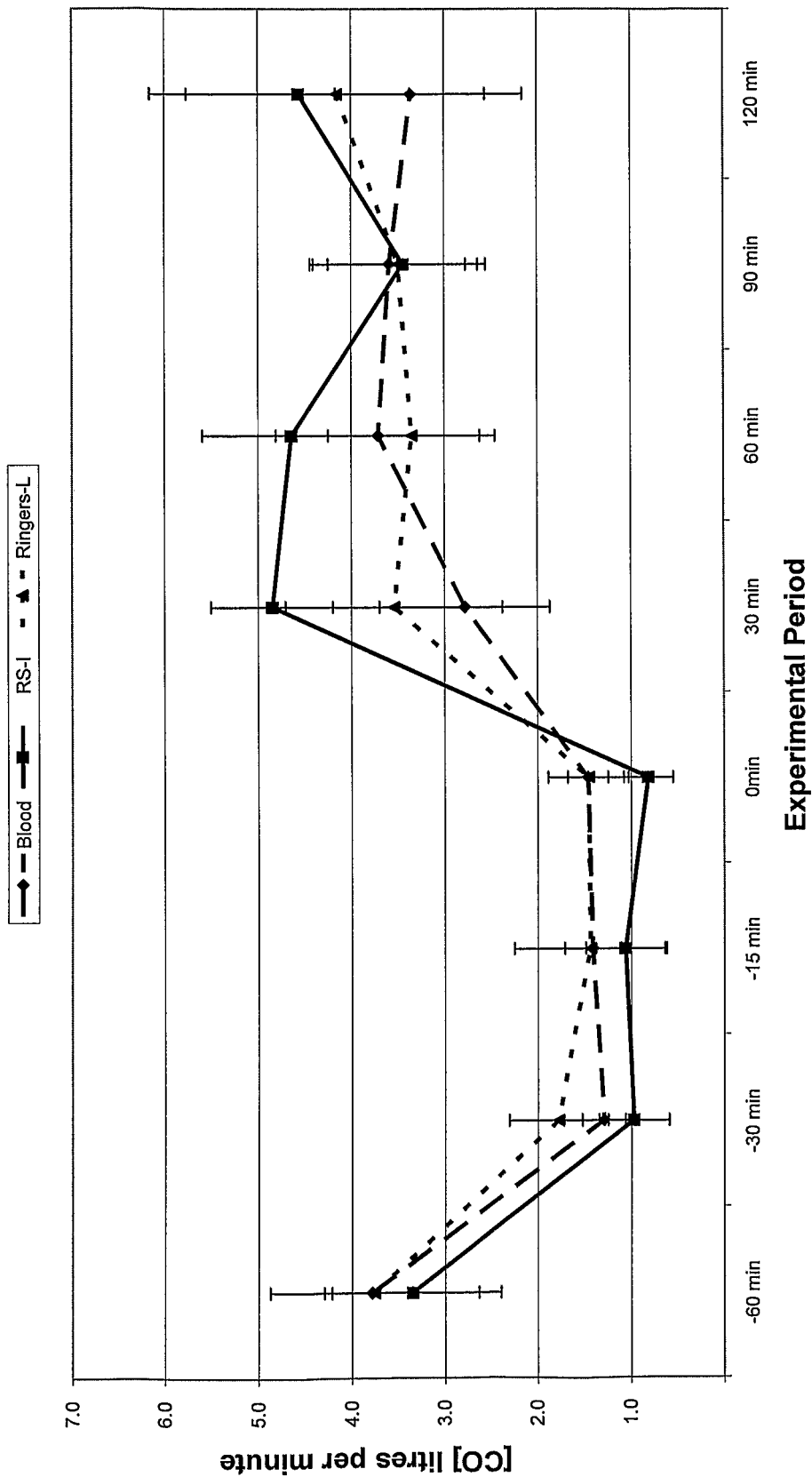

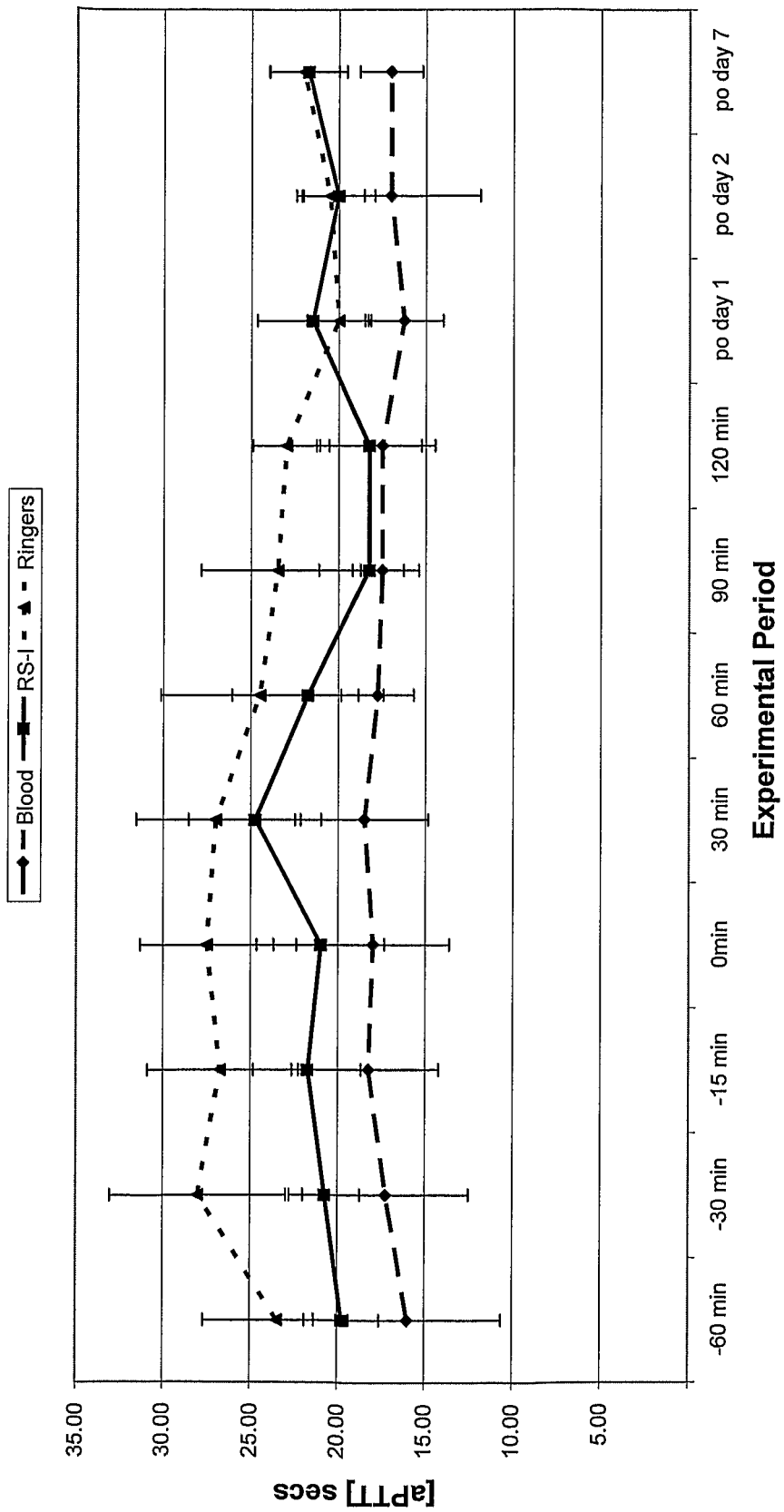

BODY FLUID EXPANDERS COMPRISING N-SUBSTITUTED AMINOSULFONIC ACID BUFFERS

FIELD OF THE INVENTION

The invention relates generally to body fluid expanders. In particular, the invention relates to physiological liquid media for use in expanding, maintaining or replacing blood or extravascular body fluid volume. It is envisaged that the invention will find use in various medical applications, including in intravenous and extravascular (e.g. peritoneal) infusion procedures.

BACKGROUND ART

Loss of blood volume, also known as hypovolemia, can result, for example, from a number of causes including physical injury, surgery, internal haemorrhaging or burns. Hypovolemia can also be induced by the intake of drugs such as diuretics and vasodilators.

A significant loss of blood volume resulting from hypovolemia can be fatal unless treated rapidly. Such blood loss leads to a drop in blood pressure and a reduction in the necessary supply of blood (and with it oxygen) to essential organs and tissues. Consequently hypovolemia can result in ischemia, multiple organ failure, kidney damage, brain damage, and ultimately death.

Hypovolemia is treated by perfusing the subject with crystalloid or colloidal fluids as a substitute for blood lost following hemorrhagic incidents. These fluid substitutes act to expand blood volume, bring about rehydration and normalise blood pressure.

Examples of currently known blood substitutes or blood volume expanders include lactated Ringer's solution, Hartmann's solution, HES (hydroxylethyl starch) and isotonic saline (sodium chloride) (Chiara et al.; Crit Care Med. 2003; 31(7):1915-22; Rhee et al.; J. Trauma. 1998; 44(2): 313-319; Jernigan et al.; Am Surg. 2004; 70(12):1094-8; Via et al.; J. Trauma. 2001; 50:1076-82).

Despite their ability to restore blood volume, the current blood volume expanders are ineffective at preventing a severe and often fatal condition known as reperfusion injury. This phenomenon is observed in subjects who have suffered from severe hypovolemia and manifests itself in the form of damage to essential organs (such as lungs, kidneys, liver, etc). The deleterious effects of reperfusion injury are usually observed between 1 to 3 days following perfusion with blood volume expanders.

SUMMARY OF THE INVENTION

We have identified a need to develop further solutions which are capable of compensating for the loss of blood and the loss of interstitial and extracellular fluid resulting from hypovolemia and severe burns. There is also a need to develop treatments which are effective at preventing or lowering the incidence of reperfusion injury in hypovolemic subjects.

In addition to the above, there is also a need to maintain a sufficient volume of extravascular, interstitial fluid. This fluid, which bathes and surrounds cells, is essential to maintaining the homeostasis of tissues and organs, and functions, inter alia, as a means of delivering materials to cells, removing metabolic waste, and facilitating effective intercellular communication.

The present invention also addresses the significant and important problem of replacement fluid treatments resulting in oedematous conditions within body organs, thereby simply augmenting the incidences of reperfusion injury. The invention is concerned to provide a physiological balanced fluid that complies with the composition of the interstitial fluid in all aspects, but most importantly in terms of tonicity and osmolality, and would facilitate a more natural dynamic fluid exchange between the extravascular space and interstitial phase in conjunction with the lymphatic system, thereby preventing the occurrence of oedema in surrounding tissues.

In one aspect, the invention provides a non-inorganic-phosphate-buffered body fluid expander solution, that is to say a buffered body fluid expander solution in which the buffer is a physiologically acceptable buffer that is not an inorganic phosphate buffer, comprising calcium ions and magnesium ions at a concentration ratio of 5:1 to 1:1.

In another aspect, the invention provides a body fluid expander solution, comprising a non-phosphate buffer which is selected from the group consisting of physiologically acceptable N-substituted aminosulfonic acid buffers, especially those having a $pK_a$ value in aqueous solution of from 7.1 to 7.5 at 20° C., and most preferably from the group consisting of N-tris(hydroxymethyl) methyl-2-aminoethanesulfonic acid (TES), 3-(N-morpholino) propanesulfonic acid (MOPS), N,N-bis(2-hydroxyethyl)-2-aminoethanesulfonic acid (BES) and combinations thereof.

In yet another aspect, the invention provides a body fluid expander solution, comprising calcium ions and magnesium ions at a concentration ratio of 5:1 to 1:1, and further comprising a non-phosphate buffer which is selected from the group consisting of physiologically acceptable N-substituted aminosulfonic acid buffers, especially those having a $pK_a$ value in aqueous solution of from 7.1 to 7.5 at 20° C., and most preferably from the group consisting of TES, MOPS, BES and combinations thereof.

In one embodiment, the non-phosphate buffer is present at a concentration of from 1 to 12 mmoles/L, preferably about 5 mmoles/L The body fluid expander solutions of the invention preferably comprise calcium ions and magnesium ions at a concentration ratio of from 4:1 to 2:1, more preferably about 3:1.

Preferably, the body fluid expander solutions of the invention comprise from 0.1 to 2.5 mmoles/L calcium ions and/or from 0.4 to 25 mmoles/L magnesium ions. The higher concentrations of magnesium ions, towards 25 mmoles/L, are useful for modifications of the solution for cardioplegic purposes, but for regular use as a body fluid expander solution the concentrations noted below are recommended.

In one embodiment, the body fluid expander solutions comprise calcium ions at a concentration of from 1.0 to 2.5 mmoles/L, preferably from 1.1 to 1.4 mmoles/L, more preferably from 1.2 to 1.3 mmoles/L, even more preferably about 1.25 mmoles/L.

The body fluid expander solutions of the invention preferably comprise magnesium ions at a concentration of from 0.2 to 0.6 mmoles/L, more preferably from 0.3 to 0.5 mmoles/L, even more preferably about 0.45 mmoles/L magnesium ions.

In one embodiment, calcium and magnesium ions are present at a concentration of about 1.25 mmoles/L and about 0.45 mmoles/L respectively.

In one embodiment, the body fluid expander solutions of the invention are blood substitutes for expanding and/or replacing blood volume. In yet a further embodiment, the body fluid expanders are extravascular fluid substitutes, e.g., interstitial fluid substitutes.

In addition to the above, the invention also encompasses concentrated forms of the solutions defined herein. For example, 1 to 50×, preferably 5 to 20× concentrates are encompassed. In order to produce a solution of 1×, that is to say working strength, concentration, 5×, 10×, 20× and 50× concentrates require, respectively, 4, 9, 19 and 49 volumes of water to be added to one volume of concentrate, plus the equivalent of 2.1 g of sodium hydrogen carbonate per litre of the diluted 1× solution.

In another aspect, the invention provides solutions as defined herein for use as medicaments and blood volume expanders.

In a further aspect, the invention provides solutions as defined herein for use in treating hypovolemia and/or burns, and for use in preventing and/or ameliorating reperfusion injury.

In yet a further aspect, the invention provides solutions as defined herein for use in: (a) fluid replacement therapy, (b) perfusing a body cavity (e.g. the abdominal or thoracic cavity) of a subject undergoing a surgical procedure, and/or (c) intravascular or extravascular delivery of therapeutic, test and/or synergistic agents to a subject.

The invention also encompasses the use of a solution as defined herein for the manufacture of medicaments and blood volume expanders, e.g. for treating hypovolemia or for treating the loss of extracellular and interstitial fluid in subjects suffering with burns.

The invention also provides the use of a solution as defined herein for the manufacture of a medicament for (a) treating the loss of interstitial fluid in a subject suffering with burns, (b) treating respiratory and/or metabolic acidosis in a subject, (c) perfusion of the abdominal cavity during peritoneal dialysis of a subject with acute renal failure or an acute toxicity condition, or (c) preventing and/or ameliorating reperfusion injury.

In yet a further aspect, the invention encompasses uses of solutions of the invention for delivering a therapeutic, test and/or synergistic agent to a subject, for example a biological agent, such as at least one stem cell, peptide or genomic derived protein.

In preferred embodiments, the delivery is effected by administration via an intravascular, intraperitoneal, intradermal, oral, intramuscular or topical route. Optionally, the delivery is effected by administration to the lymphatic system of a subject.

In yet a further aspect, the invention encompasses methods of treating hypovolemia and/or burns, and methods of preventing and/or ameliorating reperfusion injury, these methods comprising administering to a subject in need thereof an effective amount of a solution as defined herein.

In preferred embodiments the hypovolemia results from dehydration and/or burns and/or bleeding. In another embodiment, the hypovolemia is drug induced.

In a further aspect, the invention provides a method of maintaining physiological homeostasis of a tissue and/or organ in situ during a surgical procedure carried out on a subject, the method comprising perfusing said tissue and/or organ with a solution as defined herein.

In one embodiment of the above method, the solution is maintained at a temperature of between 4 and 20° C. such that said tissue and/or organ, when perfused with said solution, is maintained in a state of hypothermia.

In yet a further embodiment of the above method, the surgical procedure is carried out to retrieve said tissue and/or organ from a donor subject, for subsequent transplantation to a recipient subject.

In yet another aspect, the invention encompasses methods for delivering a therapeutic, test and/or synergistic agent to a subject using the solutions of the invention. In a preferred embodiment, the agent is a biological agent, such as at least one stem cell, peptide or genomic derived protein.

In preferred embodiments, the delivery is effected by administration via an intravascular, intraperitoneal, intradermal, oral, intramuscular or topical route. Optionally, the delivery is effected by administration to the lymphatic system of a subject.

In another aspect, the invention provides the use of a solution as defined herein for (a) dialysis of the peritoneal cavity in a subject suffering from acute renal failure or an acute toxicity condition; and/or (b) irrigation of abdominal and/or thoracic organs in a subject undergoing a surgical procedure.

In yet another aspect, the invention encompasses a substantially inorganic-phosphate-free buffered solution for use as a medicament, especially one that is also substantially free of at least one of citrate and lactate buffer

BRIEF DESCRIPTION OF SEVERAL VIEWS OF THE DRAWINGS

FIG. 1 Assessment of the survival of rats over time as a function of the resuscitation solution used. Rats were subjected to serial withdrawals of blood. The rats were separated into three experimental treatment groupings as follows: (1) replacement of blood with physiological saline; (2) replacement of blood with a preferred solution in accordance with the invention, referred to herein as RS-I solution or RS-I; and (3) no replacement of blood losses. Survival of rats in each of the various groupings was monitored and the data set out in FIG. 1.

FIG. 2 Comparison of the total volume of blood withdrawn for each of the study arms defined with reference to FIG. 1 above. Blood was withdrawn from rats as described in the Example 4 below.

FIG. 3 Assessment of the respiratory rates of rats over time in the various study arms defined with reference to FIG. 1.

FIGS. 4A, 4B, 4C, 4D, 4E and 4F: Assessment of pig blood profiles over various time periods of perfusion with RS-I. Pigs were infused with 1.0 L of RS-I solution every day for three days and blood samples were taken at various time points. Blood samples were tested, inter alia, for complete blood counts, serum chemistry determination, electrolytes, glucose, lactate, osmolality, serum enzymes (serum glutamic oxaloacetic transaminase/aspartate aminotransferase [SGOT/AST], serum glutamic pyruvic transaminase/alanine aminotransferase [SGPT/ALT], creatine kinase [CK] and lactate dehydrogenase [LDH]), coagulation factors and fibrinogen levels. Also, blood was measured for inter leukin-6 (IL-6) and tumor necrosis factor-alpha (TNF-α).

FIG. 4G Summary Data Table re Blood Data Analysis in a Normovolemic Pig model

FIGS. 5A, 5B, 5C, 5D, 5E, 5F and 5G: Analysis of Serum Electrolyte Levels in a Normovolemic Pig model FIGS. 6A, 6B, 6C and 6D: Analysis of Serum Metabolites Levels in a Normovolemic Pig model FIGS. 7A, 7B, 7C and 7D: Analysis of Serum Enzyme Levels in the a Normovolemic Pig model FIGS. 8A, 8B, 8C, 8D and 8E: Analysis of Blood Cell Profiles in a Normovolemic Pig model FIGS. 9A, 9B, 9C and 9D: Analysis of Blood Clotting Parameters in a Normovolemic Pig model FIG. 10 Comparison of the ADP:ATP (adenosine diphosphate:adenosine triphosphate) ratios in cold static ((IS) and warm static (WS) group pig kidneys before and after 6 hours of normothermic perfusion.

FIG. 11 Change in the mean Arterial Pressure following resuscitation in Autologous Blood, RS-I fluid and Lactated Ringer's saline FIG. 12 Activated Prothromboplastin Time (aPTT) following resuscitation in Autologous Blood, RS-I fluid and Lactated Ringer's saline FIG. 13 Activated Partial Thromboplastin Time (aPTT) during Experimental Period

DETAILED DESCRIPTION OF INVENTION

Figure 10:
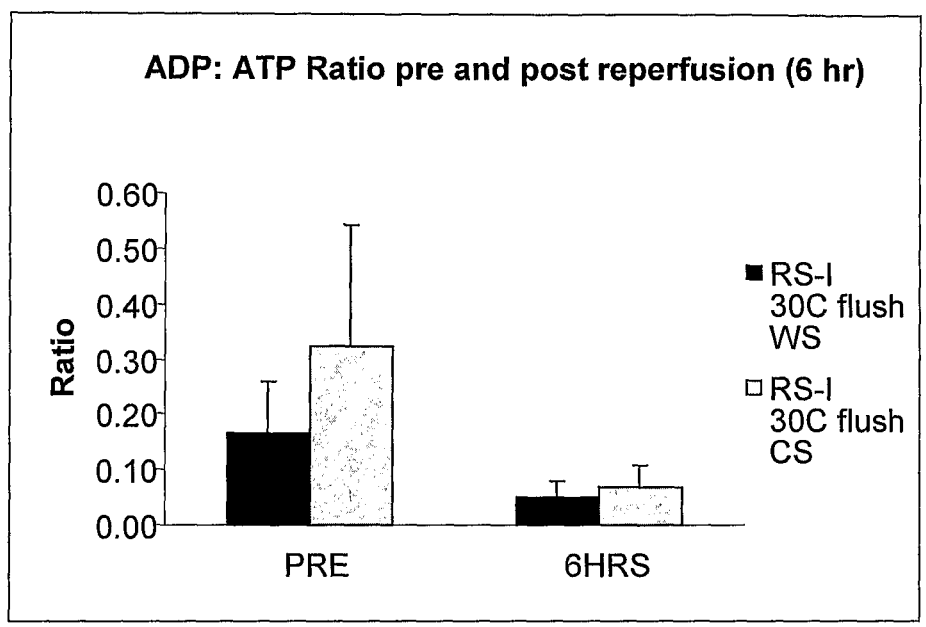

The terms "body fluid expander" or "body fluid expander solution" or "body fluid substitute" as used herein mean a physiological liquid solution which is intended for use in replacing or expanding body fluid, and/or maintaining a sufficient volume of body fluid. The body fluids for which the solutions of the invention are intended to expand, replace or maintain include intravascular fluids (e.g. blood components such as plasma), or alternatively, extravascular fluids (e.g. interstitial fluid).

The terms "body fluid expander" and "body fluid expander solutions" also encompass physiological liquid media which are intended for use as a vehicle for the delivery of therapeutic, test and/or synergistic agents into the body of a subject in need of said agents, or in circumstances where the agents are to be tested, for example on non-human subjects.

The term "subject" or "subjects" encompasses, where appropriate, human subjects and non-human animal subjects, for example mammalian subjects such as rodents, pigs, monkeys, dogs and the like as appropriate in experimental research and cattle, horses and the like as occurs in veterinary practice.

Terms such as "non-phosphate buffer" and "substantially phosphate free" are intended to encompass fluid embodiments which substantially lack inorganic phosphate ions.

The terms "blood volume expander" or "blood volume expander solution" or "blood substitute" as used herein mean a physiological liquid solution which is intended for use in replacing, expanding or maintaining blood volume. These solutions therefore find use in substituting for a loss of blood volume resulting from hypovolemia.

The term "hypovolemia" as used herein means a state of decreased blood volume, or more specifically, a state of decreased blood plasma volume. Common causes of hypovolemia include dehydration, burns, bleeding (e.g. haemorrhaging) or the intake of certain drugs such as diuretics and vasodilators.

The term "reperfusion injury" as used herein means the injury caused to essential organs of the body following hypovolemia and subsequent perfusion with conventional blood volume expanders.

The present invention emerges from a realisation of the inventor that conventional blood volume expanders are detrimental to the maintenance of cell, tissue and organ survival and viability, and can hence contribute to the development of reperfusion injury.

In part, the present invention stems from an appreciation that the composition of blood volume expanders (and physiological media in general) should be based on a specific knowledge of the activity coefficients of ionic species within the interstitial gel phase surrounding each cell. These activity coefficients have been calculated and the solutions of the present invention have been designed in accordance with these calculations.

The solutions of the invention make use of non-phosphate buffers, based on the realization that excess phosphate ions can be deleterious to the viability and functional integrity of perfused cells, tissues and organs. Phosphate ions inhibit glycolysis, oxidative phosphorylation (Berman & Sanders; Circul. Res., 1955; 3, 559-563), creatine kinase activity (Hall & DeLuca; Adv. Exp. Med. Biol. 1986; 194, 71-82) and the enzymes involved in oxygen free radical scavenging (De Frietas & Valentine; Biochemistry 1984; 23:2079). These enzymes are important in inducing apoptotic changes at the cellular level, ultimately leading to the necrosis (i.e. death) of damaged or abnormal cells, tissues and organ systems.

Essentially, the use of non-phosphate buffered solutions avoids the inefficiency of conventional phosphate buffered solutions in terms of instability above pH 7.2. In particular, inorganic phosphate ions in conventional solutions are, over time, precipitated in the form of insoluble calcium phosphate (Pedersen, Md. Thesis, University of Arhus, Denmark. Publ. S A Moller Christensen A/S. 1973; 41-51). This problem is accentuated by variations in the temperature range at which the solutions are used and therefore such conventional buffered solutions are of limited clinical utility. Furthermore, a number of other non-phosphate buffer agents, e.g., citrates, certain amino acid combinations, and lactated solutions, are distinct from the natural or physiological pH buffer agents operating in mammalian species and have been found to be ineffective in preserving organ function under ex vivo (see, EXAMPLE 6) and in vivo (see, EXAMPLE 8) normothermic conditions. In contrast, the solution of the invention, when in use as a body fluid expander, has enhanced performance because it is capable of utilising the natural buffer system found in all mammals, namely, a $pCO_2$/hydrogen carbonate system.

Described herein are body fluid expander solutions which, by virtue of their composition, are able to compensate either for loss of blood in hypovolemic subjects, or loss of interstitial and extracellular fluid associated with severe burns. The body fluid expander solutions of the invention provide physiological liquid media which mimic the ionic, substrate and biophysical environment of interstitial fluid (see, for example, Table II below). As such, it is envisaged that these solutions will find use as universal perfusion and preservation media. The concentrations of ion species acknowledge the activity coefficients of each ionic species within the interstitial gel phase around mammalian cells. This is in contrast to many conventional media which base their concentrations on total serum concentrations.

In U.S. Pat. No. 6,946,241 (which is incorporated herein by reference), the present inventor describes non-phosphate buffered liquid cell culture media. It has now been appreciated that effective blood volume expander solutions and body fluid expander solutions in general can be based on the composition of these media. It is envisaged that the solutions of the present invention will not only compensate for the loss of blood associated with hypovolemia but will also reduce or prevent the onset of reperfusion injury. It is also envisaged that the solutions defined herein will have application in the in situ maintenance of organs and tissues, which become exposed during various surgical procedures.

The body fluid expander solutions of the present invention are preferably free of serum and/or serum components. The solutions are hence free of animal derived serum proteins and other contaminants, such that there are no undefined, extraneous serum proteins present. The absence of serum has the advantage that the solutions are "chemically" better defined than conventional serum based solutions. Furthermore, the absence of serum and serum derived components avoids concerns over the possible transmission of infectious diseases (e.g. Human immunodeficiency virus (HIV) and Creutzfeldt-Jakob disease (CJD) associated with the use of this material in vivo.

For the reasons given above, the body fluid expander solutions of the present invention (and particularly those solutions intended for human use) are also preferably free of foreign or animal derived antigens, pyrogens, proteins and the like. However, in certain situations, e.g. dialysis, susceptible patients may require the presence of specific peptide or protein derived components as a compensatory measure for the reported loss of proteins during renal or peritoneal dialysis. The solutions of the invention may provide effective vehicles for use in delivering such components to patients.

A major discovery that has evolved during work with solutions similar to the solutions of the present invention in isolated tissue and organ perfusion experiments is that they can utilise the natural pH buffering mechanisms observed in all mammalian species, namely, auto-regulation of the partial pressure of carbon dioxide [$pCO_2$] and concentration of the bicarbonate ion [$HCO_3^-$] in blood even in the absence of red blood cells. The interrelated dissociation constant [$pK_a$] afforded by the imidazole/histidine moieties of hemoglobin appears to be simulated by suitable buffers used in this invention, most preferably BES buffer which, because of its useful $pK_a$ (7.15) and $-\Delta pK/°$ C. (0.016) at 20° C., automatically maintains the pH of RS-I solution between 7.18-7.45 over a temperature range of 10-37° C. and therefore becomes particularly suitable as a buffer agent in the solution of the invention for use with mammalian species under both hypothermic and normothermic physiological conditions.

As previously stated, the body fluid expanders of the present invention adopt and take advantage of a natural physiological buffering system. Preferably this buffering system takes the form of $NaHCO_3/pCO_2$ (sodium hydrogen carbonate/dissolved $CO_2$) in combination with the zwitterionic Good's buffer, BES (N, N-bis[2-Hydroxyethyl]-2-amino-ethanesulphonic acid (Good et al.; Biochemistry 1966; 5:467-477), incorporated herein by reference), which acts by virtue of its ideal $pK_a$ over a temperature range of 10 to 37° C., to provide a stable pH, an essential requisite for cellular preservation. BES has been shown to be non-toxic to cultured mammalian cells in long term studies and exhibits negligible binding of calcium or magnesium ions, so removing the potential hazard of precipitation of divalent ions which occurs when using conventional hydrogen carbonate/phosphate or double phosphate buffer solutions. Indeed, 10× concentrates of solutions according to the invention have been experimentally shown to have a shelf life (stored at 3 to 8° C.) in excess of 14 months. As alternatives to the use of BES, it is also possible to use morpholinopropane sulphonic acid (MOPS) or N-tris-(hydroxymethyl) methyl-2-amino ethane-sulphonic acid (TES). Furthermore, a combination one or more of TES, BES and MOPS could be used.

Other physiologically acceptable N-substituted aminosulfonic acid buffers may be chosen according to specific requirements, and the following Table lists potential candidates and their $pK_a$ values in aqueous solution at 20° C.

| N-substituted Aminosulfonic Acid Buffer Agents | $pK_a$ @ 20° C. | $-\Delta pK_a/°$ C. |
|---|---|---|
| MES: 2-(N-morpholino) ethanesulfonic acid | 6.15 | 0.011 |
| ADA: N-(2-acetamido) iminodiacetic acid | 6.62 | 0.011 |
| ACES: N-2-(acetamido)-2-aminoethanesulfonic acid | 6.88 | 0.02 |
| BICINE: N,N-bis (2-hydroxyethyl) glycine | 8.35 | 0.018 |
| BES: N,N-bis (2-hydroxyethyl)-2-aminoethanesulfonic acid | 7.15 | 0.016 |
| HEPES: N-(2-hydroxyethyl) piperazine-N'-(2-ethanesulfonic acid) | 7.55 | 0.014 |
| MOPS: 3-(N-morpholino) propanesulfonic acid | 7.20 | 0.011 |
| PIPES: piperazine-N,N'-bis(2-ethanesulfonic acid) | 6.80 | 0.009 |
| TES: N-tris(hydroxymethyl) methyl-2-aminoethanesulfonic acid | 7.50 | 0.020 |
| TRIS: tris(hydroxymethyl) aminomethane | 8.3 | 0.031 |
| TRICINE: N-tris(hydroxymethyl) methylglycine | 8.15 | 0.021 |

Optionally, the non-phosphate buffer (preferably TES, MOPS or BES, or combinations thereof) is present at a concentration of from 1 to 12 mmoles/L, preferably from 3 to 7 mmoles/L, more preferably from 4 to 6 mmoles/L, even more preferably about 5 mmoles/L. Optionally, hydrogen carbonate ions are present at a concentration of from 21 to 35 mmoles/L, preferably from 23 to 26 mmoles/L, more preferably about 25 mmoles/L.

In preferred embodiments of the invention, the non-phosphate buffer systems used allow, because of their unique $pK_a$ range, the ability to automatically adjust the pH of the solutions of the invention from 7.05 to 7.5 over a temperature range of from 4° C. to 38° C. This feature of the invention, unlike that found with conventional buffering systems, does not require any further intervention in adjusting the pH to give values ranging from 7.13 to 7.5±0.5 over a temperature range of 10 to 38° C. Preferably, the solutions of the invention have a pH of about 7.46 at a temperature of about 37.4° C. It is preferred that the above pH values are maintained in vivo following administration of the solutions to a subject in need thereof.

As discussed herein, the solutions of the invention may be used for both intra- and extravascular infusion procedures. The solutions may also be used to perfuse isolated animal and human organs under normothermic conditions. When the solutions are used to perfuse isolated organs, it is preferable that the solutions are aerated with carbogen gas (95% oxygen/5% carbon dioxide).

The body fluid expander solutions of the present invention may also comprise in any combination, one or more, two or more, three or more, four or more, five or more, six or more, seven or more, eight or more, nine or more, ten or more, eleven or more, twelve or more, thirteen or more, fourteen or more, or all of the following components: from 100 to 150 (preferably about 135) mmoles/L sodium ions, from 2.5 to 6.2 (preferably about 5) mmoles/L potassium ions, from 0.1 to 2.5 (preferably about 1.25) mmoles/L calcium ions, from 0.4 to 25.0 (preferably about 0.45) mmoles/L magnesium ions, from 96 to 126 (preferably about 118) mmoles/L chloride ions, 2 to 11 mmoles/L (preferably about 10) glucose (preferably D-glucose), from 50 to 150 (preferably about 110) μmoles/L glycerol, from 7 to 15 (preferably about 10) μmoles/L choline, from 5 to 400 (preferably about 300) μmoles/L glutamate (preferably L-glutamate), from 5 to 200 (preferably about 20) μmoles/L aspartate (preferably L-aspartate), from 100 to 2000 (preferably about 400) μmoles/L glutamine (preferably L-glutamine), from 15 to 215 (preferably about 60) μmoles/L pyroglutamate, from 20 to 200 (preferably about 100) μmoles/L arginine (preferably L-arginine), from 1 to 120 (preferably about 40) nmoles/L thiamine pyrophosphate (TPP), from 40 to 70 (preferably about 50) μmoles/L D- or DL or L-carnitine (preferably L-carnitine), and from 5 to 200 (preferably about 28) mI.U./L porcine or human insulin (preferably human insulin).

Chloride ions, when present, are preferably provided as sodium, potassium, calcium and magnesium salts. Preferably, when present, choline is provided as a chloride salt.

Solutions encompassed by the present invention comprise a number of substrates which retain metabolic homeostasis of tissues and organs. Glucose and glycerol have been shown to be satisfactory in meeting the energy demands of isolated tissues and organs, even when they are not the preferred substrate for the organ in question (e.g. the heart) by the inclusion of physiological levels of insulin. Apart from their ability to be metabolized, glycerol and glucose also have free radical scavenging and membrane stabilizing properties, which have been shown to be extremely important in maintaining the physiological viability of tissues and organs.

As described above, aspartate and glutamate can also be included in the solutions according to the invention, to enhance oxidative metabolism by replenishing tricarboxylic acid (TCA) cycle intermediates, thereby maintaining high energy phosphate levels even during ischemic insult. Similarly, glutamate is involved in maintaining intracellular oxidation-reduction potentials. It is envisaged that by optimizing the aspartate-malate and glycerol phosphate shuttles, cells will maintain an optimal NAD/NADH (nicotinamide adenine dinucleotide/reduced nicotinamide adenine dinucleotide) balance and thereby sustain adenine nucleotide levels. In addition, glutamate and glutamine can act as intermediary metabolites to form pyroglutamate and thereafter participate in the gamma-glutamyl cycle to synthesise glutathione, a beneficial agent in preventing the generation of toxic oxygen radicals associated with the incidence of reperfusion injury in mammalian tissues and organs during storage of donor organs prior to transplantation and following blood volume replacement therapies.

Thiamine plays an important role in the oxidation of α-keto acids (by the action of thiamine cocarboxylase) and prevents the accumulation of pyruvate and toxic pyruvate aldehyde, thereby minimizing cellular apoptosis and accompanying necrosis of tissues and associated organs.

In the TCA cycle, thiamine pyrophosphate (TPP), which is included in preferred solutions of the invention, is a co-factor in the metabolism of a-ketoglutaric acid to form succinyl-coenzyme A, by oxidative decarboxylation, or to form glutamate, by reductive amination. In essence, TPP is involved in numerous interrelated biochemical pathways, especially those of the Pentose Phosphate and Glycolytic pathways. The thiamine may be employed as thiamine pyrophosphate, thiamine diphosphate or thiamine diamide. Preferably the solutions of the invention comprise thiamine as thiamine pyrophosphate chloride.

Further, the inclusion of thiamine pyrophosphate in the formulation of the solutions of the invention would also appear to be of necessity to peritoneal dialysis patients in order to prevent phosphate ion depletion and calcification as it is readily dialyzable across hemodialysis membranes (MW—175 Dalton) and has been previously administered either intravenously or via the hemodialysis or peritoneal dialysis solution to replenish plasma phosphate and/or pyrophosphate levels.

The vitaminoid carnitine has been reported to have multiple effects in improving cardiac function other than by simply optimizing oxidative metabolism, such as, by promoting the utilization of alternative substrates and may additionally improve coronary blood flow. L-carnitine is preferred to the D- or DL isomers because it causes no inhibition of acetyl co-enzyme A/free fatty acid metabolism. Preferably the vitaminoid component comprises 50 μmoles/L of [−]-β-hydroxy-γ-trimethylamino-butyrate hydrochloride (L-carnitine). In this invention, the preferred inclusion of the L-isomer of carnitine is intended to optimise the transport of long chain fatty acids from the cytosol into the mitochondrial matrix to the site of β-oxidation and thereby to buffer the intramitochondrial acetyl CoA/CoA ratio (where CoA is Coenzyme A) by stimulating the synthesis of acetyl carnitine from carnitine acetyl transferase. This reduction in the ratio of acetyl CoA/CoA will result in an efflux of acetyl carnitine from the mitochondria with an associated stimulation of pyruvate dehydrogenase and reversal of fatty acid inhibition of glucose oxidation. Ultimately the optimization of free fatty acid utilization as an energy source is essential for all types of cells but this must be done with preservation of carbohydrate (glucose) utilization by optimized functioning of the enzymes involved in glycolysis, eg. hexokinase, glucokinase, phosphofructokinase.

As described above, solutions of the invention may also comprise insulin. The use of human recombinant insulin (e.g. expressed in *E. coli* or *S. cerevisiae*) not only precludes the risk of antigenic or viral contamination in recipient cells/tissues/organs, as may be the case with insulin derived from other mammalian or animal sources, but also leads to a better fit being achieved of insulin molecules to human insulin receptor structure, ie. Receptor specificity will be optimized to retain the many associated functions of insulin in cellular processes.

Essentially, the biological effects of insulin do not simply relate to its ability to regulate carbohydrate metabolism and facilitated transport of circulating glucose into cells but also in its ability to bring about (i) the enhancement of intracellular glucokinase activity and amino-acid incorporation into protein, (ii) stimulation of DNA (deoxyribose nucleic acid) translation into proteins, (iii) increased lipid synthesis and (iv) stimulation of sodium, potassium and inorganic phosphate transport across cell membranes.

In preferred embodiments of the invention, normal, human serum levels of insulin have been utilized. In contrast, conventional known perfusate formulations have, when incorporating insulin, made use of unnatural levels of this hormone (e.g. 10 to $50 \times 10^6$ mIU/L; about a million times more concentrated that the insulin found in solutions of the invention). The reason for this relates to the fact that only a small amount of the insulin exists as single molecules in such concentrations. The rest of the insulin exists in the form of large aggregates, which are ineffective at stimulating insulin receptors and are hence biologically inactive. The solutions of the invention achieve normal, human serum levels of insulin by acidifying the insulin during formulation to prevent aggregate formation, so allowing individual active, molecular species of insulin to exist in solution at pH $7.3 \pm 0.2$.

The concentrations of ionic species in solution according to the invention acknowledge the activity coefficients of each ionic species and not simply their total serum concentrations. For example, serum binding of calcium and magnesium ions must be distinguished from the actual free, ionized levels of these ions. Magnesium ions are important in a number of critical cellular reactions and their extracellular presence is reported to stimulate mitochondrial respiratory activity and modulate the effects of rapid calcium influx and potassium efflux. Equally, an adequate concentration of calcium ions is important to maintain the free levels of this ion present in the circulation.

The ionic conductivity of the solutions of the invention is preferably comparable to that of human serum, namely $12.0\pm0.3$ mS cm$^{-1}$ and as such maintains the ionized status of the cell membrane and activities of enzymic moieties.

Thus in accordance with the above, the solutions of the present invention are isosmotic to human serum (ca. 290 mOsmoles/L) and do not appear to necessitate the inclusion of plasma expanders, as demonstrated by the fact that only minor changes (ca. 8%) in hydration occur during long term (ie. 4 to 52 hr) hypothermic perfusion of the isolated rat heart and visceral nerve-muscle preparations. This may be explained by the fact that the cell membrane lies in continuity with a 99% gel interstitial phase so providing natural colloidal buffering to excess Donnan ionic equilibrium exchange across the cell membrane. The majority of the osmotic pressure is provided by sodium ions and their accompanying anions, and only a small component (ca. 0.5%) can be attributed to plasma proteins. The inclusion of serum levels of the metabolite, glycerol, in this solution may also contribute to osmotic buffering at the interstitial fluid interface surrounding each cell, specifically that involving the transcapillary network.

The practicality of including oncotic agents is further compromised by their affinity for calcium and magnesium ions, necessitating prior dialysis in fresh solution so as not to disturb cationic composition. The labile nature of polypeptide expanders also makes them impractical through their predisposition to mechanical denaturation. Unfortunately, while these colloidal expanders are essentially non-toxic, their use is contraindicated in terms of, for example, (1) raised viscosity increases the thickness of the 'unstirred' layer around cells so hindering diffusion of metabolites, (2) alteration of the surface membrane bioelectric potential so disrupting cellular metabolism and receptor activities, (3) antigenicity of proteinaceous expanders, (4) agglutination and haemolysis of red blood cells (RBC's) and (5) blockage of microvasculature and ischemia.

It is envisaged that the solutions of the invention will find general use as base compositions to which additional components can be added, depending upon the specific medical purpose. For instance, it is envisaged that the solutions of the invention could be supplemented with, for example, red blood cells (RBC's), plasma and/or platelets for the generation of artificial blood. Such blood components may be either natural or artificial. Thus, additional chemicals can be added to the base composition as and where required. It is therefore intended that the solutions of the invention will find broad applicability as base compositions where a medical utility requires the expansion, replacement, maintenance and/or supplementation etc of a body fluid with a buffer agent whose $pK_a$ closely matches and behaves like that of imidazole/histidine moieties of hemoglobin ($pK_a$: 7.0) so precluding the use of citrate ($pK_a$: 3.09), lactate ($pK_a$: 3.85) or any similarly unsuitable $pK_a$ buffer agent as well as inorganic phosphate ions with their reported deleterious effects on biochemical and physiological processes.

The solutions of the invention find use in methods for treating hypovolemia or the loss of interstitial and extracellular fluid brought about in subjects suffering from severe burns. In addition, the solutions of the invention are applicable in methods of preventing and/or ameliorating reperfusion injury. The solutions of the invention therefore find use as medicaments. For treating hypovolemia and for preventing/ameliorating reperfusion injury, it is preferable to systemically administer the solutions of the invention by the intravenal route. In such instances, the patient will be placed securely in a recumbent position and clinically prepared for the intravenal administration of the specific medicament adopting conventional, clinical procedures. Delivery of the said medicament to the patient will be executed under controlled, supervised conditions until completion of the treatment is achieved.

However, in addition to replacing, maintaining or expanding blood volume, it is envisaged that the solutions of the inventions will also find other uses which include the following; for maintaining, preserving and irrigating tissues and organs in situ during surgical procedures, for perfusing the abdominal cavity of a subject suffering with an acute renal failure or an acute toxicity condition, and for preserving donor tissues and organs in situ during surgical procedures for their removal from the donor patient. Thus, as well as being administrable through the intravascular route, the solutions of the invention may also be administered by other routes, for example, using intraperitoneal, intradermal, intramuscular, topical or oral routes. In patients with acute renal failure or acute toxicity, the patient will be prepared under anesthesia for surgical intervention whereby cannulae will be inserted into the peritoneal cavity, secured in position to ensure the continuous irrigation with the solution under normothermic temperatures. Removal of the peritoneal cannulae will be performed under surgical conditions once normalcy has been achieved in the patient's blood chemistry analysis.

For the treatment of burns, it is preferable to administer the solutions locally by topical application to the site of the burn itself. In addition however, dehydration brought about as a result of severe burns can be treated through systemic administration of the solutions. In such circumstances, the patient will be placed securely in a recumbent position and clinically prepared for the intravenal administration of the specific medicament adopting conventional, clinical procedures. The location and degree of burn involvement will be assessed in terms of the intravenal site administration of the solution and the requirement for additional therapeutic agents based upon the risk of further infection. This method of therapeutic treatment will result in an outward, extravascular flow of the solution so removing any build up of toxic or infective fauna exudates and thereby require constant monitoring of surgical dressings. In preferred embodiments, the methods, solutions and medicaments of the invention are for use in treating human and non-human mammalian subjects, e.g., humans.

As mentioned above, it is envisaged that one application of the solutions defined herein is for preserving donor organs in situ before, during and after surgical procedures for their removal from the donor subject. Use of the solutions of the invention in this regard could involve, for example, whole body infusion (Extra Corporeal Membrane Oxygenation [ECMO] procedure) with donor kidneys, heart, liver, etc being harvested from a donor cadaver followed by normothermic reperfusion of the isolated organ. Preliminary studies (not shown here) have indicated that RS-I as defined herein (see Examples) has the ability to re-animate hypothermically preserved cadaver human organs allowing such organs to be used in preclinical drug bioassay trials, thereby addressing the problem of Adverse Drug Reactions (ADR) reported to occur using in vitro and in vivo drug assessment in animal models.

It is also envisaged that the solutions of the invention will find use as media for the effective delivery of agents to a subject in need thereof, or in circumstances where the agents are to be tested, for example on non-human subjects. For example, the solutions of the invention may find use as diluents for the delivery of pharmaceutical, test or synergistic agents or, alternatively, for the delivery of stem cells, peptide or genomic derived protein. to a subject in need thereof. The delivery of stem cells could, for example, be brought about by suspending the stem cells in media as defined herein, and delivering the resulting suspension directly to the tissue or organ where required. Under this therapeutic regime, patients will undergo surgical removal of derivative stem cell types, e.g., cardiomyocytes, hepatocytes, which may then be suspended in the solutions of the invention and pre-incubated for 12-18 hours. Further proliferation of the stem cell type will be conducted using current culture media techniques whereafter the cells will be re-suspended in the solution and transported to the patient's bedside under hypothermic or mild hypothermic conditions prior to execution of the therapy. Patients will undergo local or general anesthesia dependant upon the route of administration of the stem cell-derived therapy, e.g., local anesthesia for intramyocardium administration of cardiomyocytes, and the administration of the therapy conducted at normothermic temperatures under good clinical practice. Alternatively, delivery may be effected by administration of the suspension to the lymphatic system.

It will be appreciated that the general methods of administering blood volume expanders, known in the art, can be applied when using the solutions of the invention. In particular, methods for regulating the level of administration required in a particular situation (eg. by reference to maintaining adequate blood pressure and cardiovascular function) can be applied using the information available to the skilled person, having regard to the state of the art.

It will be further appreciated that standard perfusion techniques, known in the art, for bathing and irrigating tissues and organs in situ during surgical procedures and for dialyzing body cavities, can be applied when utilizing the solutions of the present invention.

The invention envisages that specific sub-components of the solutions of the invention can be used individually or in any combination.

Particular embodiments of the invention are described below by way of the following examples. The examples are provided to illustrate embodiments of the invention but are not to be considered as limiting in any way.

EXAMPLE 1

Formulation of RS-I Solution

Formulation

In the following preparations, endotoxin-free Milli-Q purified water (Millipore Corp, Milford, Mass.) or equivalent ASTM Type I water [resistivity no more than 18.0 MΩ-cm at 25° C.] was used throughout, both in the initial stirring, and in the final dilution. The term 'purified water' is used hereinafter to denote water of this quality.

Thiamine pyrophosphate (cocarboxylase), Sigma C4655 was prepared as a 0.4 mg/mL stock solution in purified water and stored frozen in dark glass vials. Choline chloride (Sigma C7527) was prepared as a 17.5 mg/mL stock solution in purified water and stored frozen in glass vials. Human recombinant insulin (Sigma 10259/12643) was prepared as a 0.5 I.U./mL stock solution in purified water acidified to pH 2.4 with 0.12N hydrochloric acid and stored frozen in glass vials.

For the preparation of a 10× concentrate solution of RS-I solution, a stainless steel container was filled with 8 litres of purified water and, the following ingredients were weighed out and added while constantly stirring, in the following order: 642.96 grams of sodium chloride (CFK0484), 37.28 grams of potassium chloride (BDH10198), 18.38 grams of calcium chloride dihydrate (BDS10117), 9.14 grams of magnesium chloride hexahydrate (BDH101494) and 106.61 grams of BES free acid (Sigma B6266), 1.84 milligrams of thiamine pyrophosphate (Sigma C9655) (using 4.6 mL of the stock solution), 0.9899 grams of L-carnitine (Sigma C0238), 0.1397 grams of choline chloride (Sigma 7527) in the form of 8 ml of the stock solution, 1.013 grams of glycerol (Sigma G2025), 2.8 I.U. of human recombinant insulin (5 ml of the stock solution), 0.310 grams of L-aspartate sodium salt (Sigma A6683), 180.2 grams of anhydrous D-glucose (Sigma G7021), 5.07 grams of L-glutamate sodium salt (Sigma G5889) and 5.84 grams of L-glutamine (Sigma G5763). The whole was stirred until completely dissolved and then the final volume of 10 litres was produced by adding further purified water.

The 10× RS-I solution was sterile filtered through a Sartobran $PH_2O$ cartridge/0.2 micrometer filter (Sartorius Corp. USA) into 100 mL sterile sealed glass bottles.

This RS-I solution is a 10 times concentrate of the solution intended for use, but with sodium hydrogen carbonate withheld. When needed, the 10× RS-I solution can be diluted with the appropriate quantity of purified water, and sodium hydrogen carbonate added.

For preparation of the 1× RS-I solution, 100 ml of the above 10 times concentrate RS-I solution may be diluted with 900 mL of purified water to 1 litre with the addition of 2.1 g of endotoxin-free sodium hydrogen carbonate (Sigma 54019) and stored at 8-10° C. prior to use. Sodium hydrogen carbonate is preferably not added to the concentrate solutions before they are stored, since extended storage of the concentrate containing hydrogen carbonate ions may cause precipitations of calcium carbonate. Stock 1× solutions for short-term storage may contain sodium hydrogen carbonate.

For use as a body fluid expander solution, each litre of the solution may contain 100 mg/L of chloramphenicol (Sigma C3175) or other conventional antibiotics or antifungal agents to prevent the risk of bacterial infection.

The following factors should be taken into account when preparing the solution:

1). The method of assembly of the solutions and, specifically;

2). Use of purified water as specified above to make up all stock solutions and the 10 times concentrate bottles of manufactured solutions according to the invention;

3). The methods of preparing sterile stock solutions according to the invention and concentrates should not involve autoclaving or gamma-irradiation. For example, irradiation of the solution to achieve sterility will result in degradation of glutamine, glucose, insulin and thiamine pyrophosphate components;

4). The use of glass bottles for storage of all 10 times stock concentrate solutions;

5). Preparation of solubilised insulin by acidification at pH 2.4 plus storing insulin ingredients and stock solutions at −20° C.;

6). Preparation of thiamine pyrophosphate plus TPP stock solutions stored at −20° C. under dark conditions (see reason below);

7). Preparation of Choline chloride stock solutions stored at −20° C.;

8). Use of magnesium chloride hexahydrate (i.e. 6H$_2$O). This is because if the dehydrate salt is used then it adsorbs water so the weight used to calculate the precise magnesium ion content will be in error—this is a common reason for wrongly made up Krebs solutions in terms of correct magnesium ion and calcium ion levels.

The inclusion of all preferred components, as described in this Example, allows these components to work in synergy to produce an overall balanced physiological effect.

Manufacturing Specifications

1. Stock solutions: Various stock concentrations of solutions according to the invention namely, 1×, 10× and 20× for long-term storage have been prepared, but the preferred stock concentrates are 10× concentrates using purified water sterile filtered into sealed 100 mL bottles for storage under dark conditions at 3 to 8° C. Stock solutions are reconstituted for use as 1× solutions by the addition of 100 mL of 10× concentrates of stock solutions to 900 mL of purified water with the addition of 2.1 g of sodium hydrogen carbonate to give a final pH of 7.22±0.04 at 20° C. Sterile stock 10× concentrations of solutions according to the invention have a pH of 4.6±0.2 and have been shown to remain sterile, and free of precipitations, for periods of up to ten years. The recommended manufactured shelf-life of 10× stock concentrates of solutions according to the invention is 14 months when stored at 3 to 8° C. under dark conditions.

2. Cocarboxylase: Stock solutions of thiamine pyrophosphate chloride (cocarboxylase) are prepared at 18.4 g/mL using endotoxin-free purified water, sterile filtered into dark sealed vials to prevent the photon degradation of thiamine pyrophosphate, and stored frozen prior to the assemblage of 10× stock concentrates of solutions according to the invention.

3. Insulin: Human recombinant insulin is prepared as acidified (pH 2.4) stock concentrated solutions at 0.5 m I.U./mL using endotoxin-free purified water and sterile filtered into sealed vials and stored frozen prior to the assemblage of stock concentrates of solutions according to the invention.

4. Choline: Stock solutions of choline chloride are prepared at 17.45 mg/mL using endotoxin-free purified water and stored frozen in sealed vials prior to the assemblage of stock concentrates of solutions according to the invention.

5. Chloramphenicol is not an essential component of solutions according to the invention but is preferably added, either for storage, or after the storage vials have been opened, to ensure sterility during extended exposure of the solutions to the atmosphere and to lower the risk of infection to subjects treated with the body fluid expander solutions of the invention.

EXAMPLE 2

Final Composition of RS-I Solution

The following Table summarises the composition of RS-I solution for use as a body fluid expander.

TABLE I

| Component | Concentration |
| --- | --- |
| NaCl | 110.00 mmoles/L |
| KCl | 5.00 mmoles/L |
| CaCl$_2$ | 1.25 mmoles/L |
| MgCl$_2$ | 0.45 mmoles/L |
| NaHCO$_3$ | 25.0 mmoles/L |
| BES | 5.00 mmoles/L |
| D-Glucose | 10.00 mmoles/L |
| Glycerol | 0.11 mmoles/L |
| L-Glutamate | 0.30 mmoles/L |
| L-Glutamine | 0.40 mmoles/L |
| L-Aspartate | 0.02 mmoles/L |
| L-Carnitine | 0.05 mmoles/L |
| Choline Chloride | 0.01 mmoles/L |
| TPP (cocarboxylase) | 40.00 nmoles/L |
| Human recombinant insulin | 28 mIU/L |

The solution described in Examples 1 and 2 and referred to herein as RS-I represents a preferred form of the body fluid expander solution in accordance with the invention.

EXAMPLE 3

A Comparison of the Chemical Constituents of RS-I, Human Serum and Human Interstitial Fluid At the present time, and according to the prevailing thinking in the art, the formulation of preservation, perfusate and blood volume replacement solutions is strongly inclined towards adopting the composition of either the intracellular or the extravascular milieu. However, as already noted herein, numerous problems still remain unsolved. In considering the ultrastructural of cell membranes, the inventor has departed from current thinking and taken a different approach, namely that a physiological solution should be so formulated to mimic, in a practical artificial manner, the milieu directly adjacent to the cell membrane, namely, the interstitial fluid phase, so maintaining as far as possible homeostasis and the functional dynamics of the cell membrane and associated receptor and enzyme moities. The resulting successful preservation of cellular function of isolated cells, tissues and organs from animal species and humans, demonstrated in Examples 6 and 7 herein, illustrates the success of this approach.

This Example sets out a comparison of the various levels of components present in human serum, human interstitial fluid and RS-I solution, as given below in Table II.

TABLE II

| Component | Serum | RS-I | Interstitial Fluid [analysed or estimated] |
| --- | --- | --- | --- |
| Sodium ions | 131-148 mmoles/L | 135 mmoles/L | 136 mmoles/L |
| Potassium ions | 3.4-5.2 mmoles/L | 5.0 mmoles/L | 4.4 mmoles/L |
| Calcium ions | 1.12-1.46 mmoles/L | 1.25 mmoles/L | 1.18 mmoles/L |
| Magnesium ions | 0.38-0.72 mmoles/L | 0.45 mmoles/L | 0.51 mmoles/L |
| Chloride ions | 101-111 mmoles/L | 119 mmoles/L | 117 mmoles/L |
| Hydrogen carbonate ions | 21-29 mmoles/L | 25 mmoles/L | 23.9 mmoles/L |

TABLE II-continued

| Component | Serum | RS-I | Interstitial Fluid [analysed or estimated] |
|---|---|---|---|
| Organic acid | 6.4 mmoles/L | 5 mmoles/L (BES) | 7 mmoles/L |
| Glucose | 3.6-6.1 mmoles/L | 10 mmoles/L | 3.3-3.6 mmoles/L |
| Glycerol | 31-131 μmoles/L | 110 μmoles/L | 87 μmoles/L |
| Glutamate | 310-475 μmoles/L | 300 μmoles/L | =serum values |
| Glutamine | 188-320 μmoles/L | 400 μmoles/L | =serum values |
| Aspartate | 1-11 μmols/L | 20 μmols/L | =serum values |
| Carnitine (recomb.) | 35-85 μmols/L | 50 μmols/L | =serum values |
| Choline | 18-70 μmols/L | 10 μmols/L | =serum values |
| Thiamine pyrophosphate | 6-135 nmols/L | 40 nmols/L | =serum values |
| Human insulin (recomb.) | 6-35 mIU/L | 28 mIU/L | 24 mIU/L |
| pH @ 37.4° C. | 7.32-7.45 | 7.30-7.46 | 7.35-7.38 |
| Albumin | 0.65 mmoles/L | NIL | 0.19 mmoles/L |
| Osmolality (mOsm/kg water) | 264-290 | 265-286 | 264-282 |
| Specific Conductivity (mS cm$^{-1}$) | 11.7-12.3 | 11.9-12.6 | 11.8-12.2 |

EXAMPLE 4

A Study to Investigate the Effect of Intravenous Infusions of RS-I Solution Using a Rat Hemorrhagic Model Surgical Procedures in the Animal Laboratory The procedures consisted of a lower midline laparotomy under sterile conditions after induction of full anesthesia using an intramuscular (IM) injection of 0.1 cc Xylocaine+ 0.2 cc ketamine for every 100 gram body weight. Following this, the aorta of the rat is dissected and cannulated under direct vision using a 24 Gauge angiocath. This allows for direct access for large amounts of blood withdrawal as well as administration of solutions. As a maintenance dose, 0.2 cc IM injections of ketamine are given every 25 minutes to all rats. Animals are allowed to breathe spontaneously throughout the experiment and their respiratory rate is continuously monitored. A warmer is used to keep the rats at normal body temperature during experimentation. As a result of the lower midline laparotomy, the bowels become exposed to unveil the abdominal vessels. The bowels are wrapped with wet gauze (soaked in saline) to minimize water loss. At the completion of the experiment, the rat is either sacrificed while under anesthesia or the aortic perforation at the site of the catheter is repaired using 6-0 Prolene figure of 8 sutures and closure of the laparotomy incision using 2-0 Vicryl suture in 2 layers. The rats chosen for the survival part of the study are given intramuscular antibiotics and allowed ad lib feeding post-operatively. This procedure takes 25 to 30 minutes to complete per rat.

Animals and Experimental Groupings

19 Sprague-Dawley rats of similar age (10-12 weeks) and weight (280 to 320 g) were used in the experiments. The rats were randomized by random number assignment to one of 3 arms: (1) replacement of blood volume with an equal volume of physiological saline (5 rats); (2) replacement of blood volume with an equal volume of RS-I solution as defined above (7 rats); or (3) no replacement of blood losses (7 rats). The primary end point of the study here was the death of the animal documented by cardio-respiratory arrest.

Hemorrhage and Resuscitation Protocols

The rats were subjected to serial withdrawals of blood in 2 cc increments (simulating controlled hemorrhage) every 30 minutes. At the end of each withdrawal a 0.1 ml of heparinized solution (1000 units in 20 ml of normal saline) was injected into a heparin lock to avoid blood clotting. The rats were randomly allocated to one of 3 arms as defined above.

The data observed and collected were as follows:
a. Number of blood withdrawals (hence volume of hemorrhage)
b. Respiratory rate (measured every 10 minutes)
c. Time span until death (survival time in minutes from onset of hemorrhage)
d. Visible physical changes
e. Pathology Statistics Survival was defined as the time from the first withdrawal of blood to the time of documentation of cardio-pulmonary arrest. Differences were considered statistically significant when the p-value was less than 0.05 ($p<0.05$). All values were expressed as mean±Standard Deviation (SD). The analyses were performed using SPSS software version 13.0 (SPSS, Inc., Chicago, Ill.).

Results of Study

Summary:

Rats in the 'no' resuscitation arm had the shortest survival times and least blood volume withdrawn. Survival time and mean volume withdrawn were significantly improved by the addition of either normal saline or RS-I. RS-I provided a statistically superior survival time ($p<0.01$) and allowed for a larger volume of blood to be withdrawn compared to physiological saline ($p<0.01$).

Survival Times:

The survival of rats over time as a function of the resuscitation solution used is illustrated in FIG. 1. Rats in the 'no' resuscitation arm had the shortest survival. Survival time was significantly improved by adding either saline replacement of blood losses or RS-I replacement. Both solutions showed a significant difference when compared with the survival time of non-resuscitated rats; the mean difference between RS-1 and 'no' resuscitation groups was 89±13.13 minutes ($p<0.01$), and between saline and 'no' resuscitation was 57±15.87 minutes ($p<0.05$). RS-I was superior to saline and resulted in a statistically significant increase in the survival time. The mean difference in survival times between the RS-I treated rats and saline treated rats was significant at 43.40±6.90 minutes ($p<0.01$).

Blood Volume Withdrawn:

The total volume of blood withdrawn for each of the study arms is set out in FIG. 2. Both groups of fluid resuscitated rats showed a significant difference in the volume of blood withdrawn compared to the control arm of 'no' resuscitation (RS-I to 'no' resuscitation 5.73±0.62 ml and saline to 'no' resuscitation 3.64±0.70 ml, with p<0.01 for both). The mean difference in volume of blood withdrawn from RS-I resuscitated rats in comparison to saline resuscitated rats was found to be statistically significant (p<0.01) at 2.82±0.45 ml.

Respiratory Rates:

FIG. 3 illustrates the respiratory rates of rats over time in the various study arms. RS-I resuscitated rats survived the greatest time and showed a slower decline in the respiratory rate overall, though initially (first 100 minutes) a more rapid descent in respiratory rate was noted. The overall respiratory rate for saline resuscitated rats declined at a rate faster than that of RS-I infused rats and this decline was even faster still for the rats that received no fluid infusion.

Conclusion

RS-I appears to be a more effective plasma substitute than physiological saline with respect to survival time and volume blood loss in a rat model of controlled hemorrhagic shock.

EXAMPLE 5

A Study to Investigate the Safety of Administering RS-I as an Intravenous (IV) Fluid Aim of Study This study was designed as a pilot study to evaluate the safety of RS-I when administered as an intravenous (IV) infusional agent in a large animal model (swine).

Methods 6 pigs were used in this study arm, of both genders, ranging in weight from 27 to 35 kg. The pigs were housed in the animal care facility and were kept NPO (nothing by mouth) overnight on the night prior to the study. Each pig was housed in a separate cage.

On day 0, each pig was initially sedated using an intramuscular injection of ketamine (15 to 20 mg/kg) followed by induction of anesthesia and endometrial intubation. Anesthesia was maintained with halothane to achieve absence of response to surgical stimulation without depression of heart rate. Each pig received pre-operative antibiotic prophylaxis by intramuscular injection of gentamycin 10% (1 cc/10 kg).

A central venous catheter was surgically placed via direct countdown, under strict aseptic conditions, into the left internal jugular vein of each pig. The central line was extensively tunneled in the subcutaneous tissues of the pig to an exit site on the lateral and dorsal aspect of the pig neck and secured in place. This was done for two purposes; to prevent accidental catheter dislodgement and to minimize the risk of line related infections. The animals were then allowed to return to their cages to recover from the anesthetics.

On day 1, each pig was sedated using intramuscular injection of ketamine (35 mg/kg) and xylazine (7 mg/kg). Baseline blood samples were drawn from the central line under aseptic technique and immediately sent to the lab for analysis. The blood profile drawn was tested for complete blood counts, serum chemistry determination: electrolytes, osmolality, pH, glucose, lactate, creatinine, blood urea nitrogen (BUN), serum enzymes (aspartate aminotransferase [SGOT/AST], alanine aminotransferase [SGPT/ALT], total creatine kinase [CK] and lactate dehydrogenase [LDH]), coagulation factors and fibrinogen levels. In addition, blood was taken for measurement of pro-inflammatory activity, e.g., neutrophil activation, interleukin-6 (IL-6) and tumor necrosis factor-alpha (TNF-α), and the samples centrifuged and stored at −80° C. for later evaluation.

After the blood was drawn, each pig had 1.0 L of RS-I (at room temp) infused slowly over 1-2 hours via the central line. The pig was directly monitored during the infusion for any signs of ill health or unusual behaviour/manifestations. The pigs were then allowed to return to their normal living quarters and were monitored by the animal house veterinarian for any signs of ill health or unusual behavior/manifestations.

The same procedure performed on Day 1 was repeated on Day 2 and 3. Prior to each infusion of RS-I the same blood profile (described below) was drawn to evaluate for any ill effects related to the RS-I administration. The pigs were then monitored for 7 days and euthanized humanely on Day 7 by intravenous potassium chloride solution administration under sedation with ketamine. Prior to euthanasia, a final blood sample (Day 7) was collected. Blood samples were also drawn to measure TNF-α and IL-6. These samples were centrifuged at 2000 r.p.m. [20° C.] for 5 minutes and then stored at −80° C. to be later processed using commercially available porcine ELISA assays. A post-mortem examination was performed on every pig, and organs (brain, lungs, liver and kidneys) were harvested and either stored in formaldehyde or frozen at −80° C. for histological examination and apoptotic testing at a later date.

Results

All 6 pigs were observed for 1 week, and all showed behavioural and feeding habits that were within normal limits.

Figure 6D:
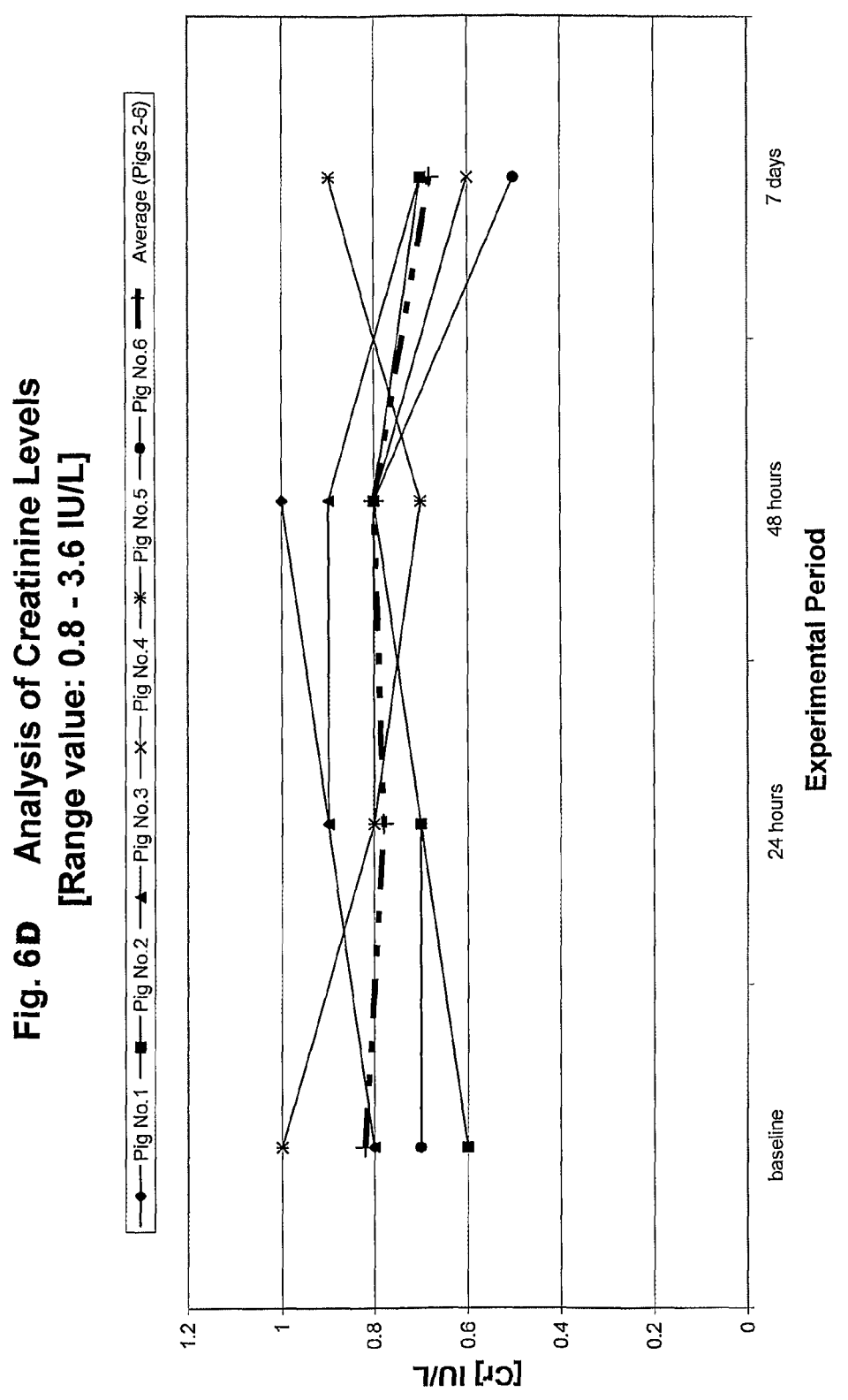

Blood results are set out in FIG. 4 and graphically presented in FIGS. 5-9. These blood results were within normal ranges of swine of this weight category.

Analyses of Blood Profile Categories

1. Electrolyte and Biophysical Parameters:

No significant difference (p<0.05) was observed in serum electrolytes or osmolality over the 7-day experimental period in comparison to baseline ('control') values (FIG. 4G, Table 1; FIG. 5 a-g). Elevation of sodium ion levels to within the published range values was observed after 48 hours in Pig. Nos. 2 and 5 which returned to baseline levels by Day 7 (FIG. 5a). Only Pig No. 6 showed a progressive elevation during the experimental period but returned, as did the overall trend level, to reside within the maximum range value of 150 mmole/L (FIG. 4G, Table 1; FIG. 5a).

No significant change in acid-base balance (i.e., bicarbonate levels; FIG. 5l) or chloride levels (FIG. 4G, Table 1; FIG. 5e, f) were observed during the same experimental periods.

2. Serum Metabolites:

While all serum metabolite baseline levels were naturally elevated on Day 1 following the trauma of surgical manipulative procedures, all (except lactate) exhibited a trend to return to within normal serum values by Day 7 (FIG. 6). There was considerable variation in lactate levels with no statistically significant trend with the lactate levels below reference values (FIG. 6) on Day 2 and 3.

3. Serum Enzymes:

There was the acknowledged elevation of all serum enzymes examined following the trauma of surgical manipulative procedures (FIG. 7) but all (except SGPT [ALT]; FIG. 7b) showed a decline by Day 7 to acceptable serum values indicating a restoration of functional integrity of the heart, liver, lungs and kidneys. The observed elevation of SGPT [ALT] was within the 50 percentile normal serum value and not statistically different (P<0.26) within or among group data again indicating functional integrity of the heart and lungs by Day 7.

4. Blood Components:

Each normovolemic pig had an estimated total blood volume of 1.8-2.3 L (67 mL/kg) and each pig received a total volume of 3 L of RS-I over a period of 72 hours. No hemodilution of RBC count was observed with hematocrit (Hct) values and hemoglobin (Hg) levels remaining with normal ranges up to Day 7 (FIG. 8a,b,c). Equally, lymphocyte count returned to baseline levels over the seven day period investigated (FIG. 8d) with only the white blood cell (WBC) count showing a slight, insignificant elevation by Day 7 (FIG. 8e).

In terms of the blood clotting parameters investigated, only Pig No. 2 showed an anomalous baseline value for platelets which was restored to normal by Day 7 (FIG. 9a). The blood clotting parameters, i.e., prothrombin clotting indices (INR) and activated partial prothromboplastin times (aPTT) (see FIG. 9b, c) remained constant and within published limits. Fibrinogen levels did seem to show a downward trend over the seven day experimental period (FIG. 9d) but again the values remained within acceptable limits for porcine species.

Following the infusion of RS-I over a period of 48 hours, there was an overall trend in restoration of WBC baseline levels (FIG. 8e) and a decrease in lymphocyte levels (FIG. 8d) by Day 7 which suggests the absence of any pro-inflammatory effects.

Inferences

It is to be acknowledged that numerous investigative studies involving swine species have noted great diversity in blood and serum profile values. In the present study, these values were consistent within the swine species examined, there being good statistical correlation.

No hemodilution would appear to have occurred in the normovolemic pigs infused with RS-I solution during the experimental period (FIG. 4G, Table 1).

Characteristically, volume replacement therapies are susceptible to the incidence of inflammatory, anaphylactic, hypercoagulability episodes, seemingly related to the antigenicity and/or toxicity of the various excipients used in the formulation of the blood replacement fluids administered. This does not appear to be the case in the intravenous administration of RS-I solution from the analysis of the blood cell profile data obtained.

Of importance in this pilot study was to evaluate the safety aspects of administering RS-I solution intravenously and that there be no incidence of hyperchloremic (metabolic) acidosis, a common finding in clinical practice with volume replacement fluids. No disturbance in acid-base balance was observed in the pigs examined over a period of seven days, as evidenced by sustained bicarbonate and chloride ion levels.

The tentative observation that suppression of the baseline serum lactate levels occurred in all the pigs studied during the infusion of RS-I solution by Days 2 and 3 (FIG. 6b) would appear to imply that in the RS-I infused normovolemic pig, conditions prevail to optimize:
  a) metabolism of pyruvate (glycolysis) to maintain serum lactate levels;
  b) catabolism of tissue lactate to generate ATP and
  c) resynthesis by the liver (Cori Cycle) to form glucose or glycogen.

All of the pigs studied showed a gradual decrease over the experimental period of serum Lactate Dehydrogenase (LDH), an enzyme intimately linked with lactate/pyruvate metabolism, and characteristically released from tissues and organs during reperfusion injury.

Of particular interest in this study was the observation that the release of those enzymes (e.g., CPK (creatine phosphokinase), SGOT, SGPT) associated with damaged organs (e.g., heart, lung, liver, kidney) during reperfusion of intravenous solutions, while elevated initially on Day 1 following the trauma of the surgical procedures necessitated to monitor bodily functions (see 'Methods), gradually declined to within normal published levels (FIG. 4G, Table 1).

Conclusions

The above detailed study involving daily IV infusions of 1.0 L of RS-I into the pig for a period of 3 days was completed successfully. It is concluded on the basis of the results obtained that RS-I possesses no apparent safety issues when administered intravenously to farm swine under clinically acceptable conditions.

EXAMPLE 6

A Study of Isolated Kidney Function Following Preservation Using RS-I

Methods

Non-heart beating donor (NHBD) pig kidneys were preserved for 2 hours under 'cold' (0° C. to 4° C.) static (CS) conditions in either RS-I or the commercial hypothermic preservation solutions, Soltran or UW (University of Wisconsin) or for 2 hours under 'warm' (31° C.) static (WS) conditions. The kidneys were subsequently reperfused with a 50:50 autologous blood/Lactated Ringer's perfusate mixture under normothermic conditions for periods of 6 to 8 hours.

Results

Functional parameters measured in isolated pig kidney after 6 hours of normothermic perfusion with autologous blood are set out in Table III below, where 'n' represents the number of kidneys tested:

TABLE III

| Functional parameters after 6 hours perfusion | RS-I 4° C. storage (n = 6) | RS-I 30° C. storage (n = 6) | Soltran Flush 4° C. storage (n = 6) | UW Flush 4° C. storage (n = 6) | 'p' value |
|---|---|---|---|---|---|
| pH | 7.37 ± 0.15 | 7.30 ± 0.09 | 7.21 ± 0.1 | 7.23 ± 0.12 | 0.1468 |
| Hydrogen carbonate | 21.8 ± 6.83 | 17.6 ± 4.24 | 14.6 ± 3.08 | 15.3 ± 4.26 | 0.154 |
| Base excess | −4.7 ± 9.16 | −10 ± 5.9 | −9.7 ± 5.90 | −13.5 ± 6.4 | 0.248 |
| Serum K$^+$ levels | 5.83 ± 0.34 | 8.01 ± 1.22 | 7.73 ± 1.21 | 8.23 ± 1.27 | 0.003 |
| O$_2$ consumption ml/min/g | 47.3 ± 12.11 | 28.7 ± 6.53 | 31 ± 6.26 | 33.7 ± 15.1 | 0.059 |

TABLE III-continued

| Functional parameters after 6 hours perfusion | RS-I 4° C. storage (n = 6) | RS-I 30° C. storage (n = 6) | Soltran Flush 4° C. storage (n = 6) | UW Flush 4° C. storage (n = 6) | 'p' value |
|---|---|---|---|---|---|
| % weight gain | 12.7 ± 9 | 30.3 ± 9.3 | 21.2 ± 7.7 | 29.7 ± 3.44 | 0.0109 |
| Total urine output (ml) | 692 ± 230 | 257 ± 118 | 536 ± 221 | 410 ± 153 | 0.0103 |
| RBF ml/min/100 g | 79.3 ± 17.89 | 48 ± 11.28 | 50 ± 10.16 | 55.5 ± 21.9 | 0.0214 |
| RVR mmHg/ml/min | 0.4 ± 0.09 | 0.73 ± 0.26 | 0.52 ± 0.09 | 0.8 ± 0.43 | 0.0173 |

The present study revealed that RS-I significantly outperformed other preservation solutions in maintaining renal function as assessed following kidney re-animation in autologous blood. Analyses of the data obtained over the reperfusion periods revealed that kidneys preserved in RS-I at 4° C. exhibited (1) increased oxygen consumption, (2) increased creatine clearance rates, (3) increased renal blood flow [RBF], (4) increased urine output, (5) decreased renal vascular resistance [RVR], (6) deceased weight gain (i.e. less oedema), (7) stable blood pH and retention of acid-based balance [bicarbonate ion levels], and (8) negligible loss of intracellular $K^+$.

Of particular significance is the observed stability of blood pH and retention of the neutral acid-base balance ($H^+/HCO_3^-$). This observed stability indicates that in RS-I preserved kidneys, the major pH buffering system, the glutamine-ammonia shuttle, had not been compromised as was observed with the other two commercially available preservation solutions (see Table III above). Of additional significance was the observation that in those kidneys preserved for 2 hours under 'warm' (WS) ischemic conditions in AQIX®RS-I, subsequent reperfusion over 6-8 hours resulted in a restoration of the ADP:ATP balance (see FIG. 10).

The ADP:ATP ratio levels were highest in the pre-perfusion biopsies and indicative of the ischaemic damage sustained during the CS/WS storage periods (FIG. 10). However, after 6 hours perfusion, the ratio had improved in both groups showing recovery of cellular function but with no significant difference (p=0.71) observed between the CS and WS groups of kidneys (M D Kay et al., 2006; Transplant International 20 (1), 88-92).

EXAMPLE 7

Assessing the Capability of RS-I to Maintain Isolated Mammalian Organ and Tissue Preparation Viability Over Various Time Periods of Preservation Methods Functional viability of mammalian tissue and organ preparations was assessed following storage/perfusion of the tissues/organs for various periods in RS-I solution. Viability was assessed using a variety of functional indicators, e.g., maintenance of cell membrane potentials, neurotransmitter output, myogenicity, membrane receptor sensitivity, enzyme functions, histological changes, etc.

Results

Table IV below reveals the ability of RS-I solution to maintain functional viability of various mammalian animal and human tissues and organs preparations over preservation periods of varying length (between 0.3 to 10 days).

TABLE IV

| | | | Preservation Conditions | |
|---|---|---|---|---|
| Species | Tissue/Organ Preparations | Max$^m$ Days Stored | Stored ° C. | Experimental ° C. |
| rat | jejunum | 9.0 | 8-12 | 35 |
| | jejunum | 1.5 | — | 35 |
| | ileum | 8.0 | 8-12 | 35 |
| | ileum | 1.3 | — | 20-35 |
| | colon | 5.0 | — | 20-35 |
| | uterus | 3.0 | — | 35 |
| | uterus | 10.0 | 8-12 | 35 |
| | detrusor muscle | 2.0 | — | 20-35 |
| | diaphragm muscle | 0.6 | — | 35-37 |
| | diaphragm muscle | 2.0 | — | 20-35 |
| | soleus muscle | 1.1 | — | 20-35 |
| | heart | 0.8 | — | 35-37 |
| | heart | 2.1 | — | 20-25 |
| | heart-lung | 1.2 | — | 20-35 |
| | RBC's | 4.0 | No haemolysis at 4° C. | |
| | kidney | 1.0 | — | 20-35 |
| | liver | 0.3 | — | 35 |
| rabbit | intestine (jejunum) | 5.0 | 8-12 | 37 |
| | intestine (jejunum) | 2.0 | — | 20-37 |
| | uterus | 7.0 | 8-12 | 37 |
| | superior cervical ganglion | 2.0 | 8-12 | 37 |
| | | 0.8 | — | 37 |
| | RBC's | 3.0 | No haemolysis at 4° C. | |
| guinea pig | ileum | 7.0 | 8-12 | 37 |
| | detrusor muscle | 4.0 | 8-12 | 37 |
| | detrusor muscle | 1.0 | — | 20-37 |
| | heart | 0.4 | — | 20-37 |
| mouse | soleus muscle | 0.9 | — | 20-35 |
| | diaphragm muscle | 1.5 | — | 20-35 |
| | intercostal muscle | 0.9 | — | 20-35 |
| pig | kidney | 0.8 | 0-4 | 37 |
| | kidney | 0.8 | 30 | 37 |
| human | intercostal muscle | 1.3 | — | 37 |
| | kidney (organ) | 1.5 | 0-4 | 37 |
| | intestine (organ) | 0.3 | — | 37 |
| | colon (biopsy) | 1.3 | 0-4 | — |
| | lung (organ) | 0.3 | — | 37 |
| | lung bronchi (biopsy) | 0.8 | — | 37 |
| | atrial trabeculae (biopsy) | 0.6 | — | 37 |
| | liver (organ) | 0.3 | — | 37 |
| | RBC's | 1.3 | 0-4 | — |
| | RBC's | 0.3 | — | 37 |
| | Leucocytes | 0.8 | — | 37 |

EXAMPLE 8

A Preclinical Study to Compare the Efficacy of RS-I Fluid with Autologous Blood and Saline Solution when Administered Intravenously in a Hemorrhagic Pig Model Aim of Study To investigate the efficacy of RS-I as a resuscitation (volume expansion) solution as well as its efficacy at reducing tissue reperfusion injury following hemorrhagic trauma in the pig compared to replacement with autologous blood or Lactated Ringers (LR), a commonly used blood volume expansion solution in clinical applications.

Methods

In this study, 23 randomly selected non-syngeneic farm pigs were used in the four experimental groups, namely, 3 'sham' (control), 6 autologous blood, 6 RS-I solution and 6 LR solution. Under standardized general anesthesia conditions, the animals were instrumented to allow for full measurement of all hemodynamic profile. Pigs were then rapidly hemorrhaged from the femoral artery until the MAP reached 30 mm Hg. Hemorrhage was continued as needed to maintain the MAP at 30+/−2 mm Hg for 45 minutes. Shed blood was collected in ACD treated bags and the net weight used to estimate volume of hemorrhaged blood.

At the conclusion of the 45-minute shock period, animals received either Lactated Ringer solution (LR) or RS-I solution equal to three-four times the shed blood volume, Shed whole autologous blood or no resuscitation ('sham' control group).

The resuscitation fluids were given in a dynamic manner, incrementally, over a 2-hour period to maintain the MAP at 60+/−2 mm Hg. All hemodynamic parameters were measured at baseline; at initiation of the 45-minute shock period, at 30 minutes of shock; at 45 minutes (completion) of shock; and at 30, 60, 90, and 120 minutes of resuscitation. Blood samples for blood gas analysis, lactate measurement, complete blood counts, serum chemistry determination: electrolytes, glucose, osmolarity, serum enzymes (aspartate aminotransferase [SGOT/AST], alanine aminotransferase [SGPT/ALT], total creatine kinase [CK] and lactate dehydrogenase [LDH]) and coagulation profile were drawn at the same time intervals.

Levels of neutrophils activation were measured via myloperoxidase enzymatic method as well as TNF-alpha, IL-6 levels as indices of apoptotic (cell death) phenomena.

After resuscitation, the animals had their cannulae removed leaving the neck venous catheter for daily blood withdrawals. During the 7 post operative days the animals were observed for any behavioral changes and underwent blood withdrawals on post-operative days 1, 2 and 7. The animals were subsequently humanely sacrificed on post-operative day 7 to examine for any pathological evidence of reperfusion injury in the brain, kidney, lung and liver.

Results

General:

All 18 pigs in the surviving three experimental groups were observed for 1 week and all showed behavioural and feeding habits that were within normal limits.

Haemodynamics:

Recovery times during the first 60 minutes of resuscitation for mean arterial (see FIG. 11), central venous, pulmonary arterial occlusion pressures in the RS-I group pigs were fastest and comparable to the autologous blood group pigs but slowest in the LR group pigs. Restoration of cardiac output was significantly quicker and greater in the RS-I group pigs in comparison to both autologous blood and the LR group pigs (see FIG. 12).

Blood Profiles:

Serum electrolyte concentrations by post-operative day 7 had been restored to within normal levels for all experimental groups except for elevation of the sodium ion concentration in the LR group pigs. Anion gap and Strong ion difference was within normal limits in all groups of pigs by post-operative day 7.

Enzyme levels were elevated during post-operative days 1 and 2 but returned to baseline levels by post-operative day 7. No significant change in blood clotting parameters was observed during the seven day experimental period (see, FIG. 13).

Pathology:

On post-operative day 7, evidence of reperfusion injury was absent in the lung and liver and insignificant in the kidney of both the RS-I and autologous blood group pigs but was a significant and prevalent feature in these three organs within the LR group pigs (see FIG. 13).

The invention claimed is:

1. A method of expanding, maintaining or replacing blood volume in a subject, by administering intravenously to the subject a buffered body fluid expander solution comprising:
    i) N,N-bis(2-hydroxyethyl)-2-aminoethanesulfonic acid (BES), wherein BES is present at a concentration of from 1 to 12 mmoles/L;
    ii) calcium ions and magnesium ions at a molar concentration ratio of 5:1 to 1:1, wherein said calcium ions are at a concentration of from 1.1 to 1.5 mmoles/L;
    iii) from 21 to 35 mmoles/L hydrogen carbonate ions;
    iv) from 100 to 150 mmoles/L sodium ions;
    v) from 2.5 to 6.2 mmoles/L potassium ions; and
    vi) from 96 to 126 mmoles/L chloride ions;
wherein the buffered body fluid expander solution does not include a plasma expander.

2. The method of claim 1 wherein hypovolemia is treated.

3. The method of claim 1 wherein BES is present at a concentration of 5 mmoles/L.

4. The method of claim 1 wherein the buffered body fluid expander solution is free of citrate and lactate buffer.

5. The method of claim 1 wherein the molar concentration ratio of calcium ions and magnesium ions is from 4:1 to 2:1.

6. The method of claim 1 wherein the buffered body fluid expander solution comprises 1.1 to 1.4 mmoles/L calcium ions and 0.2 to 0.6 mmoles/L magnesium ions.

7. The method of claim 1 wherein the buffered body fluid expander solution is free of serum and/or serum extract.

8. The method of claim 1 wherein the buffered body fluid expander solution comprises 25 mmoles/L hydrogen carbonate ions.

9. The method of claim 1 wherein the buffered body fluid expander solution further comprises one or more of:
    (a) 2 to 11 mmoles/L glucose;
    (b) 50 to 150 μmoles/L glycerol;
    (c) 7 to 15 μmoles/L choline;
    (d) 5 to 400 μmoles/L glutamate;
    (e) 5 to 200 μmoles/L aspartate;
    (f) 100 to 2000 μmoles/L glutamine;
    (g) 15 to 215 μmoles/L pyroglutamate;
    (h) 20 to 200 μmoles/L arginine;
    (i) 1 to 120 nmoles/L thiamine pyrophosphate;
    (j) 40 to 70 μmoles/L D- or DL or L-carnitine; and
    (k) 5 to 200 m I.U./L porcine or human insulin.

10. The method of claim 1 wherein the buffered body fluid expander solution comprises:
(a) 5 mmoles/L BES;
(b) 1.25 mmoles/L calcium ions;
(c) 0.45 mmoles/L magnesium ions;
(d) 25 mmoles/L hydrogen carbonate ions;
(e) 5 mmoles/L potassium ions;
(f) 118 mmoles/L chloride ions;
(g) 135 mmoles/L sodium ions
(h) 10 mmoles/L D-glucose;
(i) 110 µmoles/L glycerol;
(j) 10 µmoles/L choline;
(k) 300 µmoles/L L-glutamate
(l) 20 µmoles/L L-aspartate;
(m) 400 µmoles/L L-glutamine;
(n) 40 nmoles/L thiamine pyrophosphate;
(o) 50 µmoles/L L-carnitine; and
(p) 28 m I.U./L recombinant human insulin.

11. The method of claim 1 wherein the buffered body fluid expander solution further comprises an antibiotic component.

12. The method of claim 11 wherein the antibiotic component comprises 10 to 150 mg/L chloramphenicol.

13. The method of claim 1 wherein the pH of the buffered body fluid expander solution is from 7.05 to 7.5 at a temperature range of from 4 to 38° C.

14. A method of expanding, maintaining or replacing extravascular body fluid volume in a subject,
by administering intravenously to the subject a buffered body fluid expander solution comprising:
i) N,N-bis(2-hydroxyethyl)-2-aminoethanesulfonic acid (BES), wherein BES is present at a concentration of from 1 to 12 mmoles/L; and
ii) calcium ions and magnesium ions at a molar concentration ratio of 5:1 to 1:1, wherein said calcium ions are at a concentration of from 1.1 to 1.5 mmoles/L;
iii) from 21 to 35 mmoles/L hydrogen carbonate ions;
iv) from 100 to 150 mmoles/L sodium ions;
v) from 2.5 to 6.2 mmoles/L potassium ions; and
vi) from 96 to 126 mmoles/L chloride ions;
wherein the buffered body fluid expander solution does not include a plasma expander.

15. The method of claim 14 wherein the method is a method of treating the loss of extracellular and interstitial fluid in a subject suffering with burns.

16. The method of claim 1 wherein the method of treatment is under normothermic conditions.

17. The method of claim 1 wherein the method is a method of reducing or preventing reperfusion injury.

18. The method of claim 2 wherein the hypovolemia results from dehydration and/or burns and/or bleeding and/or is drug induced.

19. The method of claim 1 wherein the buffered body fluid expander solution is free of inorganic phosphates.

20. The method of claim 14 wherein the method of treatment is under normothermic conditions.

21. The method of claim 14 wherein the method is a method of reducing or preventing reperfusion injury.

22. The method of claim 14 wherein BES is present at a concentration of 5 mmoles/L.

23. The method of claim 14 wherein the buffered body fluid expander solution is:
(i) free of citrate and lactate buffer; and/or
(ii) free of serum and/or serum extract; and/or
(iii) free of inorganic phosphates.

24. The method of claim 14 wherein the molar concentration ratio of calcium ions and magnesium ions is from 4:1 to 2:1.

25. The method of claim 14 wherein the buffered body fluid expander solution comprises 1.1 to 1.4 mmoles/L calcium ions and 0.2 to 0.6 mmoles/L magnesium ions.

26. The method of claim 14 wherein the buffered body fluid expander solution comprises 25 mmoles/L hydrogen carbonate ions.

27. The method of claim 14 wherein the buffered body fluid expander solution further comprises one or more of:
(a) 2 to 11 mmoles/L glucose;
(b) 50 to 150 µmoles/L glycerol;
(c) 7 to 15 µmoles/L choline;
(d) 5 to 400 µmoles/L glutamate;
(e) 5 to 200 µmoles/L aspartate;
(f) 100 to 2000 µmoles/L glutamine;
(g) 15 to 215 µmoles/L pyroglutamate;
(h) 20 to 200 µmoles/L arginine;
(i) 1 to 120 nmoles/L thiamine pyrophosphate;
(j) 40 to 70 µmoles/L D- or DL or L-carnitine; and
(k) 5 to 200 m I.U./L porcine or human insulin.

28. The method of claim 14 wherein the buffered body fluid expander solution comprises:
(a) 5 mmoles/L BES;
(b) 1.25 mmoles/L calcium ions;
(c) 0.45 mmoles/L magnesium ions;
(d) 25 mmoles/L hydrogen carbonate ions;
(e) 5 mmoles/L potassium ions;
(f) 118 mmoles/L chloride ions;
(g) 135 mmoles/L sodium ions
(h) 10 mmoles/L D-glucose;
(i) 110 µmoles/L glycerol;
(j) 10 µmoles/L choline;
(k) 300 µmoles/L L-glutamate
(l) 20 µmoles/L L-aspartate;
(m) 400 µmoles/L L-glutamine;
(n) 40 nmoles/L thiamine pyrophosphate;
(o) 50 µmoles/L L-carnitine; and
(p) 28 m I.U./L recombinant human insulin.

29. The method of claim 14 wherein the buffered body fluid expander solution further comprises an antibiotic component.

30. The method of claim 29 wherein the antibiotic component comprises 10 to 150 mg/L chloramphenicol.

31. The method of claim 14 wherein the pH of the buffered body fluid expander solution is from 7.05 to 7.5 at a temperature range of from 4 to 38° C.

* * * * *